US012669506B2

(12) United States Patent
Hirotsu et al.

(10) Patent No.: US 12,669,506 B2
(45) Date of Patent: Jun. 30, 2026

(54) CANCER DETECTION METHOD USING SENSE OF SMELL OF NEMATODE

(71) Applicant: HIROTSU BIO SCIENCE INC., Tokyo (JP)

(72) Inventors: Takaaki Hirotsu, Fukuoka (JP); Hideto Sonoda, Saga (JP)

(73) Assignee: HIROTSU BIO SCIENCE INC., Tokyo (JP)

( * ) Notice: Subject to any disclaimer, the term of this patent is extended or adjusted under 35 U.S.C. 154(b) by 845 days.

(21) Appl. No.: 17/241,947

(22) Filed: Apr. 27, 2021

(65) Prior Publication Data

US 2021/0356470 A1 Nov. 18, 2021

Related U.S. Application Data

(62) Division of application No. 15/103,264, filed as application No. PCT/JP2014/083320 on Dec. 10, 2014, now Pat. No. 11,719,698.

(60) Provisional application No. 61/982,341, filed on Apr. 22, 2014.

(30) Foreign Application Priority Data

Dec. 10, 2013 (JP) ................................. 2013-255145

(51) Int. Cl.
 *G01N 33/00* (2006.01)
 *C12Q 1/6888* (2018.01)
 *G01N 33/575* (2026.01)

(52) U.S. Cl.
 CPC ..... *G01N 33/57585* (2026.01); *C12Q 1/6888* (2013.01); *C12Q 2600/112* (2013.01); *C12Q 2600/158* (2013.01); *G01N 2333/43534* (2013.01)

(58) Field of Classification Search
 CPC ................................................ G01N 33/57488
 See application file for complete search history.

(56) References Cited

U.S. PATENT DOCUMENTS

| 2006/0191023 A1 | 8/2006 | Gill et al. |
| 2010/0248268 A1 | 9/2010 | Woods et al. |

FOREIGN PATENT DOCUMENTS

| JP | 11-215934 A | 8/1999 |
| JP | 2010-164505 A | 7/2010 |
| WO | WO 2019/077558 A1 | 4/2019 |

OTHER PUBLICATIONS

Lee et al.,2020, Medicinia, vol. 56, pp. 1-11 (Year: 2020).*

Francken et al., 2013, The Breast, vol. 22, pp. 561-568 (Year: 2013).*
Principles of Anatomy and Physiology, 2006, Wiley, 11th Ed., pp. 99-100 and 689-690 (Year: 2006).*
Foley et al., 2010, Labmedicine, vol. 41(11), pp. 683-686 (Year: 2010).*
Cameli et al. (2020, Frontiers in Medicine, vol. 7, pp. 1-7) (Year: 2020).*
Alexander et al., 2016, J. Am. Soc. Nephrol., vol. 27, pp. 3511-3520 (Year: 2016).*
Sorensen M., 2014, Transl. Androl., Urol., vol. 3(3), pp. 235-240 (Year: 2014).*
European Commencement of proceedings before the Board of Appeal for European Patent No. 3081935, dated Jun. 28, 2021.
European Grounds of Appeal for European Patent No. 3081935, dated Sep. 1, 2021.
"Use of N-NOSE test with a blood sample," Citation D34 in Opposition Procedure for European Patent No. 3081935, dated Jan. 29, 2021, 2 pages.
Ache, B. W. and J. M. Young, "Olfaction: Diverse Species, Conserved Principles," Neuron (Nov. 3, 2005), vol. 48, pp. 417-430.
Author Unknown, "Global problem: Cancer incidence and mortality rate", Hirotsu Bio Science, URL: [https://hbio.jp/en/], Dec. 19, 2019, 3 pages total.
Author Unknown, "The Local Authorities of the cities of Kurume and Ogori are the first in Japan to take part in verification trials aimed at commercialization of the N-NOSE nematode cancer screening test", Hirotsu Bio Science, Oct. 8, 2018, 2 pages total.
Auxiliary Request No. 2 for European Patent No. 3081935, dated Dec. 9, 2020, pp. 81-83.
Auxiliary Request No. 3 for European Patent No. 3081935, dated Dec. 9, 2020, pp. 81-83.
Auxiliary Request No. 4 for European Patent No. 3081935, dated Dec. 9, 2020, pp. 81-83.
Auxiliary Request No. 5 for European Patent No. 3081935, dated Dec. 9, 2020, pp. 81-82.
Auxiliary Request No. 6 for European Patent No. 3081935, dated Dec. 9, 2020, pp. 81-82.
Bargmann et al., Odorant-Selective Genes and Neurons Mediate Olfaction in C. elgans, Cell (Aug. 13, 1993), vol. 74, pp. 515-527.
Bijland et al., "Smelling the Diagnosis A Review on the Use of Scent in Diagnosing Disease," The Netherlands Journal of Medicine, vol. 71, No. 6, Jul./Aug. 2013, pp. 300-307.
Brechbühl et al., "Mouse Grueneberg Ganglion Neurons Share Molecular and Functional Features with C. Elegans Amphid Neurons," Frontiers in Behavioral Neuroscience, vol. 7, Article 193, Dec. 9, 2013, pp. 1-12.
Breer, "Olfactory receptors: Molecular basis for recognition and discrimination of odors", Analytical and Bioanalytical Chemistry, vol. 377, Nov. 2003, pp. 427-433.
Consolidated List of Cited Opposition Documents for European Application No. 14870595.7, 3 pages.

(Continued)

*Primary Examiner* — Anoop K Singh
*Assistant Examiner* — David A Montanari
(74) *Attorney, Agent, or Firm* — Birch, Stewart, Kolasch & Birch, LLP

(57) ABSTRACT

A cancer detection method characterised in that a nematode is bred in the presence of bio-related material originating from a test subject, or a processed product of same, and cancer is detected using the chemotaxis due to the sense of smell of the nematode as an indicator.

4 Claims, 38 Drawing Sheets

Specification includes a Sequence Listing.

(56) References Cited

OTHER PUBLICATIONS

Decision for Grant of Patent issued for the corresponding Korean Patent Application No. 10-2016-7018261, dated Mar. 3, 2021, with English translation.

European Letter Accompanying Subsequently Filed Items dated Dec. 9, 2020, for European Patent No. 3081935.

European Notice of Opposition, dated Aug. 27, 2019, for corresponding European Patent No. 3081935.

European Patent Office Interlocutory Decision in Opposition Proceedings dated Apr. 19, 2021 for EP Application No. 14 870 595.7.

European Reply in Relation to Summons to Attend Oral Proceedings dated Jan. 29, 2021, for European Patent No. 3081935.

European Reply to Summons to Attend Oral Proceedings dated Dec. 9, 2020, for European Patent No. 3081935, pp. 1-7.

European Reply to the Notice of Opposition dated Dec. 31, 2019, for European Patent No. 3081935.

European Submission in Opposition Proceedings dated Dec. 9, 2020, for European Patent No. 3081935, 2 pages.

European Submission in Opposition Proceedings dated Jan. 29, 2021, for European Patent No. 3081935, 2 pages.

European Summons to attend oral proceedings dated May 20, 2020, for corresponding European Patent No. 3081935.

Examples of Nematodes Available in Databases, Citation D26 in Opposition Procedure for European Patent No. 3081935, dated Dec. 9, 2020, 1 page.

Extended European Search Report issued Jul. 13, 2017, in European Patent Application No. 14870595.7.

First Office Acton issued May 19, 2017, in Chinese Patent Application No. 201480075291.9, with English translation.

Fukushima, "Just a drop of urine, worms for highly effective cancer screening", The Asahi Shimbun, Oct. 3, 2019, pp. 1-2.

Genbank and Uniprot data on Sri-14, versions Jul. 2012, Citation D29 in Opposition Procedure for European Patent No. 3081935, dated Dec. 9, 2020, 3 pages.

Grishok A. (2005, FEBS Letters, vol. 579, pp. 5932-5939) (Year: 2005).

Gun et al., "Systematic identification of the relationship between olfactory receptors and odorants in C. elegans," Genes & Genetic Systems (Sep. 24, 2012), vol. 87, No. 6, p. 407, 1D-06, Abstract.

Hanai et al. (2012, Biosci. Biotechnol. Biochem., vol. 76(4), pp. 679-684) (Year: 2012).

Hanai et al., "Urinary Volatile Compounds as Biomarkers for Lung Cancer," Bioscience, Biotechnology, and Biochemistry, vol. 76, No. 4, 2012 (online publication Apr. 7, 2012), pp. 679-684.

Hirotsu et al., "A Highly Accurate Inclusive Cancer Screening Test Using Caenorhabditis elegans Scent Detection," PLoS One (Mar. 11, 2015), vol. 10, No. 3, e0118699, pp. 1-15.

Hirotsu et al., "Analysis of the molecular mechanism of signal transduction and identification of novel molecules in neural circuit-dependent odor adaptation in C.elegans," Kagaku Kenkyuhi Hojokin Kenkyu Seika Hokokusho, May 19, 2010, 12 pages total, together with an English translation.

Hirotsu et al., "Comprehensive analysis of olfactory receptors in nematode C. elegans," The Genetics Society of Japan Competition Program Abstracts, vol. 83, Aug. 31, 2011, pp. 114 (4 pages provided), together with an English translation.

Hirotsu et al., "Comprehensive analysis of olfactory receptors in the nematode C. elegans," The Genetics Society of Japan Competition Program (Aug. 31, 2011), Abstracts, vol. 83, pp. 114.

Hirotsu, "Analysis of the molecular mechanism of signal transduction and identification of novel molecules in neural circuit-dependent odor adaptation in C. elegans," Kagaku Kenkyuhi Hojokin Kenkyu Seika Hokokusho (May 19, 2010) (with English abstract).

Identity Matrix, Citation D28 in Opposition Procedure for European Patent No. 3081935, dated Dec. 9, 2020, 1 page.

Iino, T and T. Hirotsu, "Kankaku Juyo no Bunshi Kiko o Saguru Kyu·Aji·Tsukaku no Juyotai Kenkyu to Igaku Oyo eno Kanosei Senchu ni Okeru Kagaku Kankaku to Kagaku Sosei Kodo," Experimental Medicine (Nov. 1, 2000), vol. 18, No. 17, pp. 2314-2319.

Information About the Result of the Oral Proceedings of Feb. 9, 2021, for European Patent No. 3081935.

International Preliminary Report on Patentability and Written Opinion issued Jun. 23, 2016, in PCT International Application No. PCT/JP2014/083320.

International Search Report issued Mar. 31, 2015, in PCT International Application No. PCT/JP2014/083320.

Invitation to Respond to Written Opinion issued Sep. 28, 2017, in Singapore Patent Application No. 11201604743Q.

Italian Statement of Opposition, dated Aug. 20, 2019, for corresponding European Patent No. 3081935.

Iwanaga T. and M. Kato, "Is it Possible to Make a Diagnosis of Cancer by Smelling?," Japanese Journal of Cancer and Chemotherapy (Dec. 15, 2007), vol. 34, No. 13, pp. 2167-2174 (with English abstract).

Kahn-Kirby, "Polyunsaturated Fatty Acids Modulate TRPV-dependent Sensory Signaling in the Nematode Caenorhabditis elegans," Doctor of Philosophy Dissertation, University Of California, San Francisco, UMI No. 3160454, 2004, pp. i-xii and 1-185 (198 pages total).

Khalid et al., "A Pilot Study Combining a GC-Sensor Device with a Statistical Model for the Identification of Bladder Cancer from Urine Headspace," Plos One, vol. 8, Iss. 7, Jul. 8, 2013, pp. 1-8.

Kiontke et al., "Nematodes," Current Biology, vol. 23, No. 19, Oct. 7, 2013, R862-R864.

Korean Office Action, dated Sep. 14, 2020, for Korean Application No. 10-2016-7018261, with an English translation.

Kwak et al., "Volatile biomarkers from human melanoma cells," Journal of Chromatography B (Jul. 15, 2013), vol. 931, pp. 90-96.

Larsch et al., "High-throughput Imaging of Neuronal Activity in Caenorhabditis Elegans," PNAS, Published online Oct. 21, 2013, pp. E4266-E4273.

L'Etoile et al. (2000, Neuron, vol. 25, pp. 575-586) (Year: 2000).

Liao et al., "Behavioural and Genetic Evidence for C. Elegans' Ability to Detect Volatile Chemicals Associated with Explosives," PLoS One, vol. 5, Issue 9, e12615, Sep. 7, 2010, pp. 1-9.

Marked-up Auxiliary Request No. 2 for European Patent No. 3081935, dated Dec. 9, 2020, pp. 81-83.

Marked-up Auxiliary Request No. 3 for European Patent No. 3081935, dated Dec. 9, 2020, pp. 81-83.

Marked-up Auxiliary Request No. 4 for European Patent No. 3081935, dated Dec. 9, 2020, pp. 81-83.

Marked-up Auxiliary Request No. 5 for European Patent No. 3081935, dated Dec. 9, 2020, pp. 81-83.

Marked-up Auxiliary Request No. 6 for European Patent No. 3081935, dated Dec. 9, 2020, pp. 81-83.

Matsumura et al., "Urinary Volatile Compounds as Biomarkers for Lung Cancer: A Proof of Principle Study using Odor Signatures in Mouse Models of Lung Cancer," PLoS One (Jan. 27, 2010), vol. 5, No. 1, E8819, pp. 1-11.

Matsumura, "Volatile biomarkers for lung cancer," Aroma Res. No. 46 (May 28, 2011), vol. 12, No. 2, pp. 129-135 (with English abstract).

Mcculloch et al., "Diagnostic Accuracy of Canine Scent Detection in Early- and Late-Stage Lung and Breast Cancers," Integrative Cancer Therapies, vol. 5, No. 1, 2006, pp. 30-39.

Milanetti et al., "Investigation of the binding between olfactory receptors and odorant molecules in C. elegans organism," Biophysical Chemistry, vol. 255, No. 106264, 2019, pp. 1-8.

Miles, "Roudworms found to sniff out cancer in world-first study at QUT", The Courier-Mail, Sep. 15, 2018, 2 pages total.

O'Halloran et al., "An investigation of chemotaxis in the insect parasitic nematode Heterorhabditis bacteriophora," Parasitology, vol. 127, 2003, pp. 375-385.

Pegg DE. (1976, J. Clin. Path., vol. 29, pp. 271-285) (Year: 1976).

Philips et al. (2007, Cancer Biomarkers, vol. 4, pp. 95-109) (Year: 2007).

Pickel et al., "Evidence for Canine Olfactory Detection of Melanoma," Applied Animal Behaviour Science, 2004, pp. 1-10.

Poinar Jr, "*Nematoda* (Roundworms)," Encyclopedia of Life Sciences, 2005, pp. 1-4.

Sakano, "Neural Map Formation in the Mouse Olfactory System", Neuron, vol. 67, Aug. 26, 2010, pp. 530-542.

(56) References Cited

OTHER PUBLICATIONS

Sengupta et al. (1996, Cell, vol. 84, pp. 875-887) (Year: 1996).

Serizawa, et al., "Negative Feedback Regulation Ensures the One Receptor-One Olfactory Neuron Rule in Mouse", Science, vol. 302, Dec. 19, 2003, pp. 2088-2094.

Shinkai et al., "Behavioral Choice between Conflicting Alternatives Is Regulated by a Receptor Guanylyl Cyclase, GCY-28, and a Receptor Tyrosine Kinase, SCD-2, in AIA Interneurons of Caenorhabditis elegans," The Journal of Neuroscience, vol. 31, No. 8, Feb. 23, 2011, pp. 3007-3015.

Sonoda et al., "Colorectal cancer screening with odour material by canine scent detection," Gut (Jan. 31, 2011), vol. 60, No. 6, pp. 814-819.

Taniguchi et al., "Analysis of correspondence between olfactory receptor and odorant in nematode C. elegans by comprehensive RNAi," The Genetics Society of Japan Competition Program Abstracts, vol. 84, Aug. 31, 2012, p. 97 (4 pages provided), together with an English translation.

Taniguchi et al., "Comprehensive RNAi analysis of the correspondence between olfactory receptors and odorants in the nematode C. elegans," The Genetics Society of Japan Competition Program Abstracts (Aug. 31, 2012) vol. 84, p. 97.

Troemal et al., "Divergent Seven Transmembrane Receptors are Candidate Chemosensory Receptors in C. elegans," Cell, (Oct. 20, 1995), vol. 83, pp. 207-218.

Troemel et al., "Olefactory detection and discrimination in C. elegans," Molecular Biology of the Cell (Jan. 1, 1996), vol. 7, No. Suppl., p. 170A, XP55385790.

Troemel et al., "Reprogramming Chemotaxis Responses: Sensory Neurons Define Olfactory Preferences in C. elegans," Cell, vol. 91, Oct. 17, 1997, pp. 161-169.

Ueda, "Hito no Nioi to Shippei Hifu Gas wa Shindan Shihyo to shite Yuyo ka? Ichi Kosatsu," Aroma Res. No. 37 (Feb. 28, 2009), vol. 10, No. 1, pp. 46-49.

Ward S. (1973, PNAS, vol. 70(3), pp. 817-821) (Year: 1973).

Weiss, "Perfume", Evolutionary Antrhopology, vol. 13, 2004, pp. 205-210.

Wigle et al., "Cancer patterns in Canada," Canada Medical Association Journal, vol. 134, Feb. 1, 1986, pp. 231-235.

Willis et al., "Olfactory Detection of Human Bladder Cancer by Dogs: Proof of Principle Study," BJM, vol. 329, Sep. 25, 2004, pp. 1-6.

Written Submissions on Behalf of the Opponent dated Dec. 9, 2020, for European Patent No. 3081935, pp. 1-47.

Yamamoto et al., "The Trained Sniffer Dog Could Accurately Detect the Urine Samples from the Patients with Cervical Cancer, and Even Cervical Intraepithelial Neoplasia Grade 3: A Pilot Study," Cancers, vol. 12, No. 3291, 2020, pp. 1-12.

Yoshida et al., "Odour Concentration-dependent Olfactory Preference Change in C. Elegans," Nature Communications, Published Mar. 13, 2012, pp. 1-11.

Lanza et al., "C. elegans-based chemosensation strategy for the early detection of cancer metabolites in urine samples," Scientific Reports, vol. 11, No. 17133, 2021, pp. 1-16.

Japanese Office Action for corresponding Japanese Application No. 2020-196320, dated Jan. 18, 2022, with English translation.

Japanese Decision to Grant a Patent dated Jun. 21. 2022 for Application No. 2020-196320, with an English translation.

Reply to the statement setting out the grounds of appeal dated Sep. 1, 2021 for European patent No. 3081935, dated Jan. 4, 2022.

European Communication of the Board of Appeal for European Patent No. 3081935, dated Jul. 27, 2023.

Indian Hearing Notice for Indian Application No. 201617022947, dated Feb. 8, 2023, with English translation.

Wang et al., "The analysis of volatile organic compounds biomarkers for lung cancer in exhaled breath, tissues and cell lines," Cancer Biomarkers, vol. 11, 2012, pp. 129-137.

Written Submissions for Indian Application No. 201617022947, dated May 26, 2023.

Zimmermann et al., "Determination of volatile products of human colon cell line metabolism by GC/MS analysis," Metabolomics, vol. 3, No. 1, Mar. 2007, pp. 13-17.

* cited by examiner

Figure 2

0.5 µl of NaN3 alone

1 µl of sample +
0.5 µl of NaN3

A

B

| Odorant | The number of candidate genes |
|---------|------------------------------|
| *Attractants* | |
| Isoamyl alcohol (Iaa) | 21 |
| Benzaldehyde (Bz) | 50 |
| Butanone (Bu) | 17 |
| Pentanedione (Pd) | 39 |
| Pyrazine (Py) | 56 |
| Trimethylthiazole (Tmt) | 22 |
| *Repellents* | |
| Nonanone (Nona) | 4 |
| Octanol (Oct) | 10 |
| High Iaa | 1 |
| High Bz | 7 |
| High Diacetyl (Da) | 28 |

Method for examining types of cancer

As a result of the studies regarding cancer detection dogs, it is suggested that an odorant and/or a receptor would be different depending on the type of cancer.

Identification of a receptor for eacn type of cancer, using nematodes

Production of a nematode strain which deletes the receptor
(CRISPR/Cas9 genome editing technique)

| Gastric cancer | Lung cancer | Breast cancer | Large bowel cancer | Pancreatic cancer | i) The presence or absence of all cancers is examined using wild-type nematodes.

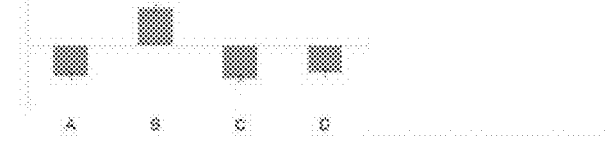

ii) Analysis is carried out using nematode strains deleting the receptor for each cancer species.

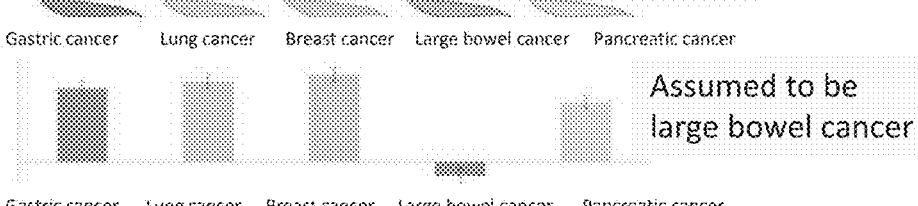

Assumed to be large bowel cancer

CANCER DETECTION METHOD USING SENSE OF SMELL OF NEMATODE

This application is a Divisional of copending application Ser. No. 15/103,264 filed on Jun. 9, 2016, which is the National Phase of PCT/JP2014/083320, filed on Dec. 10, 2014, which claims priority under 35 U.S.C. 119(e) to U.S. Provisional Application No. 61/982,341, filed on Apr. 22, 2014 and under 35 U.S.C. 119(a) to Patent Application No. 2013-255145, filed in Japan on Dec. 10, 2013, all of which are hereby expressly incorporated by reference into the present application.

TECHNICAL FIELD

The present invention relates to a method for detecting cancer using the olfactory system of nematodes.

BACKGROUND ART

Malignant neoplasm including cancer has been the leading cause of death for Japanese people since 1981. According to the World Health Organization, the rate of death from malignant neoplasm in 2005 has been 13% (7,600,000 people) over the world, and it has been predicted that the death rate from malignant neoplasm would continue to increase in the future.

As the stage of cancer is early, mental, physical, economic and social burden on medical care would be light, and curability would also be increased. As the stage of cancer progresses, such curability is decreased, and in the case of unresectable, progressive recurrent cancer, the cancer causes excessive burden and losses and results in a life-prolonging treatment under the current circumstances. Since cancer is developed as a result of abnormality in functions of genes, in almost all types of cancers, a population of 100,000 versus the incidence at each age increases in proportion to the power of 4-6 (Cancer Patterns in Canada, 1982). As such, in all age groups or societies, if cancer can be found and treated at an early stage, burden and losses can be apparently reduced in various situations.

However, in general, early cancer has no symptoms, medical examinees do not have enough motivation to undergo cancer screening under the current circumstances. In fact, the cancer screening rate is approximately 10% to 35% in all types of cancers in Japan. These numerical values are much lower than the goal of the basic plan of Cancer Counter Measures in Japan, which aims 50% or more of the cancer screening rate until 2017. In Japan, in which techniques of treating early cancer, such as endoscopes or surgical techniques, are at a top level in the world, if a high-accuracy cancer screening method, which gives less pain, is simple and inexpensive, and can be carried out on many people as targets, were newly developed and applied, it is no exaggeration to say that it would bring on revolution on cancer treatments in the world.

Several teams including the present inventors have studied cancer using trained dogs (cancer detection dogs), and have reported that cancer has a unique smell, and thus that cancer can be detected in a specimen containing early cancer at a high accuracy of more than 90% (both sensitivity and specificity) (Non Patent Literature 1: Sonoda, H. et al., Colorectal cancer screening with odour material by canine scent detection. Gut, 60, 814-819, 2011).

From these reports, it is considered that a high-accuracy cancer detection system can be constructed by detecting a smell that is specific to a cancer.

However, the ability of such a cancer detection dog depends on an individual difference, and the concentration of dogs is decreased in summer in which temperature rises. Moreover, regarding a method of training detection dogs, there is no specific methodology. Furthermore, even under circumstances in which such a cancer detection dog is in a good condition, five times of tests per day are limits for the dog. A test, which is continuously carried out on a sample, the examination purpose of which is completely unknown, provides a reward that is "playing with a ball" to a cancer detection dog, even if the detection dog behaves incorrectly. This results in a reduction in accuracy. Accordingly, cancer screening, in which detection dogs are used, cannot be applied for business use.

Further, a method for diagnosing cancer, which comprises specifying a volatile substance using an analytical device such as GC/MS (gas chromatography/mass spectroscopy) analysis, has been reported (Non Patent Literature 2: Y. Hanai, et al., Urinary volatile compounds as biomarkers for lung cancer. Biosci. Biotechnol. Biochem. 76, 679-84, 2012) (Non Patent Literature 3: Khalid et al., A pilot study combining a GC-sensor device with a statistical model for the identification of bladder cancer from urine headspace. PLoS ONE, 8, e69602, 2013). However, a volatile substance existing in a daily life is highly likely to become a noise, and thus, enormous amounts of funds and analytical techniques are necessary for the development and production of detection equipment.

RELATED ART LITERATURES

Non-Patent Literatures

Non Patent Literature 1: Sonoda, H. et al., Colorectal cancer screening with odour material by canine scent detection. Gut, 60, 814-819, 2011

Non Patent Literature 2: Y. Hanai, et al. Urinary volatile compounds as biomarkers for lung cancer. Biosci. Biotechnol. Biochem. 76, 679-84, 2012

Non Patent Literature 3: Khalid et al., A pilot study combining a GC-sensor device with a statistical model for the identification of bladder cancer from urine headspace. PLoS ONE, 8, e69602, 2013

SUMMARY OF THE INVENTION

Problem to be Solved by the Invention

It is an object of the present invention to provide a method for detecting cancer, utilizing the olfactory system of nematodes.

Means to Solve the Problem

As a result of intensive studies directed towards solving the aforementioned problem, the present inventor has found that cancer can be detected, using the chemotaxis of nematodes based on the olfaction thereof or the response of olfactory neuron, thereby completing the present invention. Specifically, the present invention is as follows.

(1) A method for detecting cancer, characterized by detecting cancer using, as an indicator, the reaction of nematodes to the smell of a subject-derived bio-related substance or a processed product thereof.

(2) The method according to (1) above, wherein the nematode is *Caenorhabditis elegans*.

3

(3) The method according to (1) or (2) above, wherein the nematode is a wild-type nematode, a mutant nematode, or a transgenic nematode.

(4) The method according to any one of (1) to (3) above, wherein when the nematode shows a positive response to the smell of the subject-derived bio-related substance or a processed product thereof, the subject is determined to have cancer, or to have cancer risk.

(5) The method according to any one of (1) to (4) above, wherein when the response of the olfactory neuron of the nematode is high to the smell of the subject-derived bio-related substance or a processed product thereof, the subject is determined to have cancer, or to have cancer risk.

(6) The method according to any one of (1) to (5) above, wherein the bio-related substance or a processed product thereof is a body fluid, cells, tissues, a culture of the cells or tissues, or a preservative solution of the cells or tissues.

(7) The method according to (6) above, wherein the body fluid is urine.

(8) The method according to (6) above, wherein the preservative solution is a physiologic saline.

(9) A method for identifying a olfactory receptor in nematodes, characterized by identifying a olfactory receptor using nematodes.

(10) The method according to (9) above, wherein the expression or function of a gene encoding the receptor is inhibited, and the reaction of the inhibited nematode to a smell is tested.

(11) The method according to (10) above, wherein the expression or function of the receptor gene is inhibited by RNAi.

(12) The method according to any one of (9) to (11) above, wherein the smell is the smell of cancer types.

(13) The method according to any one of (9) to (12) above, wherein the type of a receptor to be identified is different depending on the cancer types or the concentration of an odorant.

(14) The method according to any one of (9) to (13) above, wherein the nematode is *Caenorhabditis elegans*.

(15) A method for identifying cancer species, characterized by identifying cancer types using, as an indicator, the reaction of nematodes to the smell of a subject-derived bio-related substance or a processed product thereof.

(16) The method according to (15) above, comprising the following steps:
- (a) detecting cancer by the method according to any one of (1) to (8) above,
- (b) testing the reaction of a modified nematode, which has been prepared by modifying a receptor identified by the method according to any one of (9) to (14) above, to the smell of a sample, which has been detected to have cancer in the step (a), and
- (c) determining the cancer types corresponding to the identified receptor to be cancer types as a target of identification, when the reaction to the smell is different between the modified nematode and the nematode used in the step (a).

(17) The method according to (16) above, wherein the modification of the receptor is at least one selected from the group consisting of deletion of the receptor, inhibition of the expression or function of the receptor, and high expression or high-functionalization of the receptor.

(18) A kit for detecting or identifying cancer, which comprises nematodes.

(19) The kit according to (17) above, wherein the nematode is *Caenorhabditis elegans*.

(20) The kit according to (18) or (19) above, wherein the nematode is a wild-type nematode, a mutant nematode, or a transgenic nematode.

(21) A cancer detection system, which comprises:
- a nematode,
- a storage part for storing a bio-related substance or a processed product thereof and the nematode, and
- a detection part for detecting the reaction of the nematode in the storage part to a smell.

Effect of the Invention

According to the present invention, a method for detecting cancer using a nematode is provided. According to the method of the present invention, cancer can be detected with high sensitivity and at low costs. Moreover, according to the method of the present invention, collection and analysis of samples are carried out easily, and also, it is inexpensive. Furthermore, the method of the present invention is able to detect early cancer. Therefore, the method of the present invention is extremely useful for clinical tests for cancer.

BRIEF DESCRIPTION OF THE DRAWINGS

FIG. 2 is a view showing the format of a petri dish used in the method of the present invention.

colo205=large bowel cancer, MKN1=gastric cancer

Figure 19:
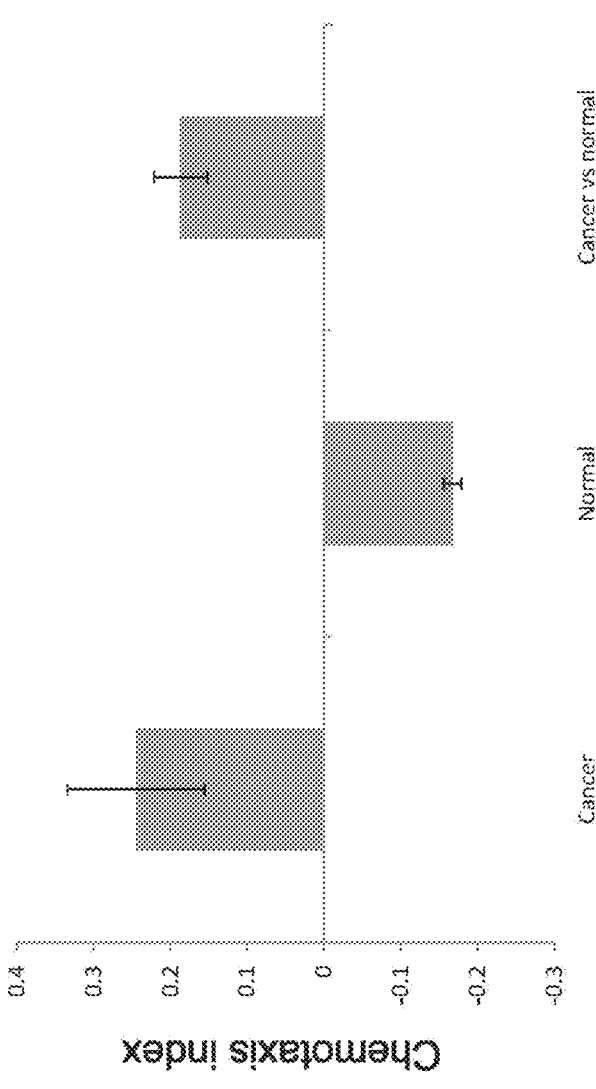

FIG. 19 is a view showing the chemotaxis of nematodes to the cancer tissues and normal tissues of a sigmoid colon cancer patient.

Figure 20:
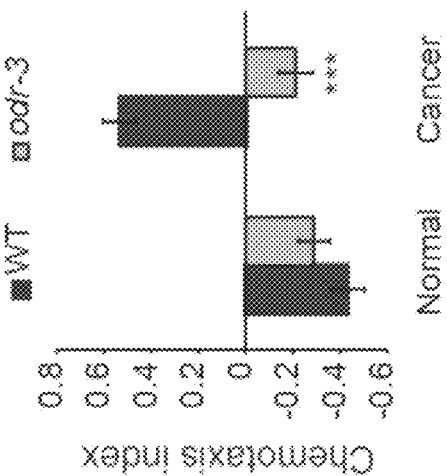
Figure 20:
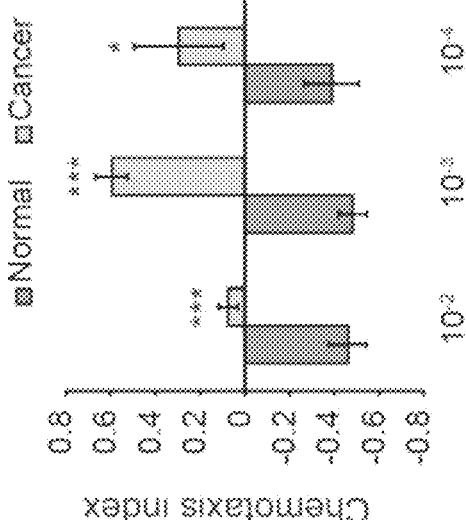

FIG. 20 is a view showing the chemotaxis of nematodes to a diluted solution of a physiologic saline, to which a human cancer tissue section has been added and preserved.

Figure 21:
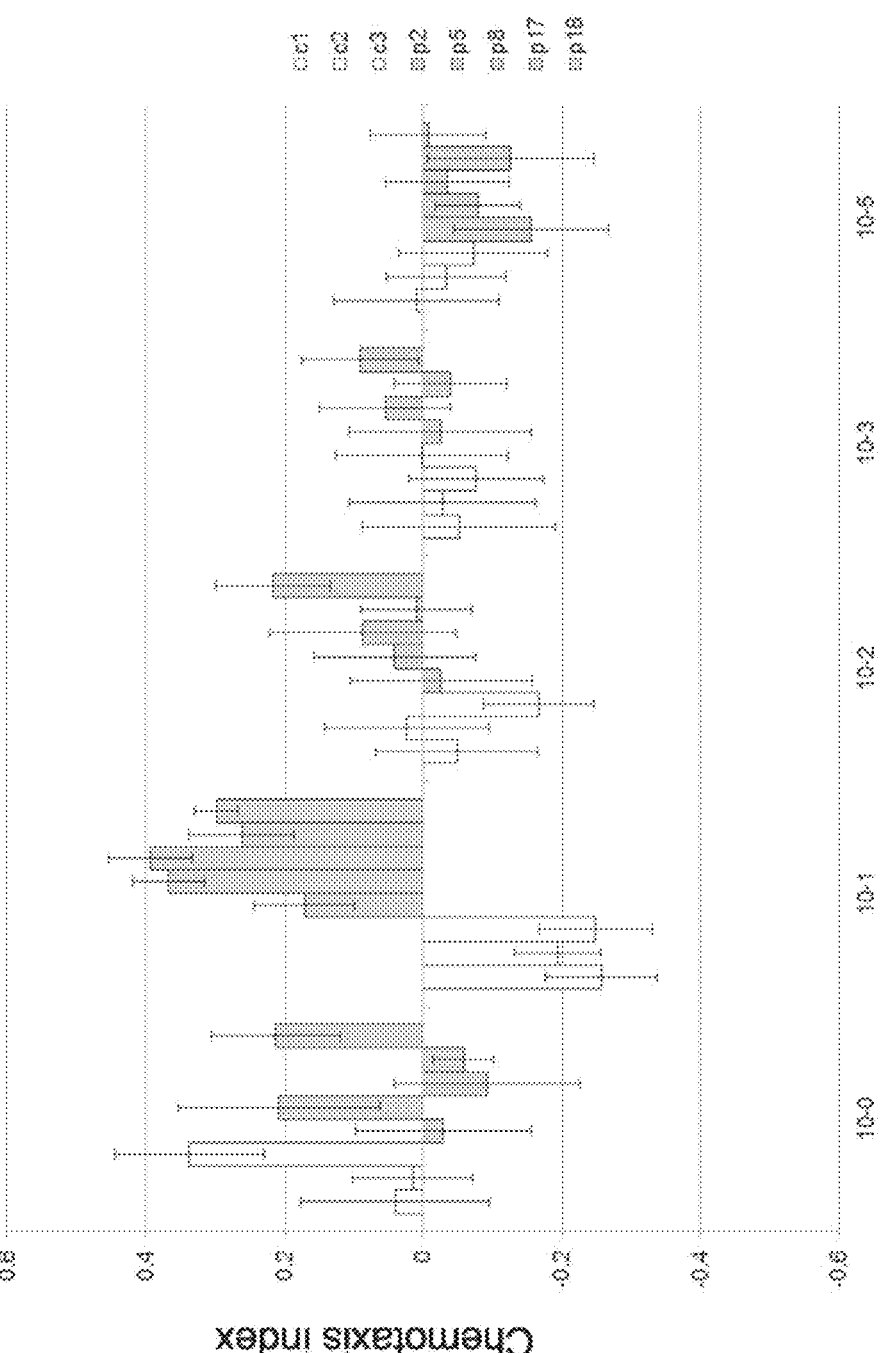

FIG. 21 is a view showing the results obtained by testing the chemotaxis of nematodes, while changing the concentration of urine.

Figure 22:
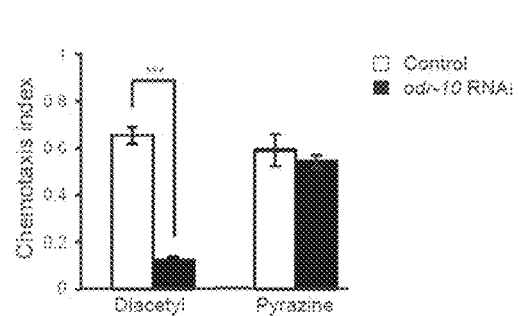
Figure 22:
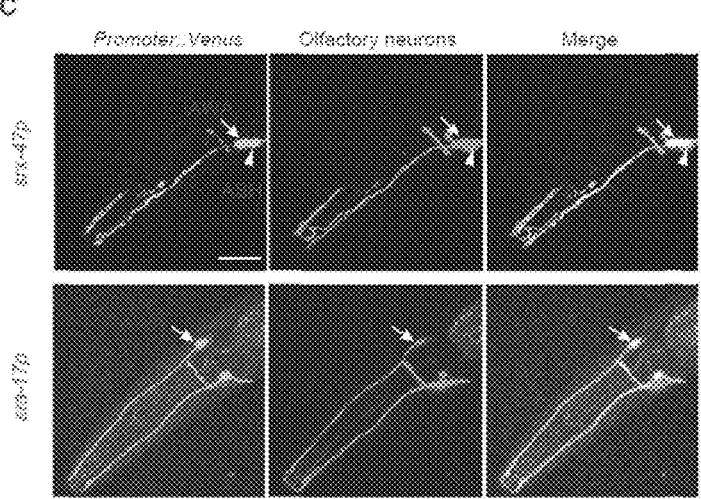

FIG. 22 is a view showing the RNAi screening of an olfactory receptor associated with a response to a specific odorant.

(A) Confirmation of the effectiveness of RNAi screening strategy. The RNAi effect of an eri-1 mutant targeting odr-10 is shown in a chemotactic response to a $10^{-3}$ dilution of diacetyl or $10^{-3}$ dilution of pyrazine. A significant difference from a control is shown (P<0.001, Student's t test). (B) The number of olfactory receptor candidate genes obtained after the third screening, which has been associated with chemotaxis to an odorant. (C) The expression patterns of fluorescent reporters, the expression of which has been induced by a srx-47 or sra-17 promoter. The green color (left column) indicates the expression of the fluorescent protein Venus induced by the promoters of these genes. The magenta color (middle column and right column) indicates the expression of mCherry in AWA, AWB, and AWC olfactory neurons. The expression of srx-47 was observed in AWA and ASH neurons. The expression of sra-17 was detected in AWA neurons. Scale bar: 10 μm.

Figure 23:
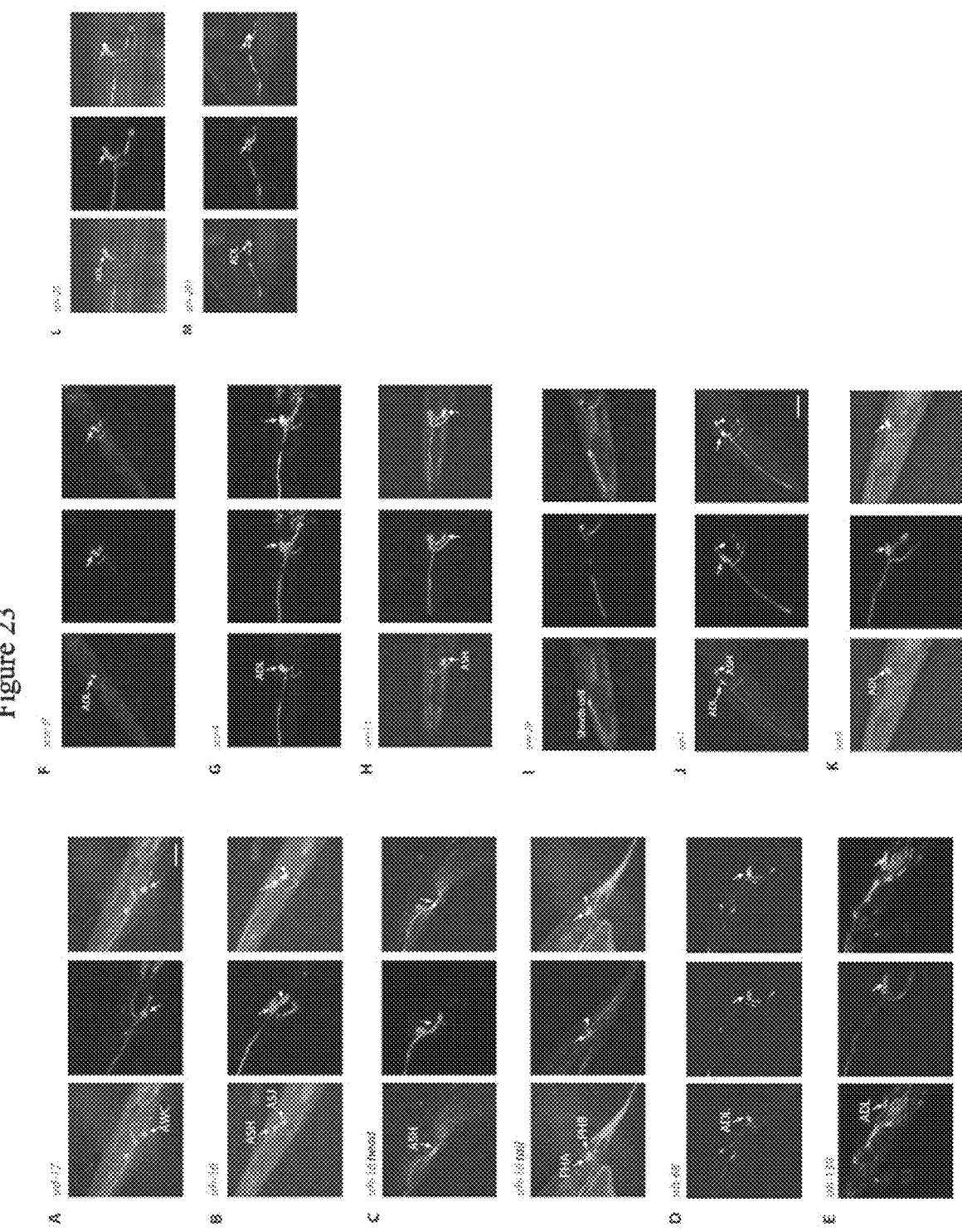

FIG. 23 is a view showing the expression patterns of olfactory receptor candidate genes.

(Left) The green color (left column of A-M) indicates the expression of Venus, which has been induced by the promoters of olfactory receptor candidate genes. (Center) The magenta color (middle column of A-M) indicates (A) the expression of mCherry in AWA, AWB and AWC neurons, or dye-stained sensory neurons (ASH, ASJ, AWB, ASK, ADL, ASI, PHA and PHB neurons) (B-M). (Right) Merged view. All of the images are the left side images of head regions of nematodes, except for C, bottom portions (tail regions). The arrows and the arrowheads indicate the cell bodies of neurons expressing receptor candidate genes. Scale bar=10 μm.

Figure 24:
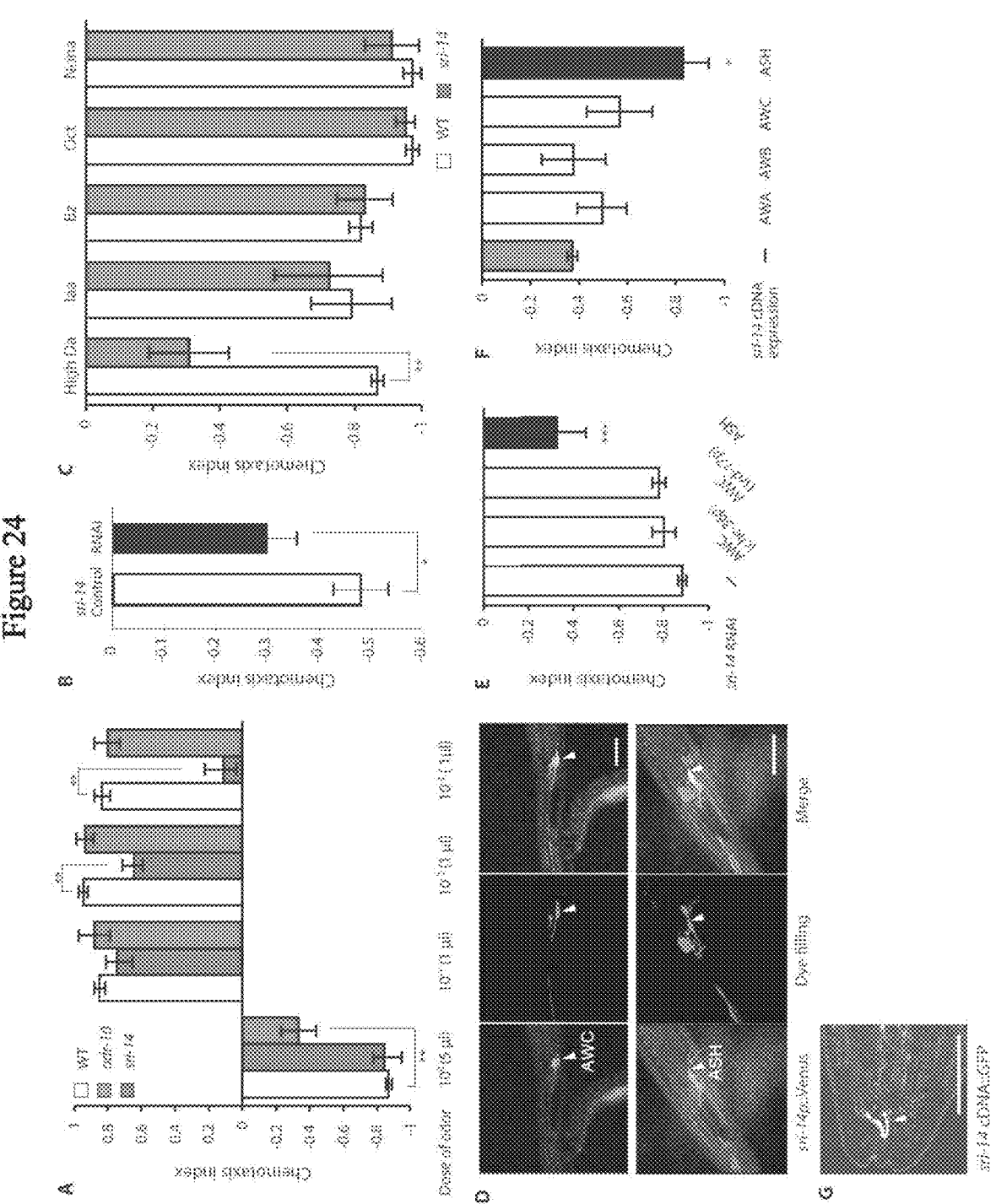

FIG. 24 is a view showing that SRI-14 functions for a response to a high concentration of diacetyl in ASH neurons.

(A) The chemotaxis of wild type (WT), odr-10 and sri-14 mutants to a low concentration of and a high concentration of diacetyl. Diacetyl concentrations are shown in bottom portions (n=5). (B) RNAi effects targeting sri-14 in avoidance response to a high concentration of diacetyl (5 μl, undiluted) (n=8). (C) The chemotaxis of the sri-14 mutant to a high concentration of diacetyl (5 μl, undiluted, Da), isoamyl alcohol (5 μl, undiluted, Iaa) and benzaldehyde (1 μl, undiluted, Bz), and also to the repellents octanol (1 μl, undiluted, Oct) and nonanone (1 μl, undiluted, Nona) (n=6). (D) The expression patterns of fluorescent reporters (green), the expression of which is induced by a sri-14 promoter. The arrowhead indicates the cell body of AWC or ASH identified by mCherry or fluorescent dye, respectively (magenta). (E)

Effects obtained by the ASH- or AWC-specific RNAi of a wild-type nematode on sri-14, with regard to chemotaxis to a high concentration of diacetyl (5 μl, undiluted) (n=5). (F) Effects obtained by the neuron-specific expression of sri-14 cDNA, with regard to a defect in the response of a sri-14 mutant to a high concentration of diacetyl (5 μl, undiluted) (n=5). (G) Localization of SRI-14::GFP in ASH sensory cilia. Scale bar: 10 μm (D and G). The error bar indicates SEM. *P<0.05, P<0.01, *P<0.001, Student's t test (B and C) or Dunnett's test (A, E, and F).

Figure 25:
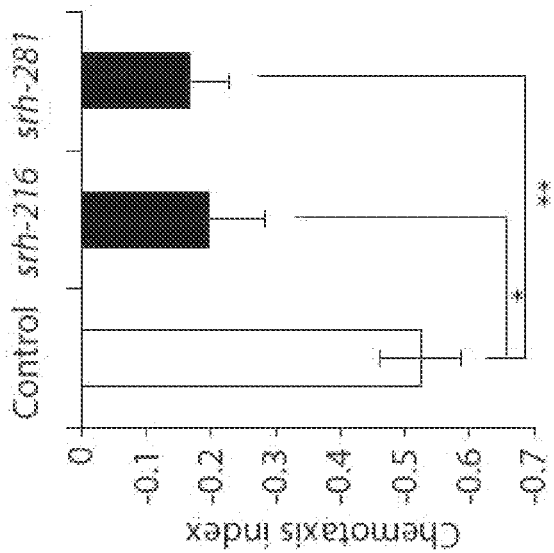
Figure 25:
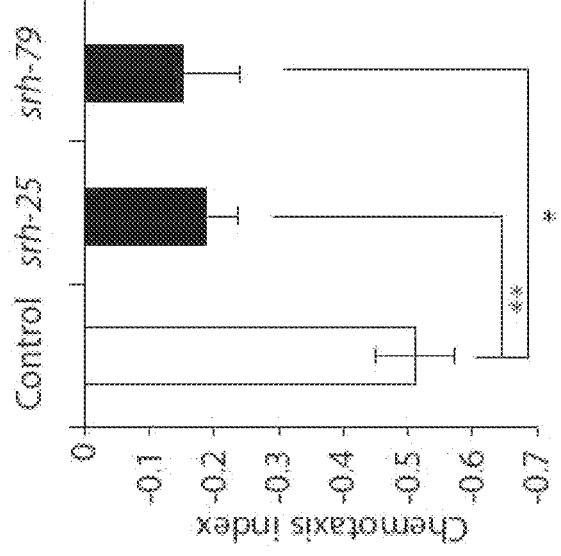

FIG. 25 is a view showing the results obtained by repeatedly assaying the chemotaxis of RNAi-treated nematodes to a high concentration of diacetyl.

In addition to the RNAi of sri-14, the RNAi of srh-25, srh-79, srh-216 or srh-281, among candidate receptor genes regarding the response to a high concentration of diacetyl (5 μl, undiluted) obtained after the third screening, has caused a significant and reproducible defect to an avoidance behavior from diacetyl. The error bar indicates SEM. A significant difference from a control is shown (*P<0.05, **P<0.01; Student's t test including Bonferroni correction).

Figure 26:
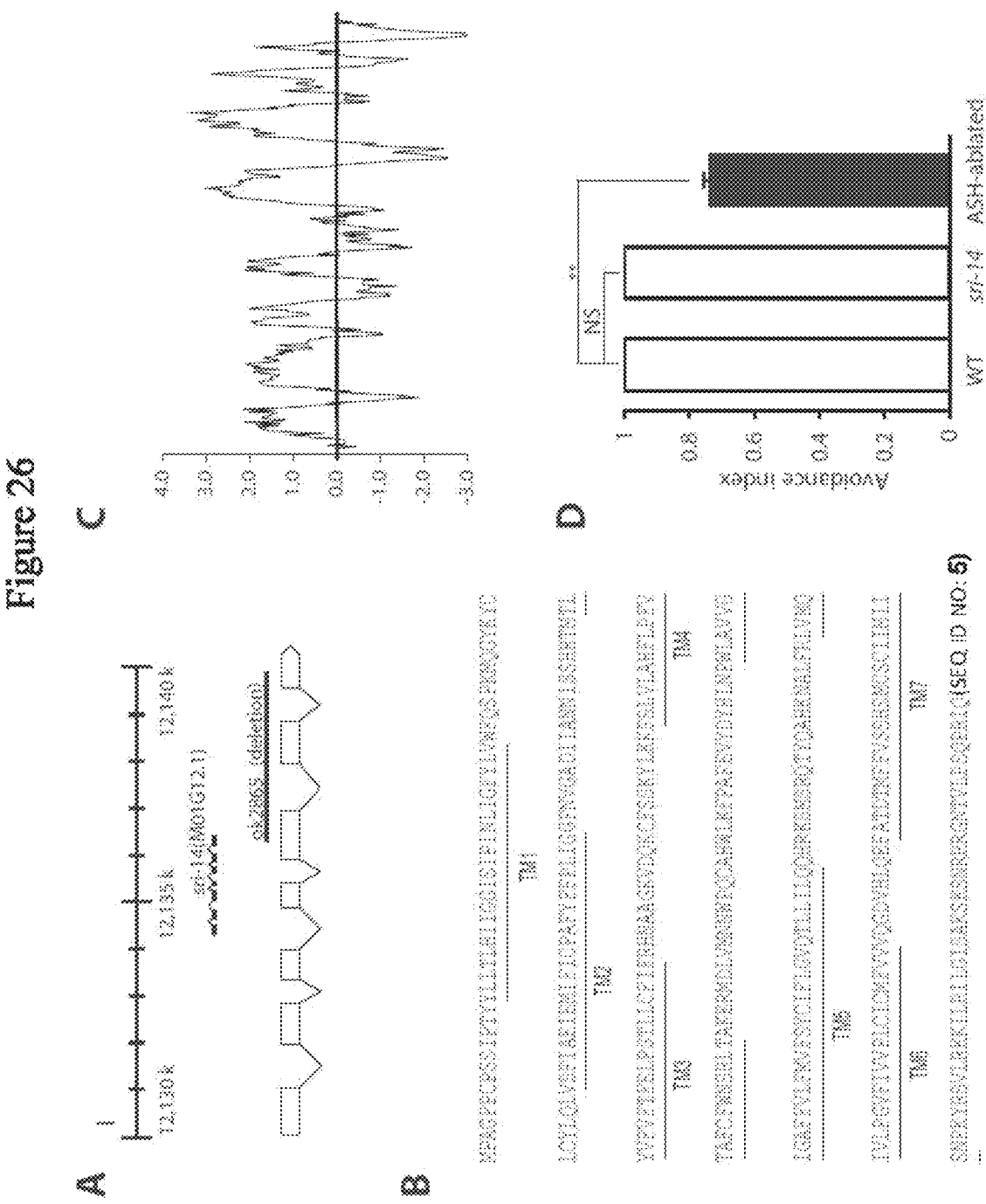

FIG. 26 is a view showing the structure of sri-14.

sri-14 encodes a 7-transmembrane protein. (A) The structure of sri-14 gene. It shows a deletion region of the ok2685 allele. (B) The putative amino acid sequence of SRI-14. It shows a 7-transmembrane domain predicted by a hidden Markov model. (C) A hydrophobic plot of SRI-14. The plot is derived from a hydropathy parameter defined by Kyte & Doolittle. (D) The sri-14 mutant exhibited a normal avoidance behavior to a high osmotic stimulus (4 M NaCl). The error bar indicates SEM. A significant difference from a control is shown (**P<0.01, Dunnett's test).

Figure 27:
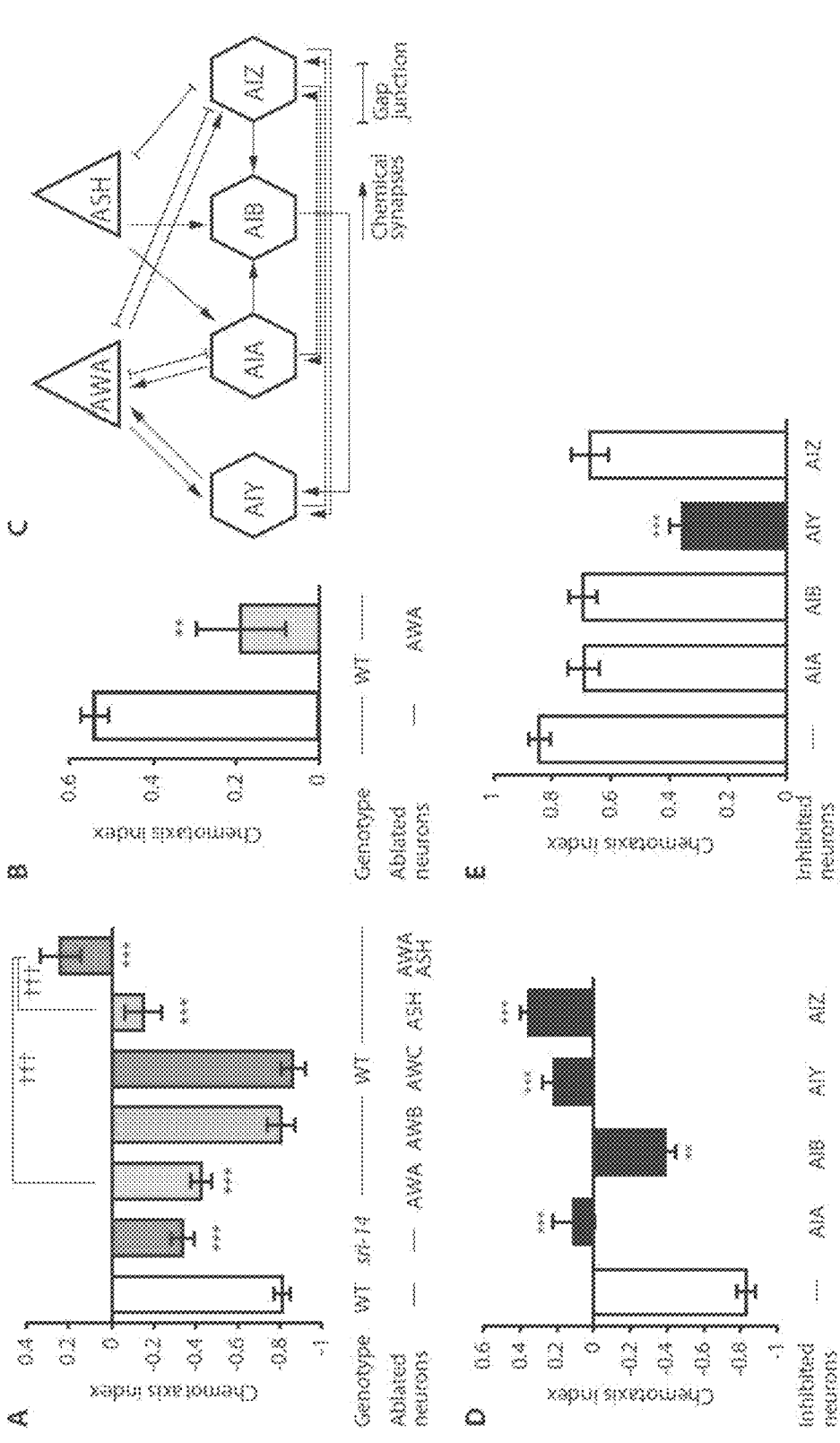

FIG. 27 is a view showing neurons associated with a response to a high concentration of diacetyl. (A) The chemotaxis of wild-type nematodes (n≥8), in which the specific sensory neurons have been ablated, to a high concentration of diacetyl (5 μl, undiluted). (B) The chemotaxis of nematodes, from which AWA has been ablated, to $10^{-3}$ diluted diacetyl. (C) A schematic view showing neuron wirings among AWA and ASH sensory neurons and 4 first-layer interneutrons. (D) The chemotaxis of wild-type nematodes (n≥5), in which the specific interneurons have been inhibited, to a high concentration of diacetyl (5 μl, undiluted). (E) The chemotaxis of wild-type nematodes (n≥5), in which the specific interneurons have been inhibited, to a $10^{-3}$ diluted diacetyl. The error bar indicates SEM. P<0.01, *P<0.001, Dunnett's test; †††P<0.001; Student's t test. In FIG. 27(A), the asterisk indicates a statistically significant difference, compared to a wild-type control strain in which all neurons have been neither ablated nor inhibited.

Figure 28:
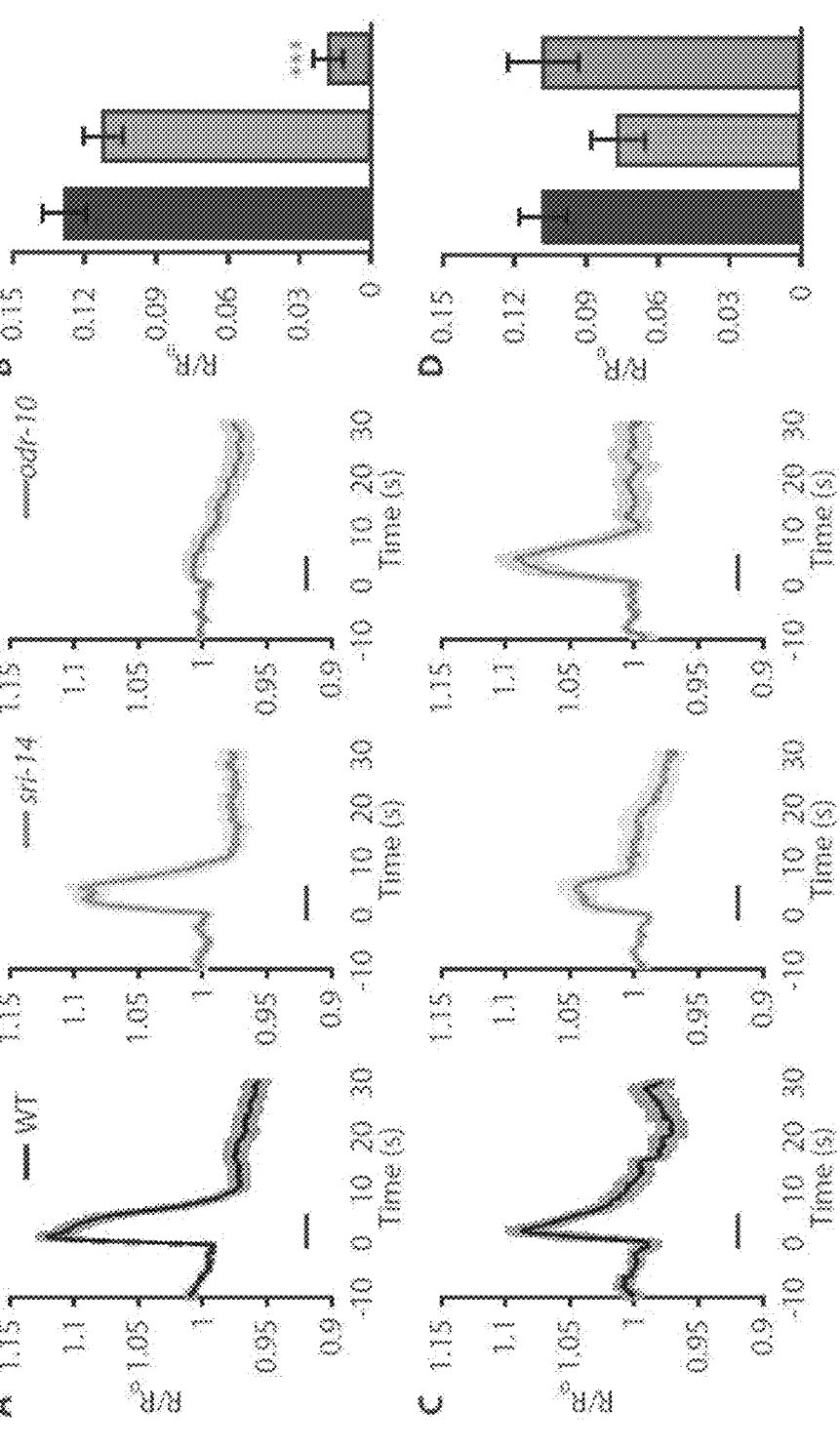

FIG. 28 is a view showing the response of AWA neurons to various diacetyl concentrations. (A) The calcium response of AWA neurons in a nematode of each designated genotype, after stimulation by a low concentration of diacetyl ($10^{-5}$ diluted). The shaded region around the curve indicates SEM (n≥8 in all genotypes). The black bar (left) indicates the presence of diacetyl stimulation. (B) A change in the mean fluorescence 10 seconds after addition of a low concentration of diacetyl ($10^{-5}$ diluted). The error bar indicates SEM. **P<0.01, Dunnett's test (n≥8 in each genotype). The black color (left) indicates WT, the red color (middle) indicates sri-14 mutants, and the blue color (right) indicates odr-10 mutants. (C) The calcium response of AWA neurons in a nematode of each designated genotype, after stimulation by a high concentration of diacetyl ($10^{-3}$ diluted). The data is shown in the same manner as that in (A) above (n≥8 in all genotypes). (D) A change in the mean fluorescence 10 seconds after addition of a high concentration of diacetyl ($10^{-3}$ diluted). The error bar indicates SEM ($n \geq 8$ in all genotypes).

Figure 29:
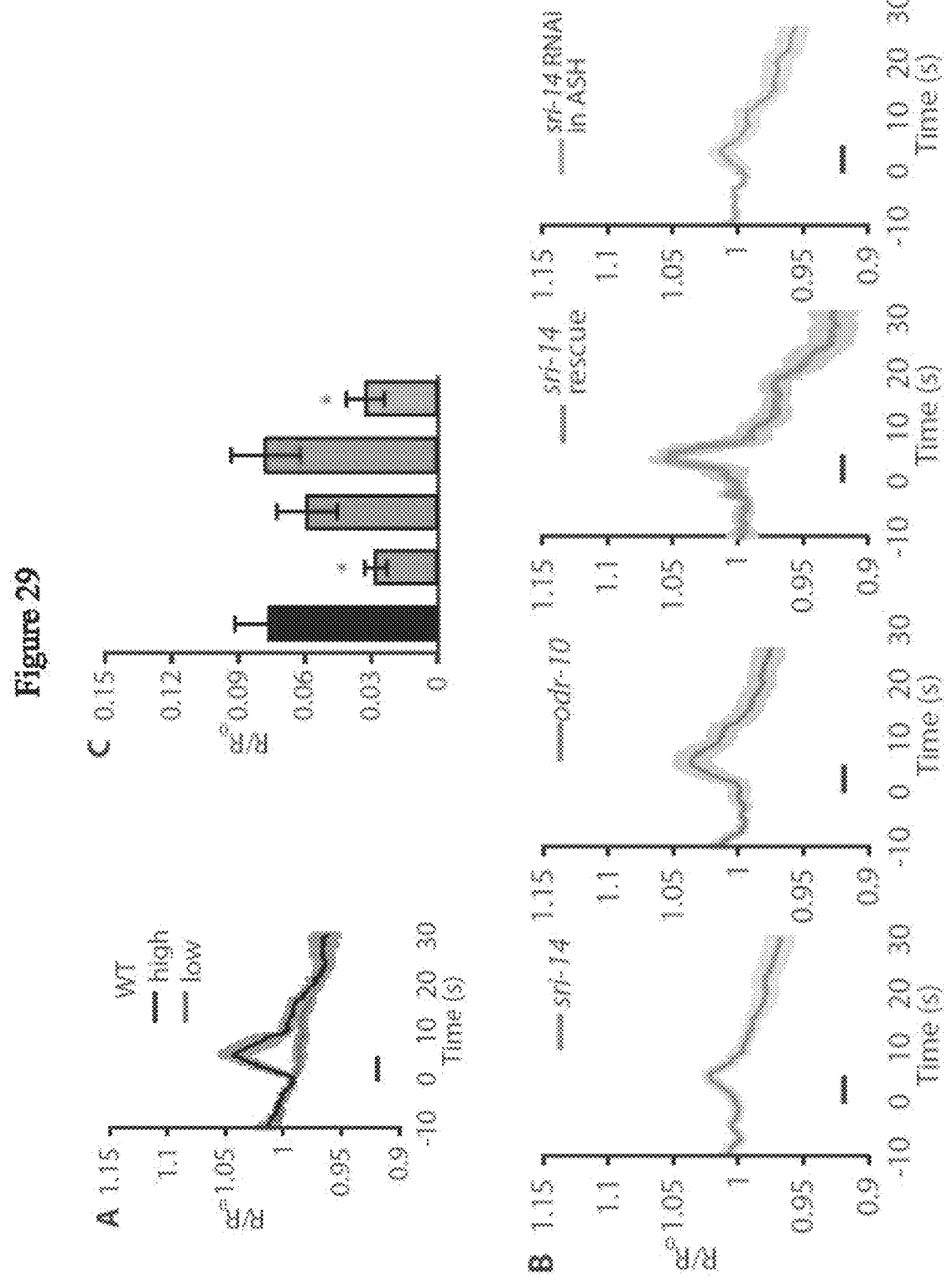

FIG. 29 is a view showing the response of ASH neurons to various diacetyl concentrations. (A) The calcium response of ASH neurons in wild-type nematodes, after stimulation by a low concentration ($10^{-5}$ diluted) of and a high concentration ($10^{-3}$ diluted) of diacetyl ($n \geq 11$). (B) The calcium response of ASH neurons in sri-14 mutants (n=26), odr-10 mutants (n=28), sri-14 mutants having the ASH-specific expression of sri-14 cDNA (sri-14 rescue, n=9), and wild-type nematodes involving the ASH-specific RNAi of sri-14 (n=20). The shaded region around the curve indicates SEM. The black bar indicates the presence of diacetyl stimulation. (C) A change in the mean fluorescence 10 seconds after addition of a high concentration of diacetyl ($10^{-3}$ diluted). The error bar indicates SEM. *P<0.05, Dunnett's test ($n \geq 11$).

Figure 30:
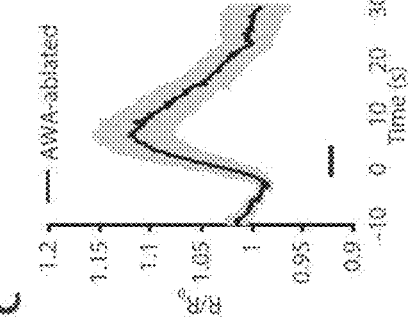
Figure 30:
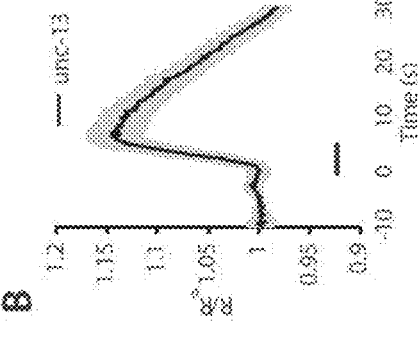
Figure 30:
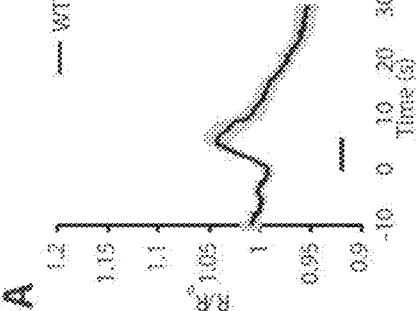

FIG. 30 is a view showing the calcium imaging of ASH neurons in unc-13 mutants and AWA-ablated nematodes. The calcium response of ASH neurons in wild-type nematodes (A, N=14), unc-13 mutants (B, N=14), and AWA-ablated nematodes (C, N=11), after stimulation by a high concentration of diacetyl ($10^{-3}$ diluted). In the case of the unc-13 mutants and the AWA-ablated nematodes, a calcium response, which has been continued for a longer period of time than in the case of wild-type nematode neurons, was observed. The shaded region around the curve indicates SEM. The black bar indicates the presence of diacetyl stimulation. (D) A change in the mean fluorescence 10 seconds after addition of a high concentration of diacetyl. The error bar indicates SEM. A significant difference from a control is shown by (*P<0.05, Dunnett's test).

Figure 31:
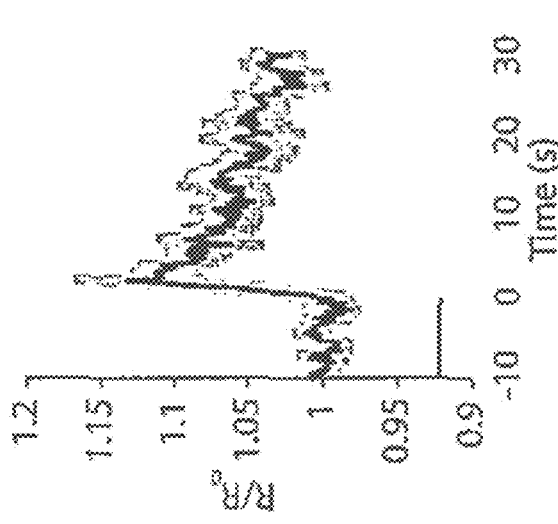

FIG. 31 is a view showing the response of AWC neurons to the removal of a high concentration of diacetyl. The calcium response of AWC neutrons in wild-type nematodes, after the removal of a high concentration of diacetyl ($10^{-3}$ diluted) (N=10). The shaded region around the curve indicates SEM. The black bar indicates the presence of diacetyl.

Figure 32:
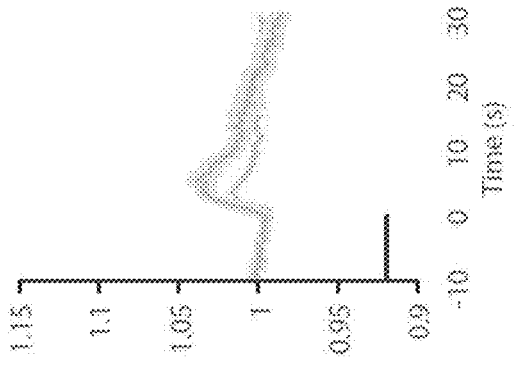
Figure 32:
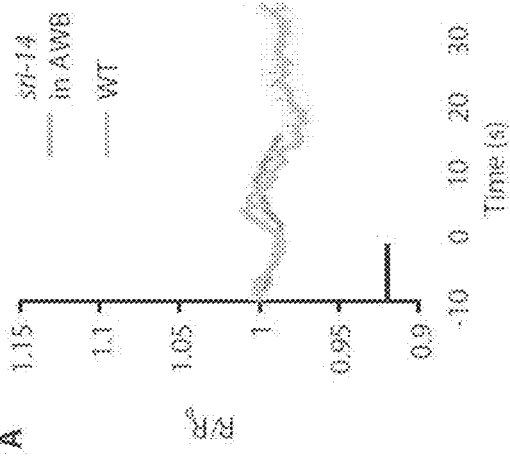
Figure 32:
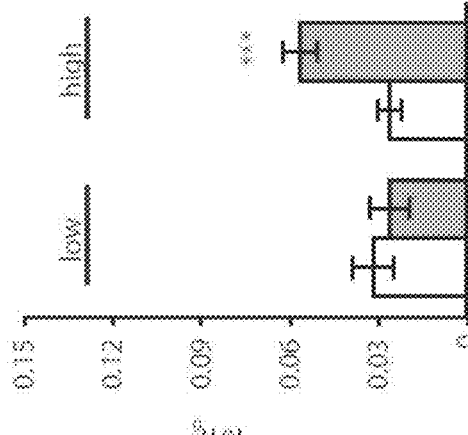

FIG. 32 is a view showing the response of AWB neurons to the removal of a high concentration of or a low concentration of diacetyl. (A) The calcium response of AWB neurons in wild-type nematodes (brown, n=10) or in nematodes in AWB neurons of which sri-14 has been ectopically expressed (orange, n=11), after the removal of a low concentration ($10^{-5}$ diluted, left) of or a high concentration ($10^{-3}$ diluted, right) of diacetyl. The shaded region around the curve indicates SEM. The black bar indicates the presence of diacetyl. (B) A change in the mean fluorescence 10 seconds after the removal of diacetyl. The white bar indicates a wild-type strain; and the orange bar indicates a strain in which sri-14 has been ectopically expressed in AWB. The error bar indicates SEM. ***P<0.001, Student's t test ($n \geq 10$).

Figure 33:
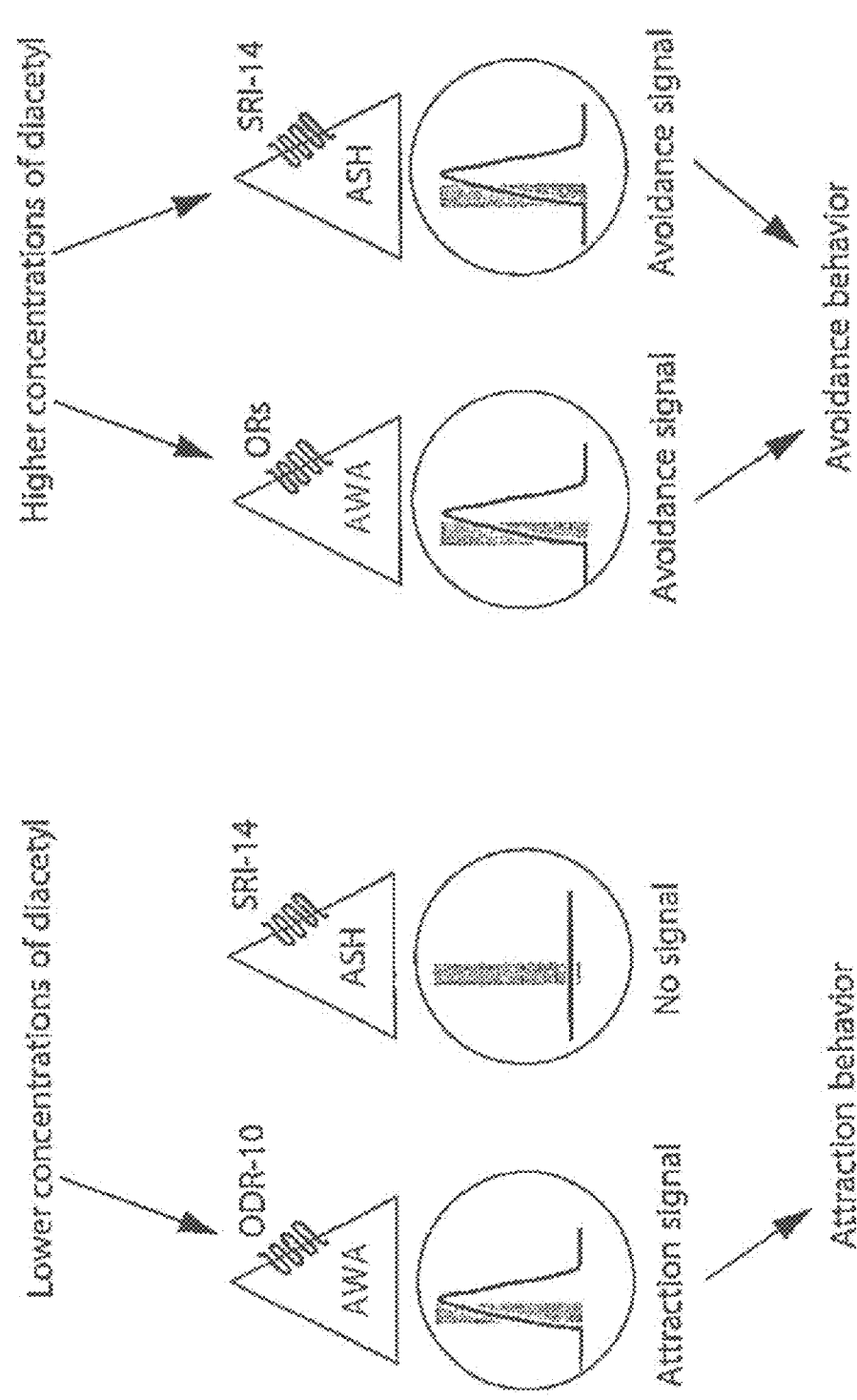

FIG. 33 is a model diagram showing the switching of an olfactory receptor, which depends on the concentration of a smell. To a lower concentration of diacetyl, not SRI-14 in the ASH neurons, but ODR-10 in the AWA neurons functions as a diacetyl receptor, and brings on activation of AWA and an attraction behavior. In contrast, a higher concentration of diacetyl is detected by SRI-14 in the ASH neurons, but is not detected by ODR-10 in the AWA neurons. ASH neurons are activated only by a higher concentration of diacetyl, and induce an avoidance behavior. AWA also responds to a higher concentration of diacetyl, indicating that olfactory receptors other than ODR-10 in the AWA neurons respond to a higher concentration of diacetyl.

Figure 34:

FIG. 34 is a view showing the chemotaxis of an N2 strain and a genetic mutant strain to the urine of patients having various types of cancers.

Figure 35:
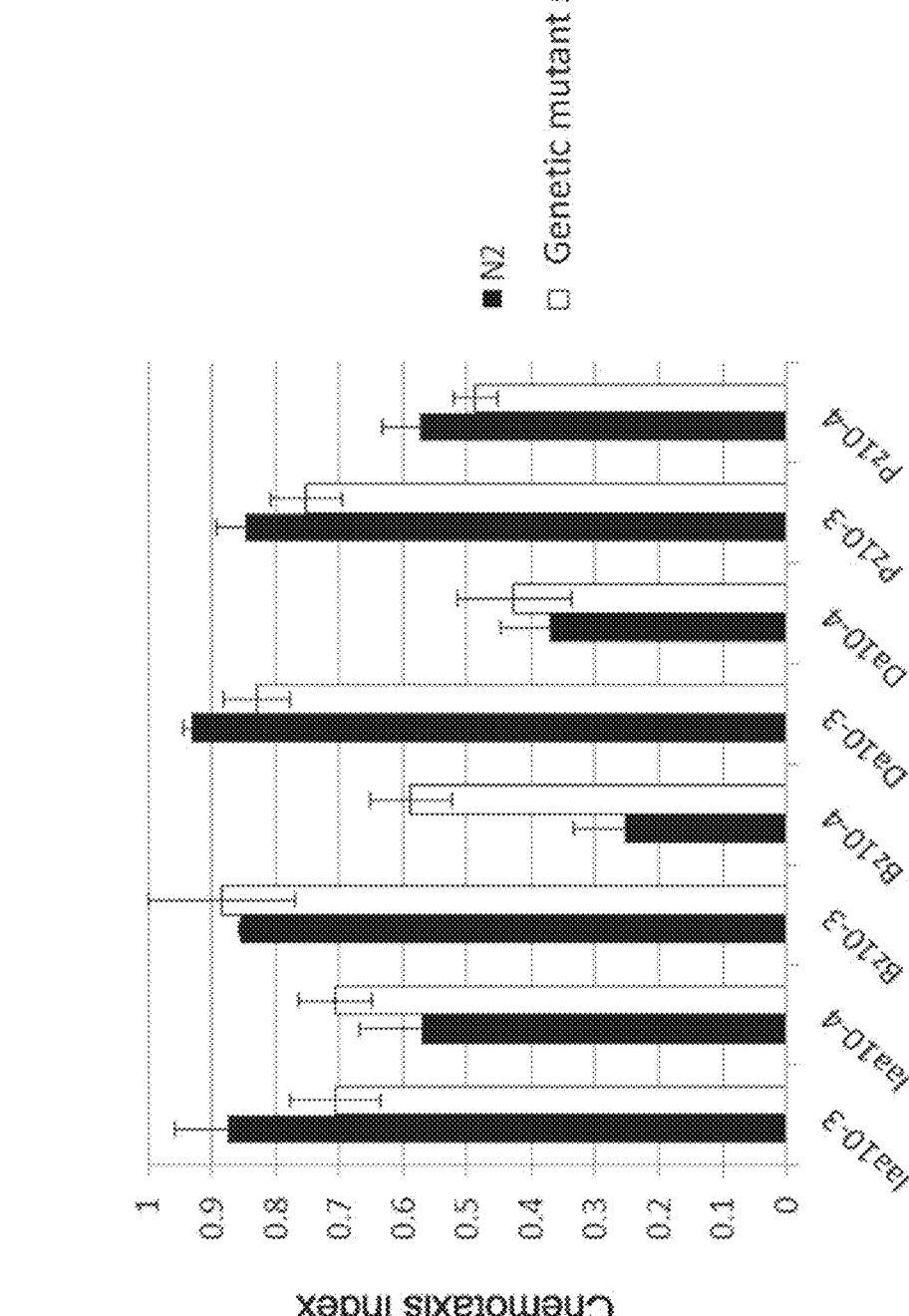

FIG. 35 is a view showing the chemotaxis of an N2 strain and a genetic mutant strain to various types of chemical substances.

Figure 36:
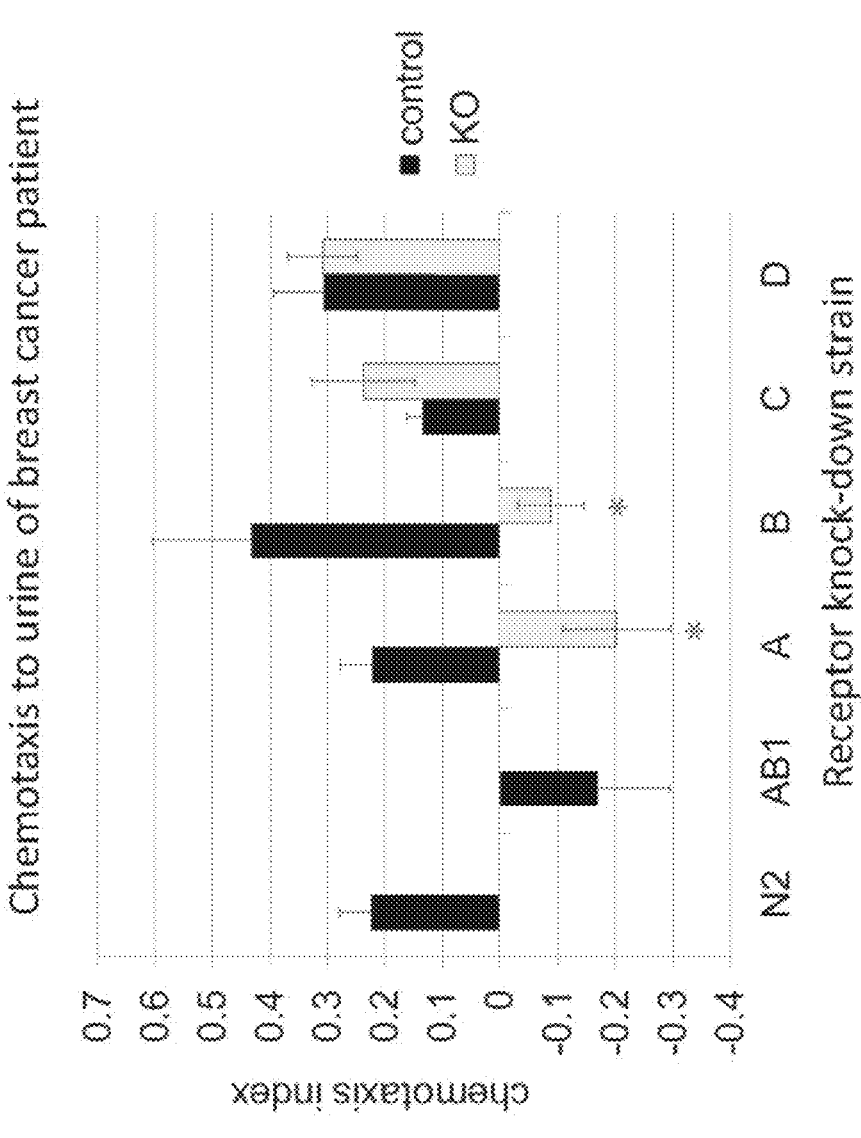

FIG. 36 is a view showing the chemotaxis of olfactory receptor knocked-down strain to the urine of breast cancer patients.

FIG. 37 is a schematic view showing a method for specifying cancer types by performing a test regarding the chemotaxis of nematodes.

EMBODIMENTS FOR CARRYING OUT THE INVENTION

Hereinafter, the present invention will be described in detail.

1. Summary

(1) Detection of Cancer

The present invention relates to a method for detecting cancer, which is characterized in breeding nematodes in the presence of a subject-derived bio-related substance or a processed product thereof, and then detecting cancer, for example, using the chemotaxis of the nematodes based on the olfaction thereof as an indicator.

Upon testing whether or not a subject has had cancer, the present inventor has focused on, in one aspect, the chemotaxis of the nematode *C. elegans* based on the olfaction thereof to a sample derived from the subject.

A nematode, *Caenorhabditis elegans* (hereinafter also abbreviated as "*C. elegans*"), is a popular organism, which has been widely bred and studied as a model organism for biological study in laboratories over the world. *Caenorhabditis elegans* is characterized in that the breeding thereof is easy and it has an excellent olfactory system.

Such nematodes exhibit a chemotaxis to an odorant, such as approaching to or escaping from it. Thus, in the present invention, using such a behavior as an indicator, the reactions of nematodes to the smells of cancers will be examined.

Figure 1:
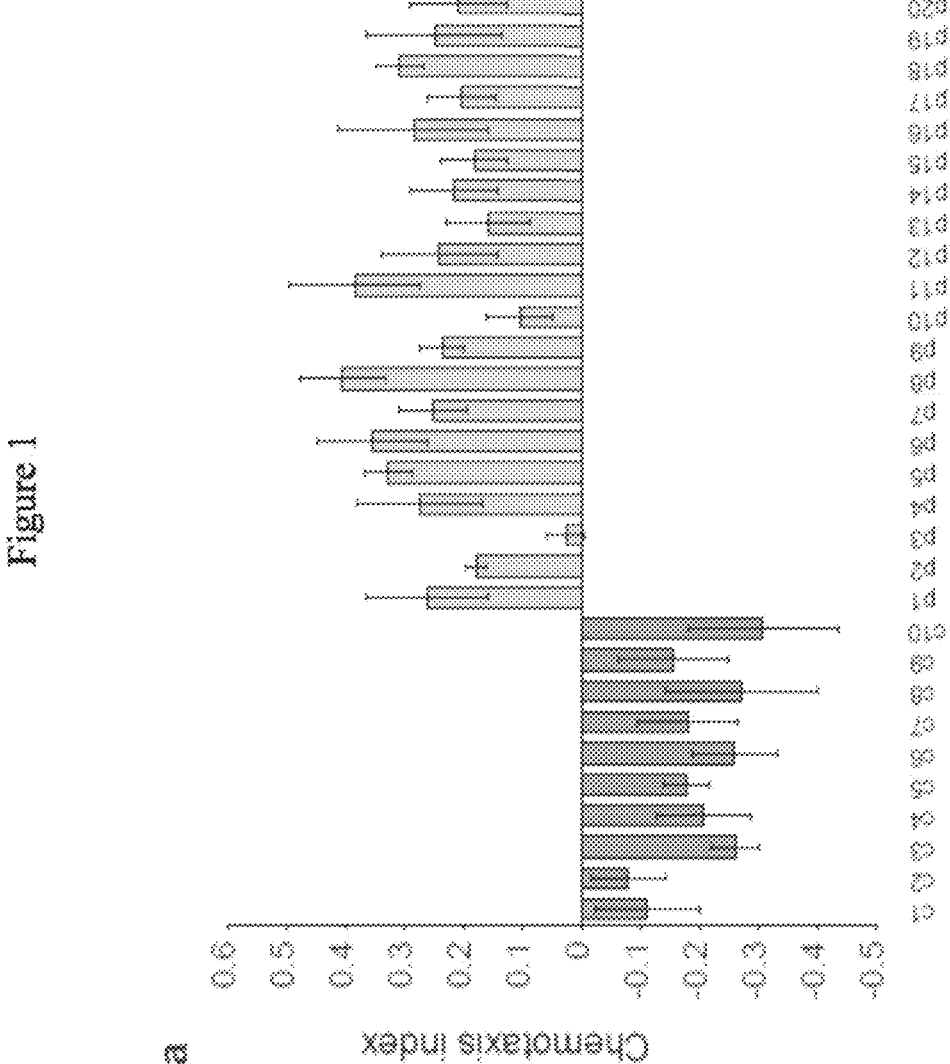
FIG. 1 is a view showing the results of the reaction test of nematodes to the urine of healthy subjects and cancer patients.

The reactions of nematodes to the urine of healthy subjects and cancer patients have been examined. As a result, the nematodes have exhibited an avoidance behavior to the urine of the healthy subjects, whereas they have exhibited an attraction behavior to the urine of the cancer patients. As a result of the examination performed on 30 specimens, the accuracy was found to be 100% (FIG. 1).

Moreover, nematodes have reacted with all of gastric cancers, colon/rectal cancers and pancreatic cancers, including early cancers. Hence, it has been demonstrated that, as with the behavior of cancer detection dogs, nematodes react with cancer-specific smells, which are common in various types of cancers.

Accordingly, in the present invention, cancer species, such as gastric cancer, colon/rectal cancer, esophageal cancer, pancreatic cancer, prostate cancer, bile duct cancer, breast cancer, malignant lymphoma, gastrointestinal stromal tumor, cecal cancer, and lung cancer, can be used as detection targets.

This cancer diagnosis system using nematodes is able to solve many problems of prior art techniques, as described below.

(i) The present cancer diagnosis system is able to detect early cancer.

Even early cancer of stage 0 or 1 can be detected with high accuracy. A specimen, which had been determined to be negative by an existing tumor marker at the time point of urine collection (2011), has been tested positive by this test. This patient has developed cancer during two years in the follow-up observation. That is to say, cancer undetectable by the existing tumor markers can be detected by the present invention.

(ii) The presence of many types of cancers can be diagnosed by a single test. That is, many types of cancers can be diagnosed by a single medical examination. To date, it has been confirmed that gastric cancer, colon/rectal cancer, esophageal cancer, pancreatic cancer, prostate cancer, bile duct cancer, breast cancer, malignant lymphoma, gastrointestinal stromal tumor, cecal cancer, and lung cancer can be detected by the present cancer diagnosis system.

(iii) The present cancer diagnosis system has high sensitivity.

In a test using 30 specimens, the present cancer diagnosis system has been able to detect cancers at sensitivity/specificity of 100%. Moreover, even in a mid-scale test (using 242 specimens), the present cancer diagnosis system has been able to detect cancers in cancer patients at a sensitivity of 100% and at a specificity of 95%.

(iv) It is easy to collect samples.

Special conditions such as dietary restriction are not determined for collection of urine samples. Urine samples collected in an ordinary, regular medical examination can be used for the analysis. Thus, subjects do not need to feel pain, and it is possible to collect samples at the same time as another urine examination. The necessary amount of urine is only several microliters ($\mu$l).

(v) The analysis can be easily carried out at low costs.

(v-1) The analysis can be carried out promptly.

It is possible to make analysis in a short time. It takes approximately 1.5 hours to analyze the chemotaxis of nematodes. It takes approximately 30 minutes to analyze the response of the olfactory neuron of transgenic nematodes.

(v-2) Inexpensiveness

For example, the present cancer diagnosis system costs as follows: for one specimen, two petri dishes for breeding nematodes (about 10 yen per petri dish), and three to five petri dishes for analyzing the chemotaxis of the nematodes (about 10 yen per petri dish). Agar costs 2.5 yen and 10 yen for each type of petri dish. Thus, the cost for one specimen is about 100 yen, including the costs of other reagents and the like. Even if personnel expenses are added to the aforementioned costs, the analysis can be carried out extremely inexpensively.

(v-3) The analysis is easy, and thus, does not require professional skills.

The chemotaxis of nematodes can be extremely easily analyzed, and thus, everybody is able to do it. In addition, the breeding of nematodes is also easy. Special training of nematodes is not necessary, and ordinarily bred nematodes can be used for the analysis.

(v-4) The analysis can be carried out on many specimens.

A single experimenter is able to carry out the chemotaxis analysis about 150 times per day. When 3 times of chemotaxes are analyzed for a single specimen, 50 specimens can be analyzed per day. It is also possible to automate this operation.

(vi) Practical application of the present cancer diagnosis system is easy, and the system can be applied over the world.

(vi-1) The system as a whole is inexpensive and can be easily applied.

The breeding of nematodes does not require a special room. The necessary apparatuses are only a 20° C. incubator and a stereoscopic microscope, and thus, the system can be constructed at low costs and in a short time.

(vi-2) The system can be applied over the world.

Since the present system does not need an expensive measurement device, it can be introduced, not only into advanced countries, but also into all countries.

(vii) The present cancer diagnosis system can be applied to the diagnosis of recurrent cancer after cancer therapy.

Since the present system is able to detect cancers in all sites, it can be applied to determination of the possibility of postoperative recurrence.

As described above, the present invention is useful as a novel, highly-accurate, cancer examination method, which gives less pain to a subject, in which operations can be easily carried out at low costs, and which can be carried out on many people as targets.

(2) Identification of Olfactory Receptors

A smell is received by an olfactory receptor on an olfactory neuron. It can be said that a human has approximately 350 types of olfactory receptors and is able to identify approximately ten thousand types of smells. How such a much smaller number of receptors are able to identify an enormous number of odorants is unknown. In order to elucidate it, it is necessary to reveal the correspondence relationship between a smell and a receptor. However, such an attempt has been carried out only partially, and as a result, the correspondence relationship, in particular, in a living animal has hardly been known.

The nematode *C. elegans* is useful for in vivo analysis, has only about 10 olfactory neurons (on the other hand, a human has about 5,000,000 olfactory neurons), and its neural circuits have all been identified. Further, the nematode *C. elegans* has almost the same mechanism of sensing a smell as that of mammals. Accordingly, *C. elegans* is considered to be a model organism for studying olfactory mechanisms. The olfactory receptors of *C. elegans* are the same 7-transmembrane G protein coupled type as that of mammals, and there are 1,200 or more predicted olfactory receptors on its genome. However, among such olfactory receptors, only one receptor (a diacetyl receptor, ODR-10) has been revealed regarding the correspondence relationship with an odorant, and how the nematode receives odor signals has been unknown.

Hence, the present inventor has been carried out comprehensive screening, in which the inventor has inhibited the function of olfactory receptor genes in living nematodes by RNAi, and has then examined how the RNAi-treated nematodes respond to 11 types of odorants. Genes involved in the response of the nematode to each smell have been picked up, and have been repeatedly analyzed. As a result, the present inventor has succeeded in obtaining candidate genes for all of the examined odorants (FIG. 22B).

Subsequently, in order to clarify whether or not the obtained candidate genes actually function as olfactory receptors in the living animal, the present inventor has focused on a phenomenon whereby the preference (likes and dislikes) to a single smell varies depending on the concentration of the smell. In the case of a human, it has been empirically known that preference to a smell is changed depending on its concentrations, and for example, a low concentration of indole causes the smell of jasmine, whereas a high concentration of indole causes the odor of feces and urine. The present inventor had elucidated in the previous studies that a similar phenomenon is observed also in nematodes, and that the type of an activating olfactory neuron changes depending on the concentration of a smell, and the preference is thereby changed (Yoshida, K. et al.: *Nature Communications* 3, 739 (2012)). Does the type of a receptor reacting to a single odorant change, depending on the odor concentration? In order to analyze this interesting question, the present inventor has focused on a sri-14 gene, which had been obtained as a gene associated with the reception of a high concentration of diacetyl. A sri-14 loss-of-function mutant has had a normal reaction to a low concentration of diacetyl, and has exhibited abnormality only in the reaction to a high concentration of diacetyl. On the other hand, in a mutant of the existing diacetyl receptor ODR-10, only the reaction to a low concentration of diacetyl has been reduced (FIG. 24A). It had already been reported that ODR-10 functions in an AWA olfactory neuron that receives a favorite smell (Sengupta, P. et al.: *Cell* 84, 899-909 (1996)). As a result of the analysis of the expression of sri-14, a rescue experiment, and a neuron-specific gene expression inhibition experiment, it has been found that SRI-14 functions in an ASH sensory neuron that receives a repulsive smell (FIG. 24). In addition, localization of SRI-14 in sensory cilia, in which olfactory receptors are present, has been observed (FIG. 24G).

Herein, examples of the gene expression inhibition experiment include: inhibition in which RNAi is utilized; inhibition in which antisense nucleic acid is utilized; and inhibition by the expression of a dominant-negative mutant gene. Among these, inhibition utilizing RNAi is preferable.

Next, using calcium imaging, the response of AWA and ASH sensory neurons to diacetyl has been observed. The AWA neuron of a wild type responded to both a low concentration of and a high concentration of diacetyl, but the AWA neuron of an odr-10 mutant did not respond to a low concentration of diacetyl (FIG. 28). The AWA neuron of a sri-14 mutant exhibited a normal response. On the other hand, the ASH sensory neuron responded only to a high concentration of diacetyl, and the response thereof was significantly reduced in a sri-14 mutant. The response was normal in an odr-10 mutant (FIG. 29). Moreover, when sri-14 was ectopically expressed in another sensory neuron AWB, which did not respond to diacetyl, AWB strongly responded to a high concentration of diacetyl (FIG. 32). Thus, it has been strongly suggested that SRI-14 functions as a diacetyl receptor in vivo. From these results, it has been found that several receptors are used to a single smell, depending on its concentrations, and that a low concentration of diacetyl is received by ODR-10 in the AWA neuron and is sensed as a favorable smell, whereas a high concentration of diacetyl is received by SRI-14 in the ASH neuron and is sensed as a repulsive smell (Taniguchi, G. et al.: *Science Signaling* 7, ra39 (2014)) (FIG. 33).

Since a nematode is an organism excellent in the olfactory system, having almost the same number of olfactory receptors as that of a dog, the nematode is likely to recognize, with high sensitivity, the smell of a harmful substance and the smell of a useful substance, as with drug-sniffing dogs. In such a case, from the results of the present study, the receptor of such a smell can be identified. If the correspondence relationship between the smell and the receptor were understood, it would be predicted that an artificial smell sensor can be developed based on the binding of the smell and the receptor as a model. An analysis of olfaction using nematodes is useful and will widely contribute to society in the future.

2. Detection Method (1) Nematode

The nematode used in the method of the present invention is one type of free-living nematode in the soil, and it has been widely used as a model organism for biological study. The nematode used in the method of the present invention is either a male or female worm, and a hermaphrodite nematode is preferable because it can proliferate as a result of self-proliferation. In addition, the nematode used in the present invention can be bred in a petri dish, giving *Escherichia coli* as foods, and thus, the breeding thereof is easy. If a parent nematode is transferred into a petri dish, larvae are born and grow up to adult worms four days later, and thus, the number of nematodes will be increased to 50 to 100 times. During such breeding, the petri dish may be placed in an incubator and may be then left as is. No special operations are needed. If a hermaphrodite nematode is used, operations such as crossing are not necessary, either. The necessary apparatuses for breeding are a 20° C. incubator and a stereoscopic microscope, and thus, the system can be established at low costs and in a short time.

An example of the nematode used in the present invention, when it is a wild-type nematode, includes *Caenorhabditis elegans*. A hermaphrodite of the *C. elegans* Briostol N2 strain is preferably used. Otherwise, genetic mutant strains including a mutation of various genes can also be used. These nematodes are available, for example, from Caenorhabditis Genetic Center (CGC).

In the present invention, in addition to the aforementioned nematodes (wild-type nematodes), mutant nematodes and transgenic nematodes can also be used. Examples of the transgenic nematode include: a nematode, in which an indicator gene has been introduced into the olfactory neurons AWC and AWA; a nematode, in which the expression or function of a gene associated with the reception of the smell of cancer (receptor gene) has been inhibited; a nematode, in which a gene associated with the reception of the smell of cancer (receptor gene) has been over expressed or high-functionalized; and a nematode, in each cell of which a fluorescent protein has been expressed to facilitate the analysis of the behavior thereof. However, the examples of the transgenic nematode are not limited thereto, and all of transgenic strains, into which a foreign gene has been introduced, can be used.

In the present invention, DNA, in which a gene of interest is ligated immediately downstream of a predetermined promoter of a nematode, is constructed, and the obtained DNA is then microinjected into a wild-type nematode strain or a genetically mutated nematode strain (e.g., gonad). Thereby, a transgenic nematode capable of stably passaging the foreign gene can be produced. An increase in the calcium concentration indicates activation of neurons. Thus, for example, an indicator gene capable of measuring a calcium concentration in the neuron is used, and cancer can be detected using a change in the calcium concentration as an indicator.

An example of the promoter used for expression in AWC includes an odr-1 promoter (Yu, S., Avery, L., Baude, E. & Garbers, D. L. Guanylyl cyclase expression in specific sensory neurons: a new family of chemosensory receptors. *Proc Natl Acad Sci USA* 94, 3384-3387 (1997).). The odr-1 induces the expression of in AWC and in AWB (which is another olfactory neuron other than AWC).

An example of the promoter used for expression in AWA includes an odr-10 promoter (Sengupta, P., Chou, J. H. & Bargmann, C. I. odr-10 encodes a seven transmembrane domain olfactory receptor required for responses to the odorant diacetyl. *Cell* 84, 899-909 (1996).). The odr-10 has been known to induce the expression only in AWA.

The base sequence information regarding these promoters can be obtained, for example, from Accession Nos. Z68118 and FO080931. Alternatively, it is also possible to obtain such a promoter by purifying the genomic DNA of a nematode, and then performing PCR amplification using the genomic DNA as a template.

Examples of the calcium indicator gene include: a Yellow Cameleon (YC) gene (Nagai, T., Yamada, S., Tominaga, T., Ichikawa, M. & Miyawaki, A. Expanded dynamic range of fluorescent indicators for Ca(2+) by circularly permuted yellow fluorescent proteins. *Proc Natl Acad Sci USA* 101, 10554-10559 (2004).); and a GCaMP gene (Nakai, J., Ohkura, M. & Imoto, K. A high signal-to-noise Ca2+ probe composed of a single green fluorescent protein. Nat. Biotechnol. 19, 137-141 (2001).). The base sequence information regarding these genes is available, for example, from Accession Nos. AB178712 and HM143847. Alternatively, these genes can also be obtained from Addgene.

The method of ligating an indicator gene immediately downstream of a promoter, the microinjection method and the like are well known in the present technical field, and for example, "Molecular Cloning: A Laboratory Manual (4th Edition)" (Cold Spring Harbor Laboratory Press (2012)), etc. may be referred to. Alternatively, a DNA solution can be injected into the gonad of a nematode according to a known method (Mello, C. C., Kramer, J. M., Stinchcomb, D.& Ambros, V. Efficient gene transfer in *C. elegans*: extrachromosomal maintenance and integration of transforming sequences. EMBO J 10, 3959-3970 (1991).).

Mutant nematode is used to mean, for example, a nematode comprising a polymorphism in the genome of a wild-type nematode, a mutant nematode comprising a mutation of an olfactory receptor for the smell of each cancer species, etc. (which will be described in Examples later).

(2) Subject-Derived Bio-Related Substance or Processed Product Thereof

The sample used in the present invention is a bio-related substance derived from a subject (a healthy subject, a cancer patient, a patient suspected of having cancer, an animal, etc.). The term "bio-related substance" is used to mean a biological sample collected from a subject, and examples of such a bio-related substance include a body fluid (urine, sweat, saliva, or feces fluid), cells (cells obtained from biopsy, etc.), cancer tissues (tissues obtained from biopsy, tissue sections, etc.), blood, and expiration. In the present invention, these biological samples can be directly used. However, a processed product of such a bio-related substance is preferably used. The term "processed product" is used to mean a sample obtained by physically and/or chemically processing a bio-related substance.

Figure 9:
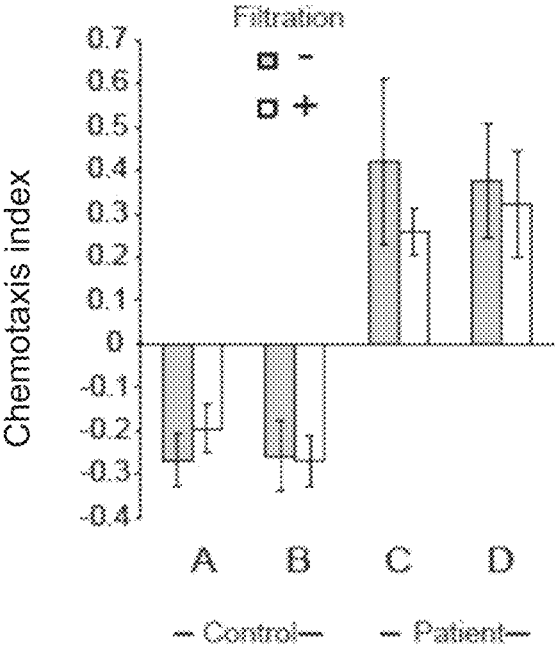
FIG. 9 is a view showing the results obtained by examining the chemotaxis of nematodes, using a urine sample from which precipitates and solids have been removed.

The body fluid sample such as urine includes a solid and a precipitate. In the case of urine, for example, the collected urine can be directly used. However, since the urine sample needs to be given to a nematode through a narrow tube, it is preferably subjected to a filter removal treatment (for example, pore size: 0.22 μm, Millex GP, Merck Millipore). A urine sample, which has been subjected to a solid removal treatment using such a filter, is included in the above-described "processed product." It is to be noted that the present inventor has confirmed by a preliminary experiment that the reaction of a nematode (attraction behavior to urine) is not changed by such a filter treatment (FIG. 9).

As described above, when cells (e.g., cancer cells obtained from biopsy) are used as a bio-related substance, a solid such as a cell disintegrated product is removed from a culture obtained after cell culture according to centrifugation, filtering or the like, and a culture supernatant obtained after the removal of the solid can be used as a processed product.

Moreover, in the present invention, in addition to the aforementioned samples, a preservative solution of cancer cells or cancer tissues (tissues obtained from biopsy, tissue sections, etc.) can also be used. Examples of such a preservative solution include a physiologic saline, a buffer, formalin, and DMSO, but the examples are not limited thereto. The preservative solution includes a preservative solution for cryopreservation, which is commonly used for cryopreservation. After the cryopreservation, such a preservative solution for cryopreservation can be used by thawing it.

(3) Detection Utilizing Nematode Scent

First, to obtain nematodes necessary for detection, they are allowed to proliferate.

Several nematodes (adult worms) are placed in a petri dish (containing an NGM medium on which *Escherichia coli* has been dispersed), and thereafter, they are bred for 3 to 6 days, preferably for 4 days, and at a temperature of 15° C. to 25° C., preferably at 20° C. Thereby, approximately 300 to 500 next-generation nematodes grow up to adult worms.

Figure 2:
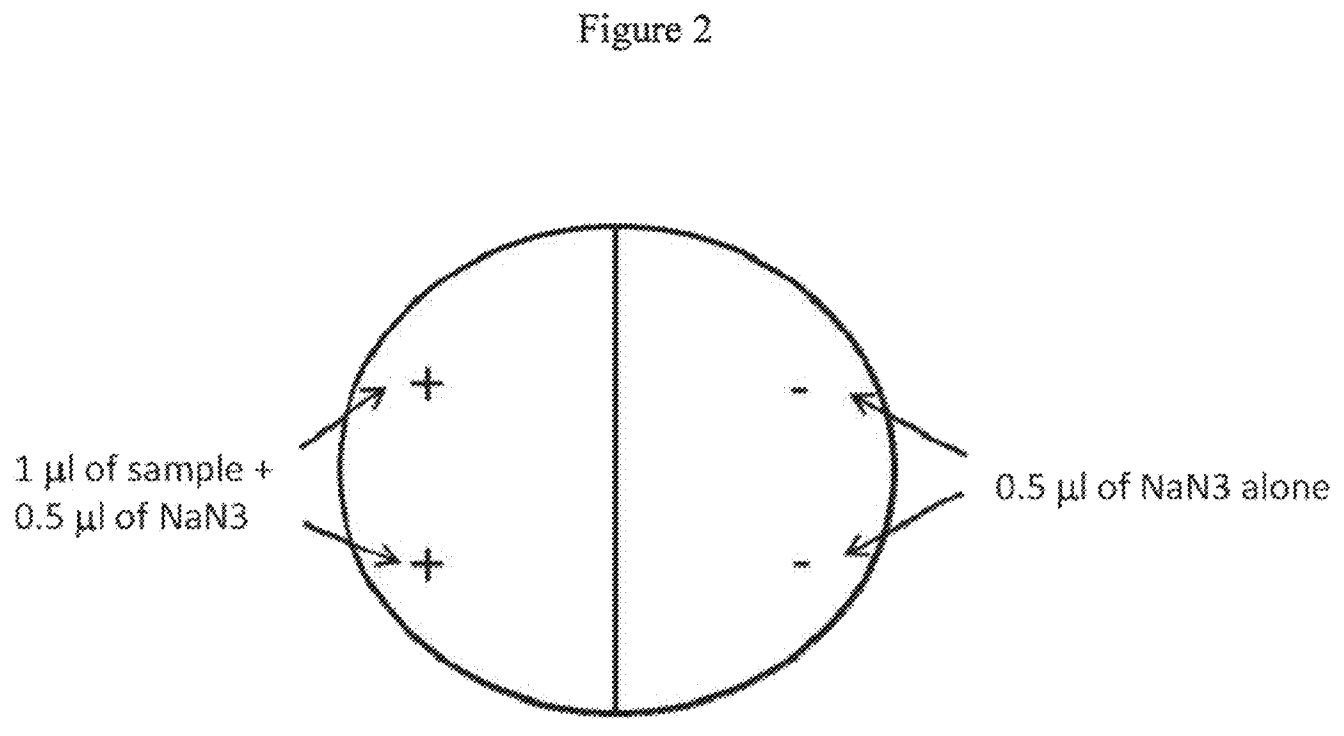

Subsequently, a petri dish used for an actual test is prepared. A format as shown in FIG. 2 is produced in a petri dish, and sodium azide (NaN$_3$) is then placed in (added to) 4 points in the petri dish. Sodium azide is used to anesthetize and immobilize nematodes. The amount of sodium azide added is 0.2 to 3 μl, and preferably 0.5 μl, at a concentration of 1 M.

The *Escherichia coli* dispersed on the petri dish is removed with a washing buffer, and thereafter, a bio-related substance or a processed product thereof, used as a sample, is placed on (added to) the petri dish. When urine is used as a sample, a stock solution of the urine sample can be used. However, the collected urine may be diluted to 1.5 to 1000 times, for example, with sterilized water, a buffer, etc. The dilution magnification is preferably 10 times. The amount of the urine sample added to the petri dish is 0.5 to 10 μl, and preferably 1 μl.

Nematodes are placed on the center of the thus prepared petri dish.

The nematodes are bred (allowed to swim) for a predetermined period of time (approximately 1 hour). Room temperature: is set at 23° C.±1° C.

After the predetermined period of time has passed, the number of nematodes on the + side and the number of nematodes on the − side are counted, and the chemotaxis index (the following formula) is then calculated. When the number of nematodes on the + side is represented by N(+) and the number of nematodes on the − side is represented by N(−), the following formula holds:

Chemotaxis index=$N$(+)−$N$(−)/total number of nematodes.

Thereafter, using the positive response or the negative response as an indicator, cancer is detected.

The term "positive response" is used to mean that the nematodes "like" or "are interested in" the sample, whereas the term "negative response" is used to mean that the nematodes "dislike" or "are not interested in" the sample.

When the chemotaxis is used as an indicator, the positive value (+) indicates a positive response (positive chemotaxis, like), and the negative value (−) indicates a negative response (negative chemotaxis, dislike).

The chemotaxis index has the values from +1 to −1. When the nematodes are attracted to the sample, the chemotaxis index has a plus value, and when the nematodes avoid the sample, the chemotaxis index has a minus value.

A single analysis may be performed on a single specimen. However, a plurality of analyses can be performed on a single specimen, and a mean value of the chemotaxis index values is calculated, so that the accuracy of the obtained value can be enhanced. When the value obtained by the analysis (which is a mean value when a plurality of analyses have been performed) is a plus value, it can be preliminarily or definitely determined that the subject has cancer, or has cancer risk (possibility). The determination that the subject "has cancer" can be used, for example, as a support documentation for the definite diagnosis or preliminary diagnosis of cancer, and the determination that the subject "has cancer risk" can be used, for example, as a support documentation for suspecting cancer in a medical examination, a first examination of cancer, etc.

The reaction of a nematode to a smell can also be detected using a behavior other than the chemotaxis, or a biological reaction, as an indicator. Examples of the behavior other than the chemotaxis or the biological reaction include: a weathervane behavior (Iino & Yoshida, The Journal of Neuroscience, 2009), by which a nematode turns to a direction in which the concentration of a smell is high; a turning behavior (Pierce-Shimomura et al., The Journal of Neuroscience, 1999), which takes place when the concentration of a smell becomes low; the bending degree of the nematode body (Luo et al., Journal of Neurophysiology, 2008); and neural response.

With regard to the weathervane behavior, the "positive response" means that a nematode turns to the direction of a sample. With regard to the turning behavior, when a nematode turns at the time in which a high concentration of sample is changed to a low concentration of sample, it can be said that the nematode has a "negative response." In the case of the bending degree of the body, when the distance between the head portion of a nematode and the tail portion thereof is long, it can be said that the nematode has a "positive response."

(4) Detection Utilizing Genetically Modified Nematodes (i) Detection utilizing genetically modified nematodes can also be carried out as described above. Herein, a transgenic nematode, in which an indicator gene capable of measuring a calcium concentration in the neuron has been expressed in the olfactory neurons AWC and AWA of a nematode, is used, and cancer is detected using a change in the calcium concentration (neural response) as an indicator. Since this method is able to make analysis using several nematodes, it is advantageous in that the cost for the culture of nematodes can be saved, and in that the analysis can be carried out in a short time.

Figure 3:
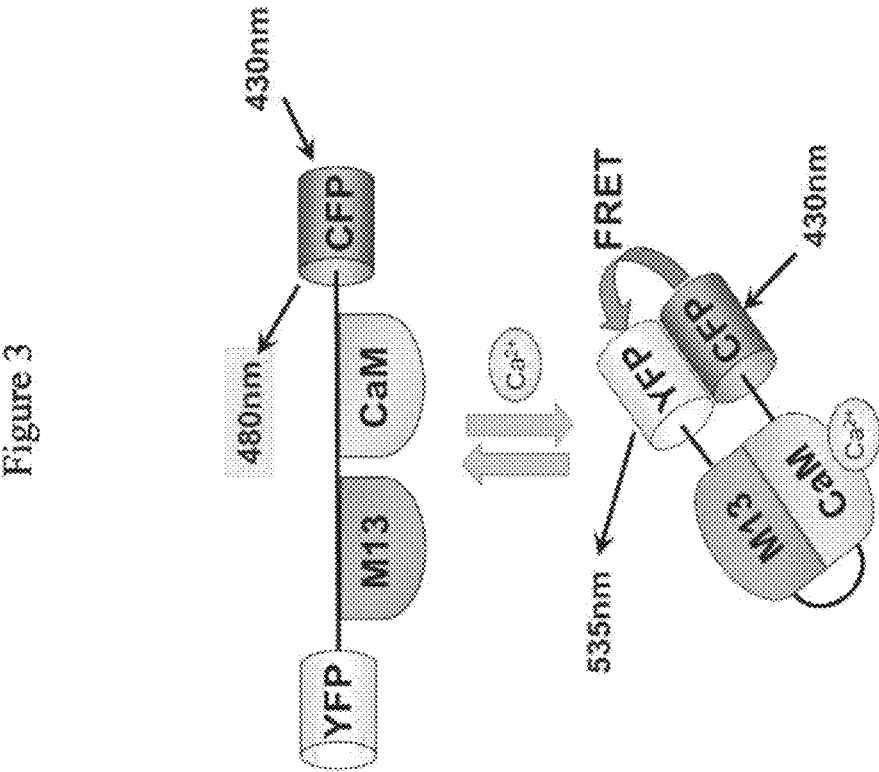
FIG. 3 is a view showing a measurement principle when a Yellow Cameleon gene is used as an indicator gene.

A measurement principle when using a Yellow Cameleon gene as an indicator gene is shown in FIG. 3.

The indicator protein used in the measurement is a fusion protein formed by connecting the calcium-binding protein CaM with the target domain M13, to which the CaM binds, and then connecting CFP and YFP with both ends thereof (which is encoded by the gene, and thus can be genetically expressed in vivo). When the calcium concentration is low, CaM is separated from M13, and CFP is also positioned apart from YFP (left view). Thus, if light for excitation of CFP is given, blue light is emitted from the CFP. On the other hand, when the calcium concentration becomes high so that CaM binds to M13, CFP approaches to YFP, and fluorescence resonance energy transfer (or Forster resonance energy transfer) (FRET) occurs between them. As a result, even if light for excitation of CFP is given, yellow light is emitted from the YFP (right view). As such, the intensity of the blue light and the yellow light is simultaneously measured, and the ratio therebetween is then calculated, so that a change in the calcium concentration can be found.

Figure 4:
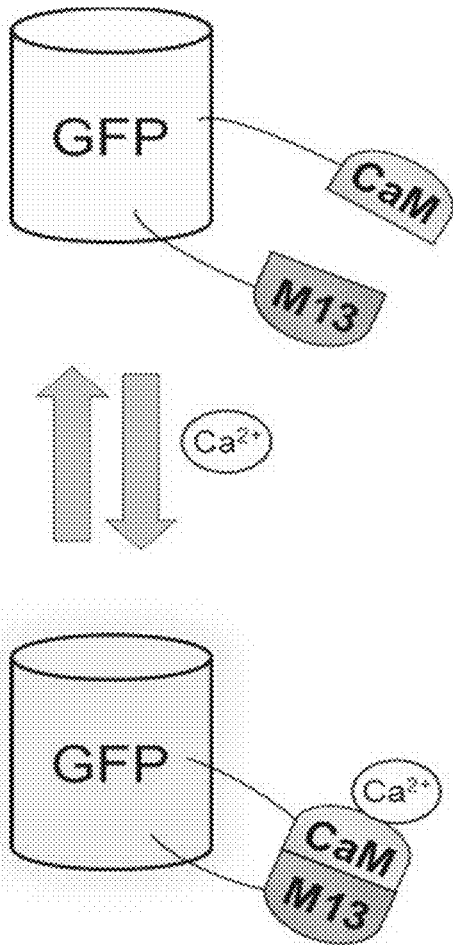
FIG. 4 is a view showing a measurement principle when a GCaMP gene is used as an indicator gene.

A measurement principle when using a GCaMP gene as an indicator gene is shown in FIG. 4.

The indicator protein is a fusion protein having a structure in which CaM and M13 are allowed to bind to GFP. This protein is also encoded by the gene, and thus, it can be genetically expressed in vivo. When the calcium concentration is increased and M13 binds to CaM, the fluorescence intensity of GFP increases. Thus, by measuring the fluorescence of GFP, a change in the calcium concentration can be found.

In the present invention, when the response of the olfactory neuron of a nematode is high to a subject-derived bio-related substance or a processed product thereof, namely, when a change in calcium concentration is high, the subject is determined to have cancer, or to have cancer risk. Herein, the term "when . . . is high" in the phrases "the response of the olfactory neuron . . . is high" and "a change in the calcium concentration is high" means that when the subject-derived bio-related substance or a processed product thereof is given as a stimulus, a change in the fluorescence intensity ratio (ratio=YFP/CFP) or a change in the fluorescence intensity of GFP is significantly large, in comparison to a control (a healthy subject-derived bio-related substance or a processed product thereof).

Figure 5:
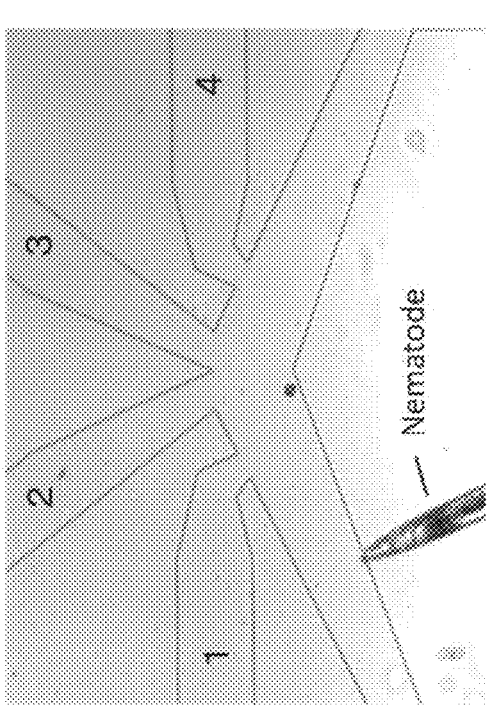
FIG. 5 is a view showing a chip having a micro flow channel, in which for a nematode is disposed.

(ii) An individual nematode, in which a calcium indicator has been expressed in the olfactory neuron, is placed in a chip made of resin (e.g., made of dimethylpolysiloxane (PDMS) resin) (FIG. 5). In FIG. 5, a portion for holding the nematode and four flow channels are formed in the PDMS resin-made chip.

By switching the flow channels 1 to 4 using a reflux apparatus (manufactured by WPI, Multi Channel Perfusion System MPS-2, etc.) (FIG. 6), the ON or OFF of urine stimulation is performed (Chalasani, S. H. et al. Dissecting a circuit for olfactory behaviour in *Caenorhabditis elegans. Nature* 450, 63-70 (2007); Chronis, N., Zimmer, M. & Bargmann, C. I. Microfluidics for in vivo imaging of neuronal and behavioral activity in *Caenorhabditis elegans. Nat Methods* 4, 727-731 (2007).).

Figure 6:
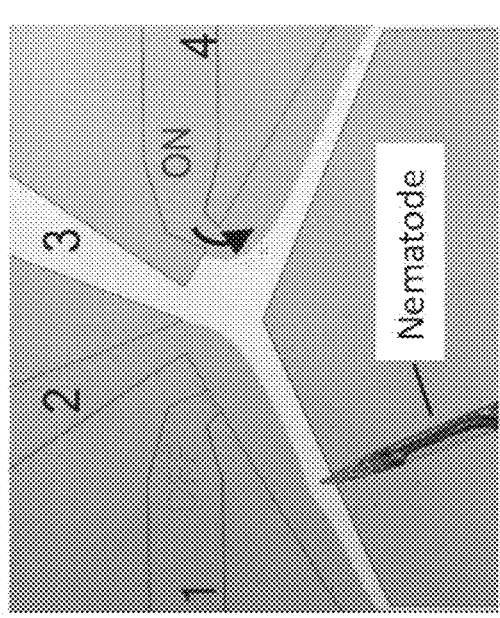
FIG. 6 is a view showing the switching of flow channels in a chip having micro flow channels.
Figure 6:
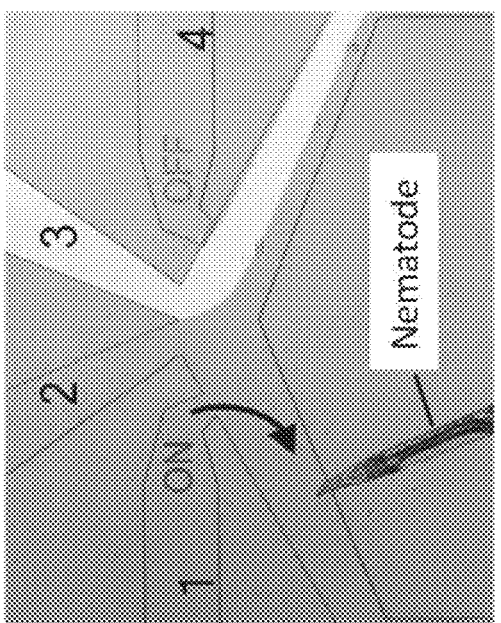

FIG. 6 is a view showing the switching of the flow channels in a chip. A buffer has been placed in the flow channels 1, 2 and 4, and urine has been placed in the flow channel 3. The flow channels 2 and 3 are constantly kept in the "ON" position. When the flow channel 1 is "ON" and the flow channel 4 is "OFF," the nematode does not receive urine stimulation. When the flow channel 1 is turned to "OFF" and the flow channel 4 is turned to "ON," the nematode receives urine stimulation.

Since the AWC olfactory neuron is reactive when "there is a smell"→"there is no smell" (odor-OFF reaction), the reaction of the nematode is observed when a condition with urine is changed to a condition without urine. In contrast, in the case of the AWA neuron, since the AWA neuron is reactive to "there is no smell"→"there is a smell" (odor-ON reaction), the reaction of the nematode is observed when a condition without urine is changed to a condition with urine.

By the way, the olfactory neuron of a nematode is weakly reactive even with the urine of a healthy subject. Thus, the urine of a control (the urine of a healthy subject) is prepared, and the control urine and urine as a specimen are successively given to a single nematode, so that cancer can be preferably detected based on a difference in the reaction strength.

(iii) Using a fluorescence microscope (Leica DMI3000B, etc.), a fluorescence image is obtained with objective lens (40-fold). Such an image is obtained, for example, at every 200 ms, but it can be changed, as appropriate, depending on the type of a microscope or lens. In the case of Yellow Cameleon, images at two wavelengths need to be obtained, separately. Thus, a camera capable of simultaneously obtaining such images at two wavelengths, for example, ORCA-D2 digital camera (Hamamatsu Photonics) is preferably used (however, other than this camera, cameras having similar functions have been commercially available). In the case of GCaMP, it is sufficient to obtain an image at one wavelength. Thus, a common microscopic camera capable of obtaining a GFP image may be used.

(iv) With regard to the obtained image, the cell body of an olfactory neuron (a site in which a change is most visible) is enclosed as ROI (region of interest), and for the fluorescence intensity of each pixel, all calculations and video production are carried out using software (e.g., Metamorph software, manufactured by Molecular devices). Other software products sold by various companies are also available. In the case of Yellow Cameleon, the YFP/CFP ratio is calculated for each pixel, and a mean value in the ROI is then calculated. In addition, in the case of GCaMP, a mean value of fluorescence intensity in the ROI is calculated.

3. Identification of Receptor

The present invention provides a method for identifying a olfactory receptor in a nematode, which is characterized by identifying the olfactory receptor using the nematode.

The identification method of the present invention comprises a step of inhibiting the expression or function of a gene encoding a receptor, and testing the reaction of the inhibited nematode to a smell.

As described above, examples of the inhibition of the expression or function of an olfactory receptor gene include inhibition in which RNAi is utilized, inhibition in which antisense nucleic acid is utilized, and inhibition by the expression of a dominant-negative mutant gene. Among these, inhibition utilizing RNAi is preferable.

Using nematodes, in which the expression of the receptor gene has been inhibited, the reaction to the smells of samples derived from various types of cancers is tested. When the nematodes are not reactive to the smell of a certain cancer type, the receptor can be determined to be a receptor to the smell of the cancer type.

The type of a receptor to be identified is different depending on the concentration of an odorant. Accordingly, to which sample concentration nematodes are reactive is tested, so that a receptor to a high concentration of sample and a receptor to a low concentration of sample can be identified.

The olfactory system detects various odorants and responds thereto. The olfactory receptor is a G protein (heterotrimeric guanine nucleotide-binding protein)-coupled receptor in a majority of organisms, and it directly binds to a volatile or soluble odorant. When compared with the genome of a mammal, the genome of the nematode *Caenorhabditis elegans* (*C. elegans*) comprises a larger number of putative olfactory receptor genes, and this suggests that combinatorial complexity can be present with regard to the relationship between a receptor and a smell in nematodes. In order to identify the olfactory receptor of a nematode necessary for the response to a specific odorant, the present inventor has conducted RNA interference (RNAi) screening. As a result of this screening, the present inventor has identified 194 candidate olfactory receptor genes, which are associated with 11 odorants. Moreover, the present inventor has also identified SRI-14 as a candidate gene associated with detection of a high concentration of diacetyl. As a result of rescue and neuron-specific RNAi experiments, the inventor has demonstrated that SRI-14 functions in specific chemosensory neurons, ASH neurons (the sensory neuron of a nematode that receives repulsive smells or chemical substances) and provides an avoidance response. According to calcium imaging, it has been demonstrated that the ASH neurons respond only to a high concentration of diacetyl, whereas another type of chemosensory neurons, AWA neurons (the olfactory neuron of a nematode that mainly receives favorite smells) respond to both a low concentration of and a high concentration of diacetyl. The loss of the function of SRI-14 has prevented ASH from responding to a high concentration of diacetyl, whereas the loss of the function of ODR-10 has reduced the response of AWA to a lower concentration of diacetyl. Chemosensory neurons, in which SPI-14 is ectopically expressed, have responded to a high concentration of diacetyl. Accordingly, the nematode has a concentration-dependent odor sensing mechanism, which is classified based on an olfactory receptor level and a sensory neuron level.

In general, animals detect various odorants through their olfactory system and respond thereto. A majority of odorants are volatile compounds, and are detected by olfactory receptor neurons (ORN). In the ORN, an odorant directly binds to an olfactory receptor, and thereafter, transmits information via an intracellular signaling pathway (1). In mammals, the olfactory receptor is a member of the 7-transmembrane G protein (heterotrimeric guanine nucleotide-binding protein)-coupled receptor (GPCR) family (2), and only one olfactory receptor type is present in individual ORN (3). However, although various types of studies have been conducted for the purpose of identifying the correspondence relationship between a smell and a receptor, the relationship between individual smells and receptors has remained almost unknown (4, 5). Taste (gustatory sense (gestation)) has a similar process, but the taste is associated with detection of soluble chemical substances.

The nematode *Caenorhabditis elegans* is a model organism used in the analysis of chemosensory processes associated with smell and taste (olfaction, detection of volatile signals; and taste, detection of soluble signals), and *C. elegans* detects a large number of chemical cues through approximately 13 sensory neurons thereof, which have been known to respond to chemical substances, and then responds thereto (6, 7). For convenience, the present inventor refers to this chemosensory process as olfactory sense, and chemical substances as odorants. The genome of the nematode (*C. elegans*) is predicted to comprise more than 1200 putative olfactory receptor genes encoding GPCR, and the GPCR is expressed in 11 chemosensory neurons (8). These findings have indicated that multiple types of olfactory receptors (9) are likely to be expressed in individual ORNs, which are different from olfaction (3), but are similar to taste perception (10) in mammals. However, the relationship between a receptor and an odorant or another chemical substance has been identified only for a diacetyl-specific receptor, ODR-10 (11), and a pheromone receptor (which is also GPCR (12-14)). How an odorant is detected by such a combination of a receptor in the ORN of the nematode (*C. elegans*) has been unknown.

As with many types of animals, the nematode (*C. elegans*) also exhibits preference to specific odorants. When such a specific odorant is detected by the AWA or AWC olfactory neurons, the nematode exhibits an attraction behavior to the odorant. When the odorant is detected by the AWB, ASH or ADL sensory neurons, the nematode exhibits an avoidance behavior (6, 15, 16). However, some types of neurons are associated with both the avoidance behavior and the attraction behavior, and an example of such neurons is AWB neurons (16). So far, the present inventors had demonstrated that the attraction response or avoidance response of the nematode (C. elegans) to a single odorant depends on the concentration of the odorant (17). This suggests that different olfactory receptors are likely to function even on a single odorant, depending on the concentration of the odorant.

Herein, the present inventor has demonstrated that different concentrations of diacetyl substances are mediated by different olfactory receptors, and that preference is thereby changed. As a result of the screening of smell-receptor pairs, the present inventor has identified 194 candidate olfactory receptor genes with respect to 11 odorants. Among these candidate genes, the present inventor has identified SRI-14 as a gene that specifically responds to a high concentration of diacetyl. The results obtained by the present inventor have demonstrated that, with regard to reception of diacetyl, ODR-10 in the AWA neurons mediates an attraction response to a low concentration, and SRI-14 in the ASH neurons mediates an avoidance response to a high concentration.

4. Specification of Cancer Types

In the present invention, it becomes possible to specify cancer types according to a nematode chemotaxis test. Accordingly, the present invention provides a method for identifying cancer species, which is characterized by identifying cancer species, using the reaction of a nematode to the smell of a subject-derived bio-related substance or a processed product thereof as an indicator.

As a result of studies regarding cancer detection dogs, it has been predicted that each cancer type has a different smell. Hence, the olfactory receptor of a nematode to the smell of each cancer type is identified, and the receptor is then modified to produce a modified nematode. Examples of such modified nematodes include a strain comprising a mutation or deletion of a receptor gene, a strain wherein the expression or function of a receptor gene is inhibited, and a strain wherein a receptor gene is highly expressed or high-functionalized.

An example of a method of producing a deletion mutant includes a CRISPR/Cas9 method (Friedland et al, Heritable genome editing in C. elegans via a CRISPR-Cas9 system, Nature Methods, 2013). Moreover, a strain wherein the expression or function of a receptor gene is inhibited or a modified nematode wherein a receptor gene is highly expressed or high-functionalized is also produced. Examples of inhibition of the expression or function include: inhibition in which RNAi is utilized; inhibition in which antisense nucleic acid is utilized; and inhibition by the expression of a dominant-negative mutant gene. Examples of a method of high expressing or high-functioning a receptor gene include: a method of connecting the promoter of a receptor gene with a tandem; a method of introducing an enhancer; a method involving introduction of multiple copies of a receptor gene; a method of modifying the binding site of a receptor with a smell or a G protein; and a method of modifying a site for controlling the activation or localization of a receptor or affinity for a smell.

The identification method of the present invention comprises, for example, the following steps.

(a) First, as STEP 1, cancer is detected by the above-described detection method of the present invention. For example, using the N2 strain, the presence or absence of cancer species is tested.

(b) Next, as STEP 2, using a mutant of the receptor of each cancer type, or a strain in which the expression or function of a receptor gene has been changed, the cancer type is specified.

Using a mutant nematode comprising a mutation or deletion of the above identified olfactory receptor, or a strain in which the expression or function of a receptor gene has been changed, the reaction of such a nematode to the smell of a sample, in which cancer has been detected in the above-described step (a), is tested.

(c) When the reaction to the smell is different between the above-described modified nematode and the nematode used in the above-described step (a), the cancer type corresponding to the identified receptor is determined to be cancer type as a target of the identification.

For example, among the above-described mutant nematodes and the nematodes in which the expression or function of a receptor gene has been inhibited, the cancer type corresponding to the receptor identified in nematodes, which have not reacted to the smell, is determined to be cancer type as a target of the identification. Alternatively, among the nematodes in which a receptor gene has been highly expressed or high-functioned, the cancer type corresponding to the receptor identified in nematodes, whose reaction to the smell has been accelerated, is determined to be cancer type as a target of the identification.

For example, when a receptor mutant regarding the smell of large bowel cancer does not exhibit an attraction behavior, having large bowel cancer can be determined (diagnosed) to have (FIG. 37).

5. Kit and System

The present invention provides a kit for detecting cancer, comprising nematodes. The kit of the present invention comprises nematodes. The present kit may also comprise one or more components necessary for carrying out the detection method of the present invention. Examples of such a component include a buffer, a culture solution, sodium azide, Escherichia coli, a petri dish, and agar. In addition, the kit of the present invention may also be a partial kit comprising only some of necessary components, and in such a case, the user may prepare other components. Moreover, the kit of the present invention may also include an instruction manual, which explains a detection method or an identification method.

Furthermore, the present invention provides a cancer detection system comprising nematodes, a storage part for storing a bio-related substance or a processed product thereof and the nematodes, and a detection part for detecting the reaction of the nematodes in the storage part.

Figure 16A:
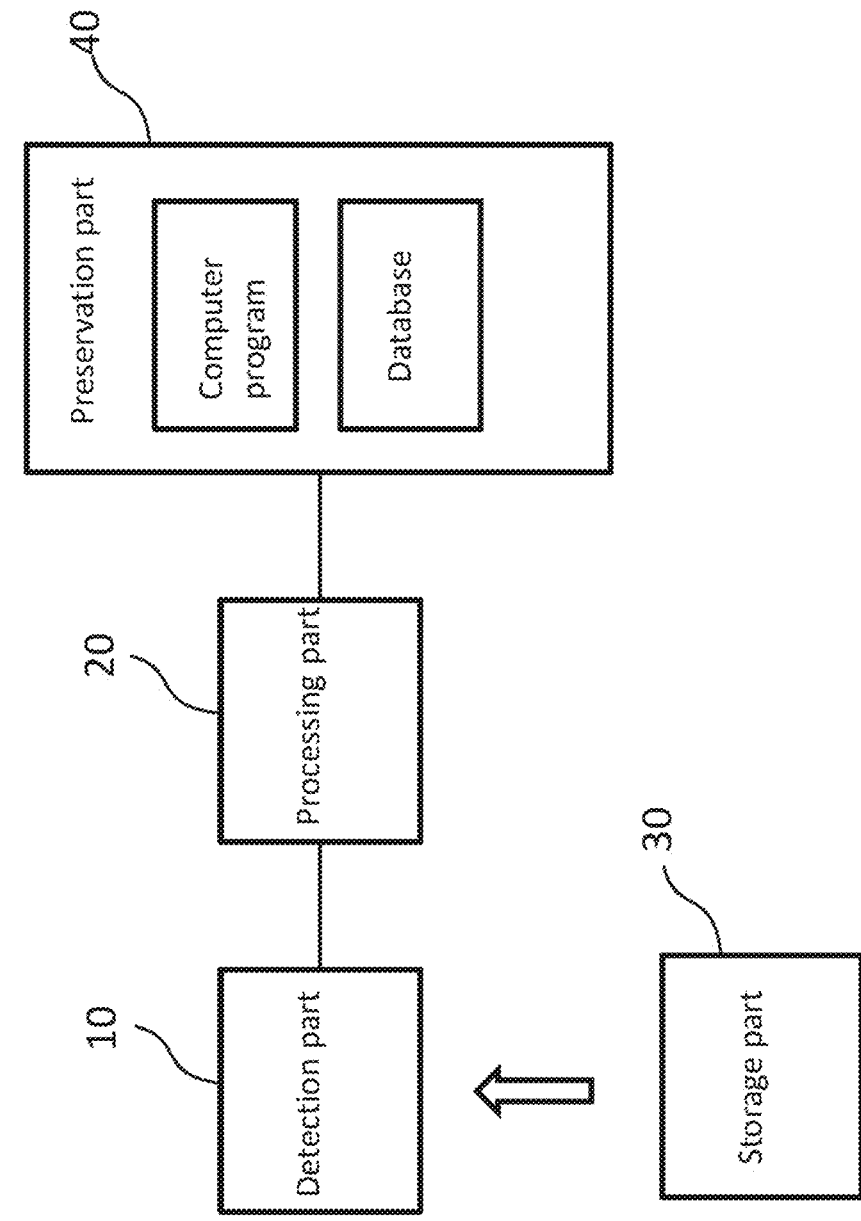
FIG. 16A is a block diagram showing the system of the present invention.

FIG. 16A is a block diagram showing the system of the present invention. In FIG. 16A, the system of the present invention has a storage part 30 for storing a bio-related substance or a processed product thereof and the aforementioned nematodes, a detection part 10 for detecting the reaction of the nematodes in the storage part 30 to a smell, and a processing part 20 for processing the detected information. Moreover, the system of the present invention may further comprise a preservation part 40 for preserving the data processed in the processing part 20. The preservation part 40 comprises program and database, which are for use in detection of cancer.

Examples of the storage part 30 include a petri dish, a culture dish, and a chip having micro flow channels. However, the type of the storage part is not limited, as long as it is able to store nematodes and a sample.

The system of the present invention comprises at least one detection part 10 capable of taking the moving image of at least one nematode in real time. The detection part 10 is a device for obtaining data such as the image of nematodes, the number of nematodes, and the tracks of movements. The detection part 10 comprises a microscope or a camera, for example, a fluorescence microscope, a digital microscope, a digital camera, etc. The microscope and the camera may comprise an automatic tracking (following) system capable of tracking the movement of nematodes, and this system tracks a single nematode, or simultaneously tracks a plurality of nematodes. Then, from the obtained tracks, the moving distance of nematodes is measured. Alternatively, nematodes, which are gathered in a predetermined area, are photographed, and the number of the nematodes is then counted. Moreover, the microscope and the camera may also comprise a sensor capable of detecting fluorescence intensity.

The system of the present invention is able to measure the movement of nematodes based on a real-time image, and is also able to measure the movement thereof based on a static image (photograph). By taking the image of nematodes in real time, it is possible to dynamically seek the position of the nematodes.

Figure 16B:
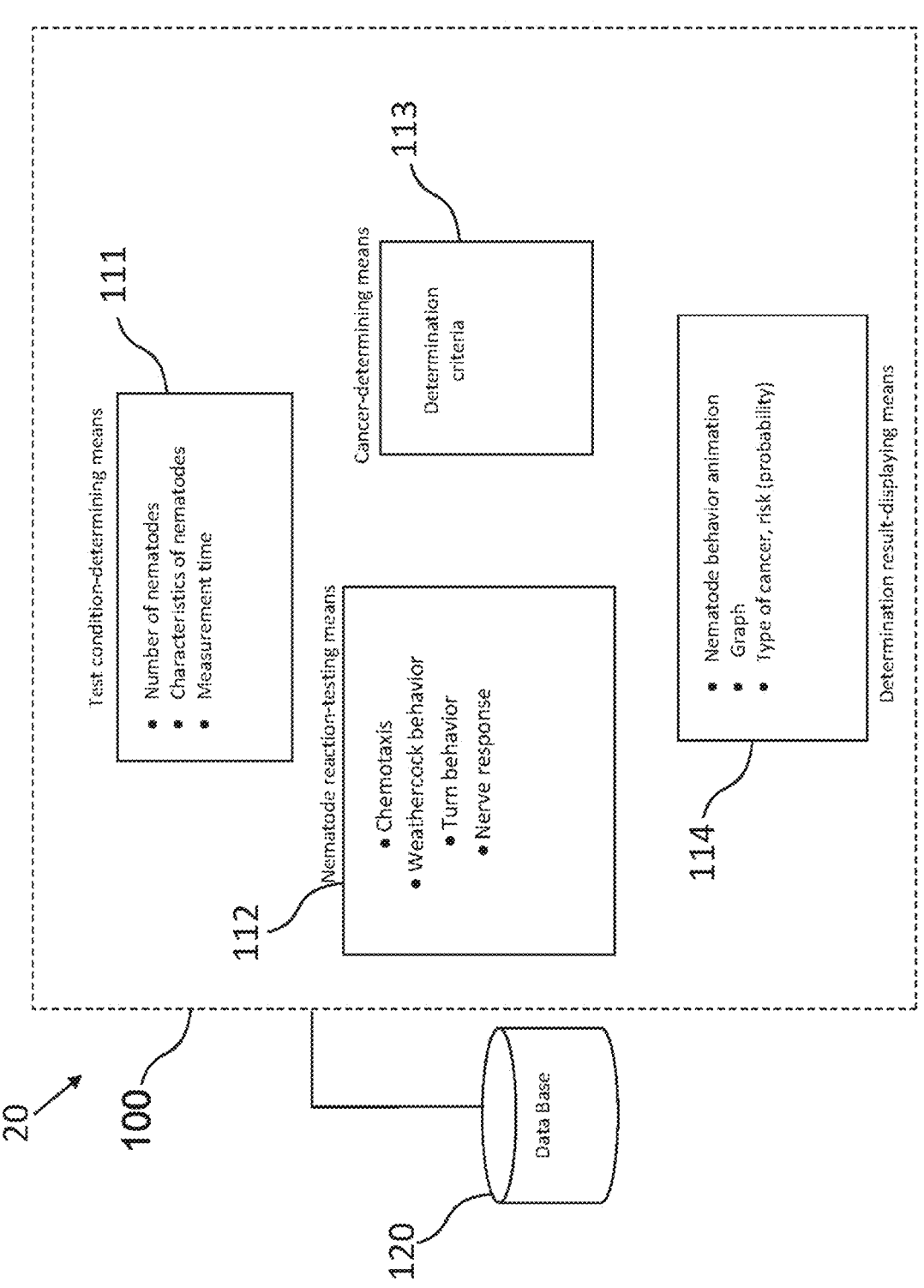
FIG. 16B is a configuration diagram showing a processing part of the system of the present invention.

FIG. 16B is a configuration diagram showing the processing part 20 of the system of the present invention. The processing part 20 is composed of a calculation means 110 and database 120. The calculation means 110 comprises (i) a test condition-determining means 111, (ii) a nematode reaction-testing means 112, (iii) a cancer determination means 113, and (iv) a test result-displaying means 114.

(i) Test Condition-Determining Means 111

The test condition-determining means 111 is a means for inputting conditions necessary for the calculation from a mouse or a keyboard according to GUI (Graphical User Interface), and the inputted information can be confirmed with a graph.

By this test condition-determining means, the system of the present invention has previously been allowed to store predetermined conditions, which depend on test purpose. Examples of such predetermined conditions include the number of nematodes, the characteristics of nematodes, application or non-application of chemotaxis index, and a measurement time.

The characteristics of nematodes include: deletion mutants; strains wherein a gene expression or the like is inhibited; and introduction of a gene encoding a fluorescent protein (e.g., a GFP gene, an RFP gene, etc.) for measurement. However, the conditions are not limited thereto, and can be determined, as appropriate, depending on test purpose.

(ii) Nematode Reaction-Testing Means 112

The nematode reaction-testing means 112 is a means for selecting a calculation formula for detecting or identifying cancer (e.g., chemotaxis index) from the test condition-determining means 111 or the database 120, and calculating the reaction of nematodes according to each calculation formula. By this means, the measurement of the number of nematodes in a predetermined area, the measurement of the total distance in which a single nematode has moved, detection of the fluorescence intensity emitted by a single nematode, etc. are carried out, and the behavior of a nematode(s) reacting to a test sample is recorded. For example, focusing on a single nematode, the distance obtained when the nematode has been attracted to a sample and has moved thereto is measured, and then, the moving distances of individual nematodes are added up to obtain a sum. Alternatively, when fluorescent protein genes have been introduced into nematodes, the fluorescent intensity of the nematodes that have reacted to a sample is measured. In this case as well, the fluorescence intensity of a single nematode may be measured, and then, the sum of nematodes may be then obtained. It may also be possible to measure fluorescence intensity emitted from the entire nematodes, which are gathered in a certain area, at an area unit.

(iii) Cancer Determination Means 113

The cancer determination means 113 is a means for detecting the presence or absence of cancer based on the reaction of nematodes to a smell, or identifying the type of cancer.

When the number of nematodes is adopted as a test condition, the ratio of the number of nematodes that have transferred to a test target area to the number of nematodes that have transferred to a control area, a difference between them, etc. is obtained. When the moving distance is adopted as a test condition, the percentage by which the moving distance of the concerned nematode is increased compared with the moving distance of a control nematode, at which the concerned nematode reacts to a smell, namely, the difference or ratio between the moving distances, can be obtained. If the constant value as such a difference or ratio has previously been determined as a boundary value, this boundary value can be used as a criterion for determination of cancer. Moreover, when the fluorescence intensity is adopted as a test condition, the percentage by which the fluorescence intensity of the concerned nematode is increased compared with the fluorescence intensity of a control nematode, at which the concerned nematode reacts to a smell, etc. can be determined as a boundary value, as in the case of the above-described moving distance.

A comparison is made among the measured data, the boundary value, and the sample information (information regarding cancer types, etc.), so that whether or not the sample has a certain cancer is determined.

(iv) Determination Result-Outputting Means 114

The determination result-outputting means 114 is a means for outputting relevant information, based on the detected or identified cancer types or the presence or absence of cancer, and it displays cancer types and the probability (risk). The results may be displayed either in a graph or in a table. An animation of the behavior of nematodes, which has been calculated in the above (ii), may also be displayed.

(v) Data Storage Means

The inputted test conditions and test results are correlated with each other, and they are preserved as data storage means in the database 120.

The thus preserved test conditions and calculation results can be read again from the database 120, or from the test condition-determining means 111 and the determination result-displaying means 114.

Hereinafter, the present invention will be more specifically described in the following Examples. However, the present invention does not be limited to these examples.

Example 1

Detection of Cancer (i) Breeding of Nematodes

Five or six wild-type adult nematodes N2 were placed on a 6-cm petri dish (containing an NGM medium, on which

*Escherichia coli* had been dispersed), and they were then cultured at 20° C. for 4 days. Approximately 300 to 500 next-generation nematodes were allowed to grow up to adult worms.

(ii) Chemotaxis Analysis

The format shown in FIG. 2 was produced in a 9-cm petri dish, and 0.5 μl each of sodium azide (NaN$_3$) was then placed on each of four points in the petri dish.

Thereafter, 1 ml of wash buffer was applied onto a nematode-breeding plate, and floating nematodes, together with the buffer, were then recovered in a tube. When the thus recovered nematodes were left for a while, they were gone down to the bottom. Thus, after the nematodes had been gone down, a supernatant was discarded. Thereafter, 1 ml of wash buffer was placed into the tube, and after the nematodes had been gone down, a supernatant was discarded. This washing operation was repeated three times to remove *Escherichia coli*.

1 μl each of urine sample, which had been diluted to 10 times with sterilized water, was placed on the "+" mark on the 9-cm petri dish.

Subsequently, approximately 100 nematodes were placed on the center of the petri dish, and the nematodes were bred (were allowed to swim) for 1 hour. The room temperature was set at 23° C.±1° C.

One hour later, the number of nematodes on the + side and the number of nematodes on the – side were counted, and the chemotaxis index was then calculated.

For one specimen, analyses were carried out five times. Then, a mean value of the 5 times of chemotaxis indices was calculated.

(iii) Results

The results are shown in FIG. 1. As shown in FIG. 1, negative (–) chemotaxis index (avoidance reaction) was exhibited to all of the healthy subject-derived urine samples used as controls (c1 to c10), whereas positive (+) chemotaxis index (attraction reaction) was exhibited to all of the cancer patient-derived urine samples (p1 to p20). Thus, cancer could be detected with an accuracy of 100%.

It is to be noted that, in FIG. 1, the error bar indicates SEM.

Example 2

Calcium Imaging

In an imaging experiment using micro flow channels, since a urine sample needed to be passed through a thin tube, precipitates and solids contained in the urine were removed by centrifugation and filtration (pore size: 0.22 μm, Millex GP, Merck Millipore). In order to monitor the AWC and AWA neurons, by using odr-1 and odr-10 promoters, respectively, a Yellow Cameleon gene (YC3.60) was allowed to express in neurons. Calcium imaging was carried out according to a known method (Uozumi, T. et al. Temporally-regulated quick activation and inactivation of Ras is important for olfactory behaviour. Sci Rep 2, 500 (2012); Shinkai, Y. et al. Behavioral choice between conflicting alternatives is regulated by a receptor guanylyl cyclase, GCY-28, and a receptor tyrosine kinase, SCD-2, in AIA interneurons of *Caenorhabditis elegans*. J Neurosci 31, 3007-3015 (2011)).

A nematode was immobilized on a microchannel, such that the head portion of the nematode could be put out of the microchannel (FIG. 5). Using a single nematode, the reaction of the single nematode to each of control urine and cancer patient-derived urine was tested.

The fluorescence image of YC3.60 was obtained using a Leica DMI3000B microscope (40-fold objective lens) and an ORCA-D2 digital camera (Hamamatsu). All images were obtained at an exposure time of 200 ms. The fluorescence intensities of CFP and YFP were obtained from the AWC or AWA neuron. The ratio of the fluorescence intensity of YFP to the fluorescence intensity of CFP was analyzed using Metamorph software (Molecular devices). This fluorescence intensity ratio was calculated as YFP intensity/CFP intensity (=R), and an average of the ratios of 10-s windows (–10-0 s) was set at R0.

Figure 7:
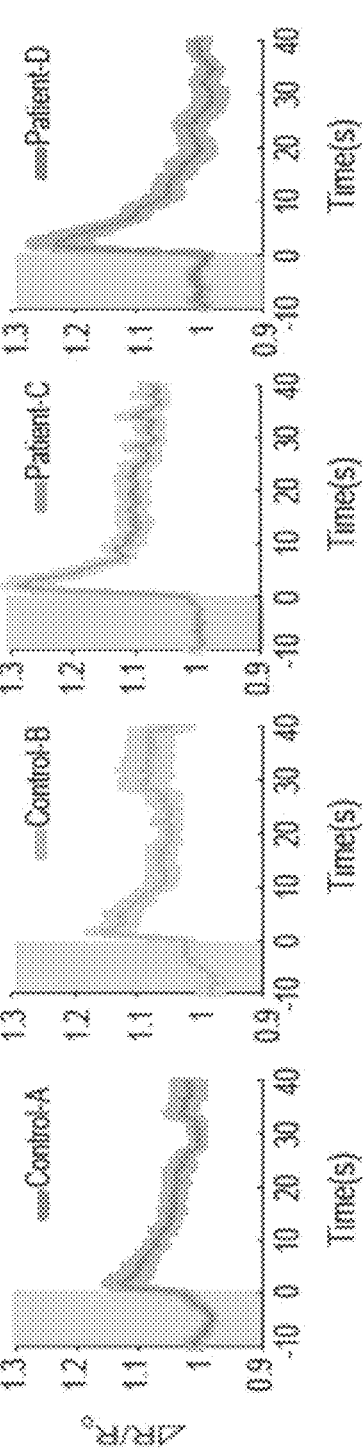
FIG. 7 is a view showing the results obtained by examining the reaction of the AWC olfactory neuron of a nematode to cancer patient-derived urine.
Figure 8:
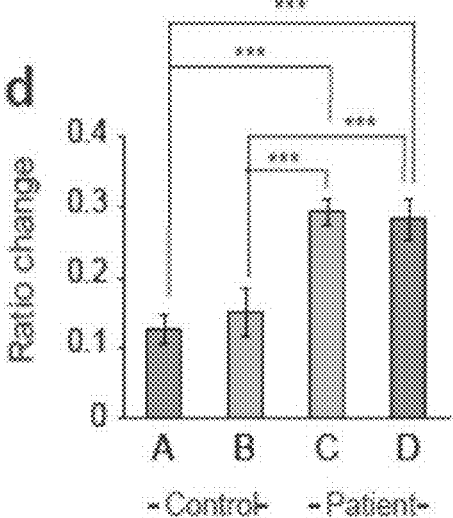
FIG. 8 is a view showing the results obtained by examining the reaction of the AWC olfactory neuron of a nematode to cancer patient-derived urine.

The results obtained by examining the reaction of the AWC olfactory neurons of nematodes to cancer patient-derived urine are shown in FIGS. 7 and 8.

In FIG. 7, two left panels show the results of a test performed using control urine, and two right panels show the results of a test performed using gastric cancer patient-derived urine. FIG. 7 is a view showing a change in the calcium concentration of the AWC olfactory neuron (a change in the YFP/CFP ratio of Yellow Cameleon) to urine stimulation (with urine→without urine). In compared to the urine of a healthy subject (control), significantly strong reaction to the urine of a cancer patient was found. FIG. 8 shows a change in the amount of the mean fluorescence intensity ratio (YFP/CFP ratio). The symbol *** indicates that it is significant at $p < 0.001$.

In the present example, precipitates and solids contained in urine were removed by centrifugation and filtration. These treatments did not influence on the chemotaxis of nematodes (FIG. 9).

Figure 10:
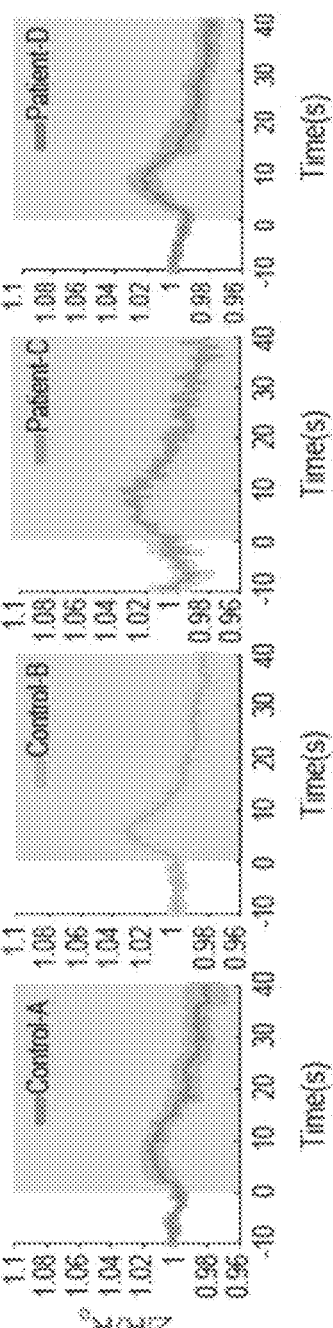
FIG. 10 is a view showing the results obtained by examining the reaction of the AWA olfactory neuron of a nematode to cancer patient-derived urine.
Figure 11:
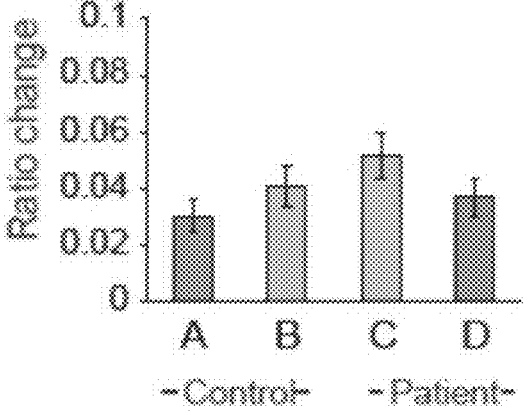
FIG. 11 is a view showing the results obtained by examining the reaction of the AWA olfactory neuron of a nematode to cancer patient-derived urine.

Even in the case of the AWA olfactory neuron, the response was observed as a result of addition of urine (FIGS. 10 and 11).

These results demonstrate that the olfactory neuron of a nematode plays an important role in distinguishing control urine from cancer patient-derived urine. FIGS. 7 to 11 show that cancer can be detected by utilizing the olfactory neuron of a nematode. It is to be noted that, in FIGS. 8, 9 and 11, the error bar indicates SEM.

Example 3

In the present example, the established cancer cell lines, and culture media or preservation solutions were used as models of subject-derived bio-related substances, and a cancer detection experiment was carried out.

(1) Detection of Cancer Using Cancer Cell Lines

In order to detect cancer using a culture supernatant of human cancer cells, SW480, COLO201 and COLO205 were used as large bowel cancer (colo-rectal cancer) cells; MCF7 was used as breast cancer cells; and NUGC4, MKN1 and MKN7 were used as gastric cancer cells.

Figure 12:
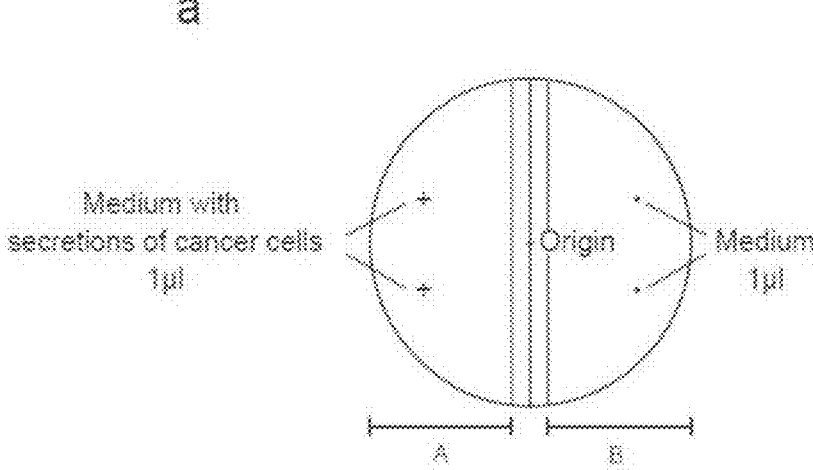
FIG. 12 is a view showing assay plates.
Figure 12:
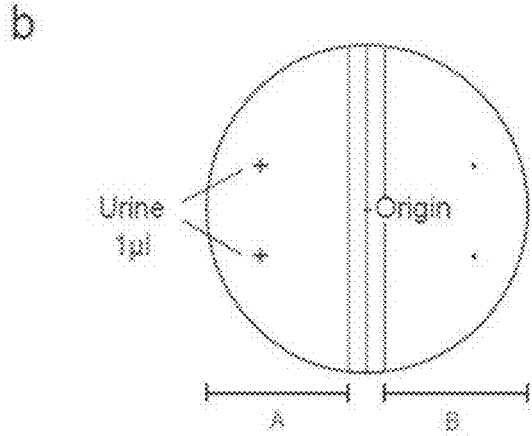

SW480, COLO201 and COLO205 were acquired from National Institute of Biomedical Innovation, JCRB Cell Bank (Japanese Collection of Research Bioresources Cell Bank (Tokyo, http://cellbank.nibio.go.jp)), and other types of cells were acquired from Cell Resource Center for Bio-medical Research, Institute of Development, Aging and Cancer (Tohoku University, Sendai, Japan)). Using 10% FBS-added RPMI 1640 medium, all of the cell lines were maintained in a condition in which they were not confluent at 37° C. in 5% CO$_2$ aeration. A culture solution, which was a clear layer in the upper portion of the medium, was used in the test. The medium after the cell culture was spotted in the position "+" in an assay plate (FIG. 12). In order to eliminate the influence of the smell of the medium itself, a control culture solution, which had been diluted to the same concentration as described above, was spotted in a position on the side opposite to the spotted position of the cell culture medium (FIG. 12).

The chemotaxis of nematodes was tested on an assay plate in the same manner as that of Example 1. As a result, wild-type nematodes (*C. elegans*) exhibited an attraction behavior to the culture medium (diluted to $1/10^6$ to $1/10^7$) on which the cancer cells had been cultured (FIG. 13).

Figure 13:
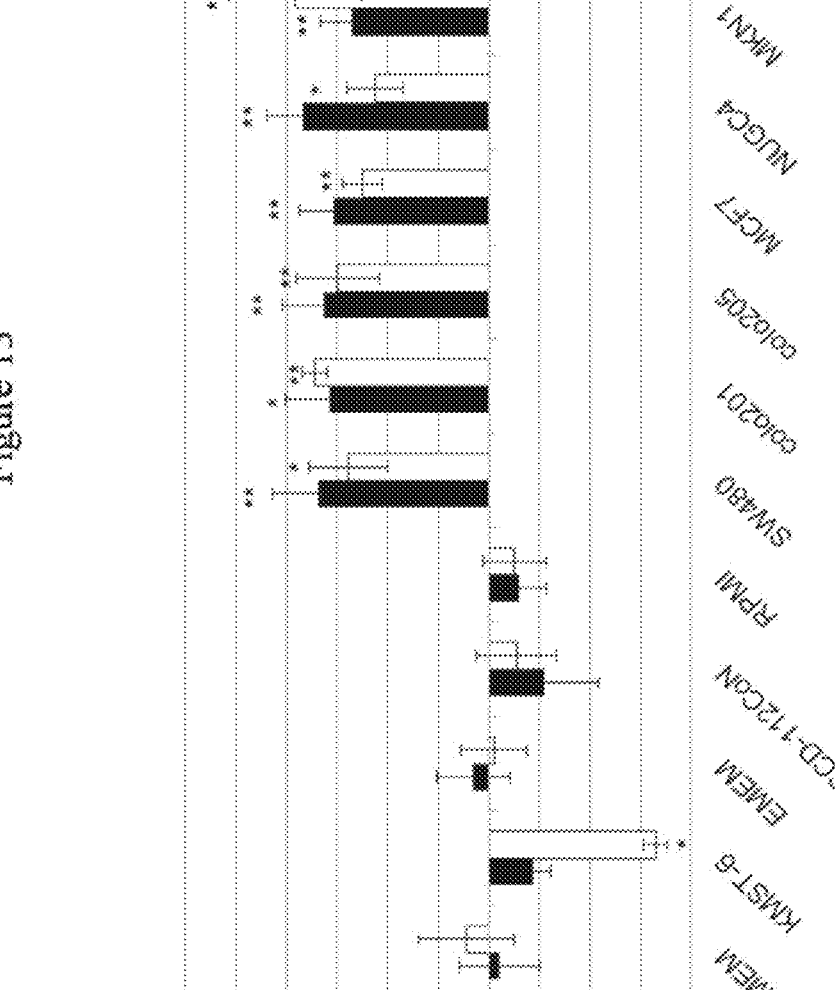
FIG. 13 is a view showing the attraction behaviour of nematodes to a culture medium of cancer cells.

In FIG. 13, the left bar shows the results obtained using a $1/10^6$-diluted cancer cell culture medium, and the right bar shows the results obtained using a $1/10^7$-diluted cancer cell culture medium. In addition, the symbol * indicates that it is significant at $p<0.05$;  indicates that it is significant at $p<0.01$; and * indicates that it is significant at $p<0.001$ (Dunnett's test). Moreover, in FIG. 13, the error bar indicates SEM.

A culture solution or a preservative solution of fibroblasts (non-cancerous cells) was also tested in the same manner as described above. As a result, it was demonstrated that nematodes did not exhibit an attraction behavior to the culture solution or preservative solution (weak avoidance) (FIG. 13). This means that nematodes do not exhibit an attraction behavior to a "secretion from human cells," but exhibit an attraction behavior to a "secretion from cancer cells."

MEM, EMEM and RPMI each indicate a medium alone. KMST-6 and CCD-112CoN indicate fibroblasts (which were acquired from RBC and ATCC, respectively).

(2) Chemotaxis to Fibroblast Culture Media and Cancer Cell Culture Media

Moreover, the chemotaxis to fibroblast culture media and cancer cell culture media, which had various concentrations, and the chemotaxis of nematodes to human cancer tissues, were also examined. The methods therefor are as follows.

A fibroblast culture medium and a cancer cell culture medium were each diluted with water to result in various concentrations (ranging from the stock solution thereof to $10^{-9}$), and the chemotaxis of wild-type nematodes to individual culture media was observed. Regarding human cancer tissues and normal tissues, after obtaining informed consent, these tissues were excised from a cancer patient, and they were fragmented to samples each having a diameter of 0.1 to 0.8 mm, and were then used.

Figure 17:
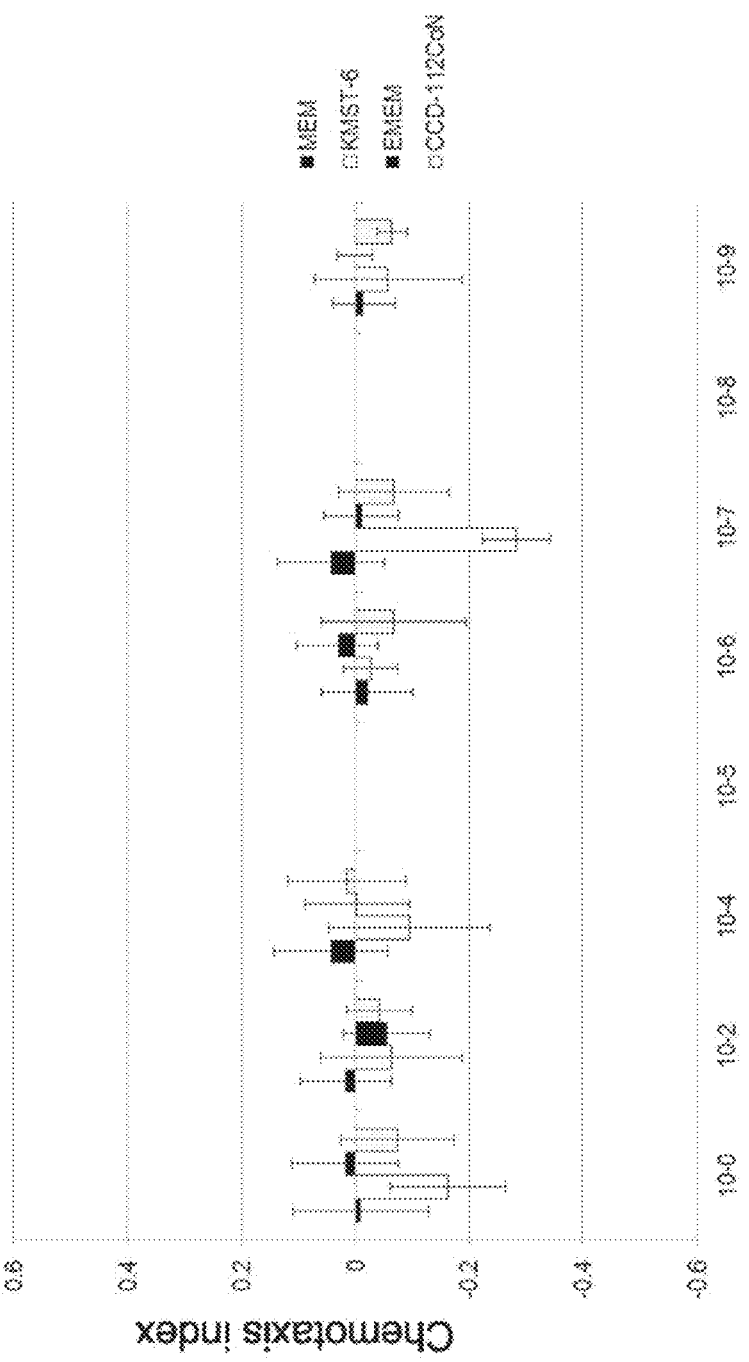
FIG. 17 is a view showing the chemotaxis of nematodes to fibroblast culture media having different concentrations.
Figure 18:
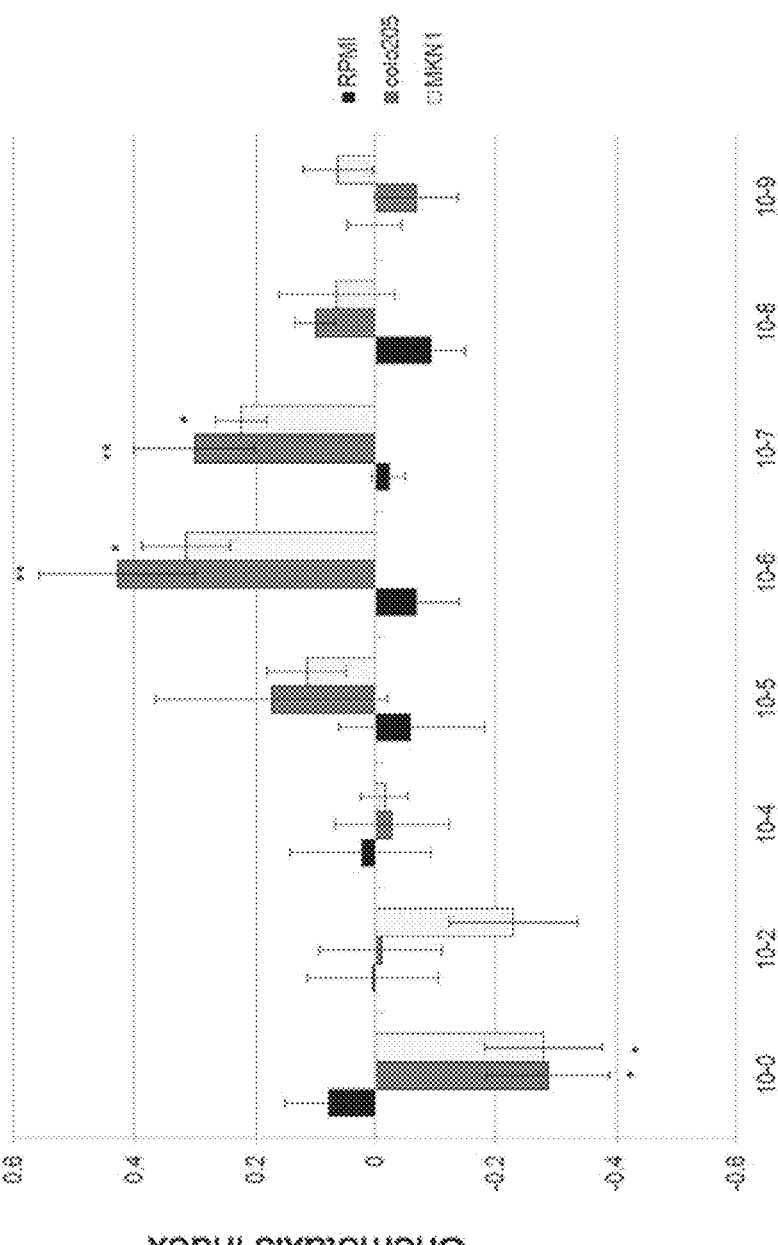
FIG. 18 is a view showing the chemotaxis of nematodes to cancer cell culture media having different concentrations.

As a result, the nematodes did not exhibit an attraction behavior to all concentrations of fibroblasts, but it was observed that the nematodes exhibited a significant attraction behavior to cancer cells having concentrations of $10^{-6}$ and $10^{-7}$ (FIGS. 17 and 18).

With regard to the chemotaxis of nematodes to human cancer tissues, the nematodes exhibited an attraction behavior to a cancer tissue section, but they exhibited an avoidance behavior to the normal tissues (tissues farthest from the cancer tissues) of the same patient as the one having the aforementioned cancer tissues (FIG. 19). It was also found that when cancer tissues are placed on one side and normal tissues are placed on the other side, the nematodes approach to the cancer tissues.

(3) Chemotaxis to Physiologic Saline Preservative Solution Containing Cancer Tissue Section A human cancer tissue section was added to a physiologic saline, and the obtained solution was preserved at −20° C. (preservation period: 3 months). Thereafter, the chemotaxis of nematodes to a dilution of the physiologic saline was studied.

After obtaining informed consent, cancer tissues having a diameter of 0.5 cm were excised from a cancer patient, and were then added to 20 ml of physiologic saline. The resulting physiologic saline was diluted with water to result in concentrations of $10^{-2}$ to $10^{-4}$, and the chemotaxis of wild-type nematodes to these diluted solutions was then observed.

As a result, the nematodes exhibited an attraction behavior to the physiologic saline containing cancer tissues, but they exhibited an avoidance behavior to a physiologic saline containing normal tissues (FIG. 20).

Since the odr-3 mutant did not exhibit an attraction behavior to the physiologic saline containing cancer tissues, it can be said that the nematodes feel the smell.

Example 4

Mid-Scale Test

In order to confirm the high accuracy of the method of the present invention, a test was carried out using 242 urine samples (218 control samples and 24 cancer patient-derived samples) (Table 1). Table 1 shows the background of subjects.

TABLE 1

| | | | a, Background characteristics of participants for final-examination | | | |
|---|---|---|---|---|---|---|
| | | | NSDT (+) | | | |
| | Cancer 2 yrs before | Cancer within 2 yrs | Not found cancer | NSDT (+) | NSDT (−) | p-Value NSDT positive vs negative |
| n | 19 | 5 | 11 | 35 | 207 | | |
| Gender (male) | 12 | 3 | 2 | 17 | 87 | 0.68 | NS |
| Age (years) (median) | 47-89 (68) | 53-70 (60) | 41-73 (53) | 41-89 (66) | 26-78 (46) | 1.3E−08 | P < 0.001 |
| Cancer history | 0 | 0 | 0 | 0 | 6 | 0.67 | NS |
| | | | Complaints | | | |
| Cough or sputum | 0 | 1 | 1 | 2 | 7 | 0.85 | NS |
| Appetite loss | 1 | 1 | 0 | 2 | 0 | 0.02 | P < 0.05 |
| Abdominal discomfort | 0 | 0 | 1 | 1 | 6 | 0.60 | NS |
| Malaise | 1 | 1 | 2 | 4 | 15 | 0.61 | NS |
| Chest discomfort | 1 | 1 | 1 | 3 | 4 | 0.11 | NS |
| Bowel disturbance | 3 | 1 | 0 | 4 | 9 | 0.19 | NS |

TABLE 1-continued a. Background characteristics of participants for final-examination

| | NSDT (+) | | | | | p-Value NSDT positive vs negative | |
|---|---|---|---|---|---|---|---|
| | Cancer 2 yrs before | Cancer within 2 yrs | Not found cancer | NSDT (+) | NSDT (−) | | |
| Headache | 0 | 1 | 3 | 4 | 12 | 0.38 | NS |
| Bloody discharge | 1 | 0 | 0 | 1 | 1 | 0.67 | NS |
| Pregnancy | 0 | 0 | 0 | 0 | 3 | 0.91 | NS |
| Custom drinking | 6 | 1 | 1 | 8 | 81 | 0.07 | NS |
| Custom smoking | 3 | 2 | 1 | 6 | 40 | 0.76 | NS |
| Diseases other than cancer | | | | | | | |
| Hypertension | 11 | 4 | 1 | 16 | 32 | 3.3E−05 | P < 0.001 |
| Hyperlipidemia | 6 | 0 | 0 | 6 | 17 | 0.10 | NS |
| Diabetes | 3 | 0 | 0 | 3 | 12 | 0.80 | NS |
| Hyperuricemia | 1 | 0 | 1 | 2 | 6 | 0.73 | NS |
| Ischemic heart disease | 0 | 1 | 0 | 1 | 3 | 0.91 | NS |
| Cerebral infarction | 2 | 0 | 0 | 2 | 0 | 0.02 | P < 0.05 |
| Collagen disease | 0 | 0 | 0 | 0 | 1 | 0.31 | NS |
| Thyropathy | 0 | 0 | 0 | 0 | 2 | 0.67 | NS |
| Bronchial asthuma | 0 | 0 | 0 | 0 | 3 | 0.91 | NS |
| Gastroduodenal ulcer | 0 | 0 | 0 | 0 | 1 | 0.31 | NS |
| Chronic pancreatitis | 0 | 0 | 0 | 0 | 1 | 0.31 | NS |
| Chronic hepatitis | 0 | 0 | 1 | 1 | 4 | 0.77 | NS |
| Osteoarthritis | 0 | 1 | 1 | 2 | 4 | 0.46 | NS |
| Uterine myoma | 0 | 0 | 0 | 0 | 2 | 0.67 | NS |
| Mental disorder | 0 | 0 | 0 | 0 | 1 | 0.31 | NS |
| Ophthalmologic disease | 0 | 0 | 0 | 0 | 7 | 0.58 | NS |
| Laboratory data | | | | | | | |
| WBC ($\times 10^2$/$\mu$L) (median) | 47-110 (55) | 50-91 (57) | 44-80 (56) | 44-110 (56) | 34-141 (60) | 0.91 | NS |
| Hgb (g/dl) (median) | 5.1-17.2 (13.9) | 13.2-16.7 (14.6) | 9.3-15.3 (13.1) | 5.1-17.2 (13.4) | 8.4-17.6 (14.1) | 0.02 | P < 0.005 |
| Plt ($\times 10^4$/$\mu$L) (median) | 13.6-41.1 (20.5) | 15.6-31.1 (18.5) | 19.9-41.8 (24.2) | 13.6-41.8 (21.4) | 10.7-46.1 (23.2) | 0.41 | NS |
| Urine creatinine (mg/dl) (median) | 0.32-1.63 (0.85) | 0.25-0.77 (0.54) | 0.10-1.26 (0.64) | 0.10-1.63 (0.73) | 0.12-2.56 (0.89) | 0.04 | P < 0.05 |
| CRP (>0.31 mg/dl) | 5 | 0 | 1 | 6 | 17 | 0.10 | NS |
| CEA (>5.0 ng/ml) | 5 | 1 | 0 | 6 | 8 | 0.002 | P < 0.01 |
| Anti-p53 Ab (>1.30 U/ml) | 4 | 0 | 2 | 6 | 18 | 0.12 | NS |
| DiAcSpm/Cre Male > 243, Female > 354 (nmol/g · Cre) | 4 | 0 | 0 | 4 | 10 | 0.12 | NS |
| Positive in some tumor markers | 10 | 1 | 2 | 13 | 34 | 0.004 | P < 0.01 |

All of the urine samples were 10-fold diluted, and the chemotaxis test using nematodes was carried out three times for each sample.

Figure 14:
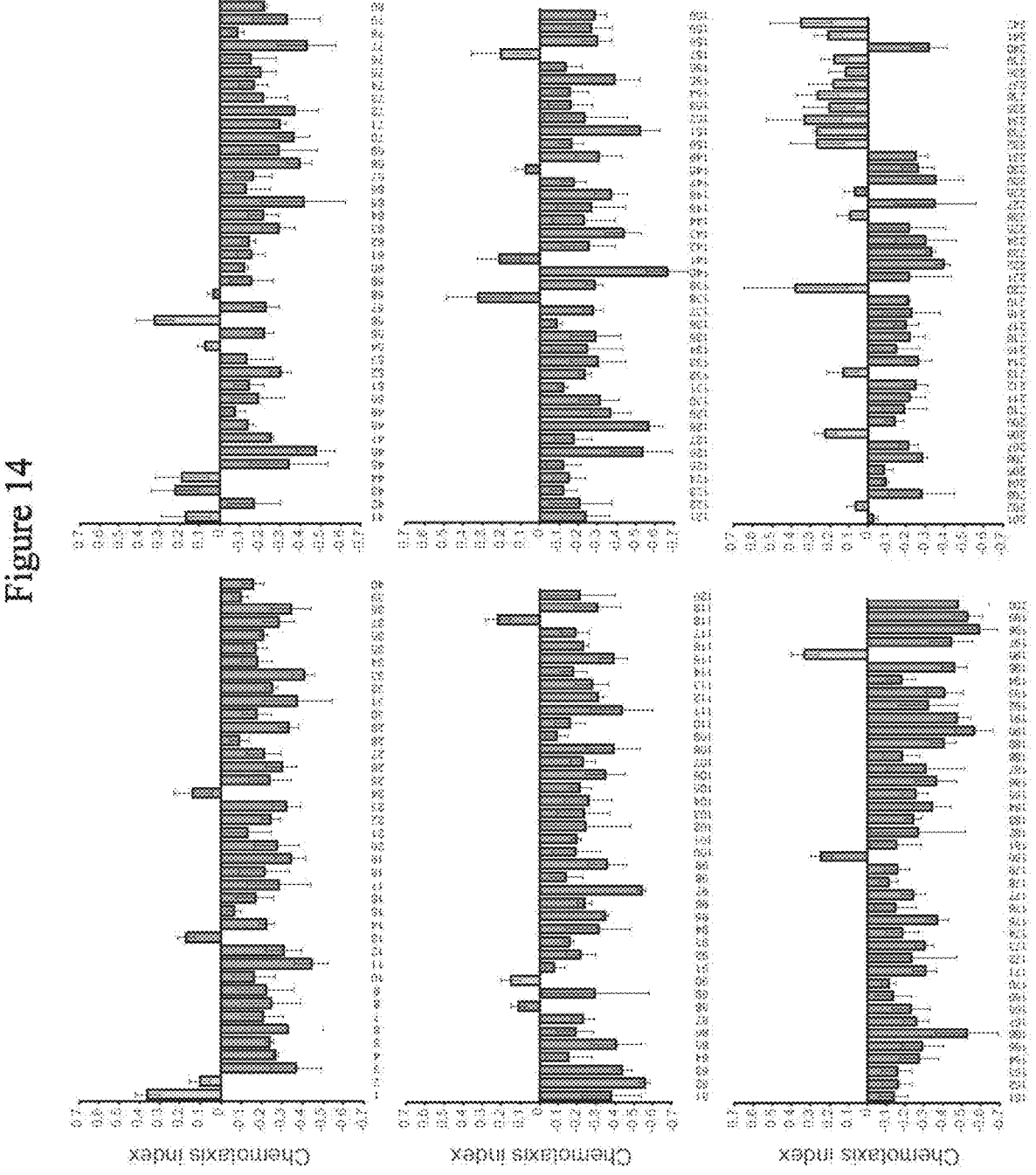
FIG. 14 is a view showing the results of a mid-scale test of the method of the present invention.

As a result, the nematodes exhibited an attraction reaction to all of the cancer patient-derived urine samples (24/24), and the detection sensitivity was 100% (FIG. 14). On the other hand, the nematode exhibited an avoidance behavior to almost all control urine samples (207/218) (FIG. 14). In FIG. 14, the orange bars (Nos. 1, 2, 41, 44, 54, 56, 90, 157, 196, 202, 208, 213, 220, 226, 232-239, 241, and 242) indicate cancer patient-derived samples, and the blue bars (the numbers other than the aforementioned numbers) indicate control samples. Moreover, in FIG. 14, the error bar indicates SEM.

The present inventor has also studied other tumor markers for the same subjects.

Figure 15:
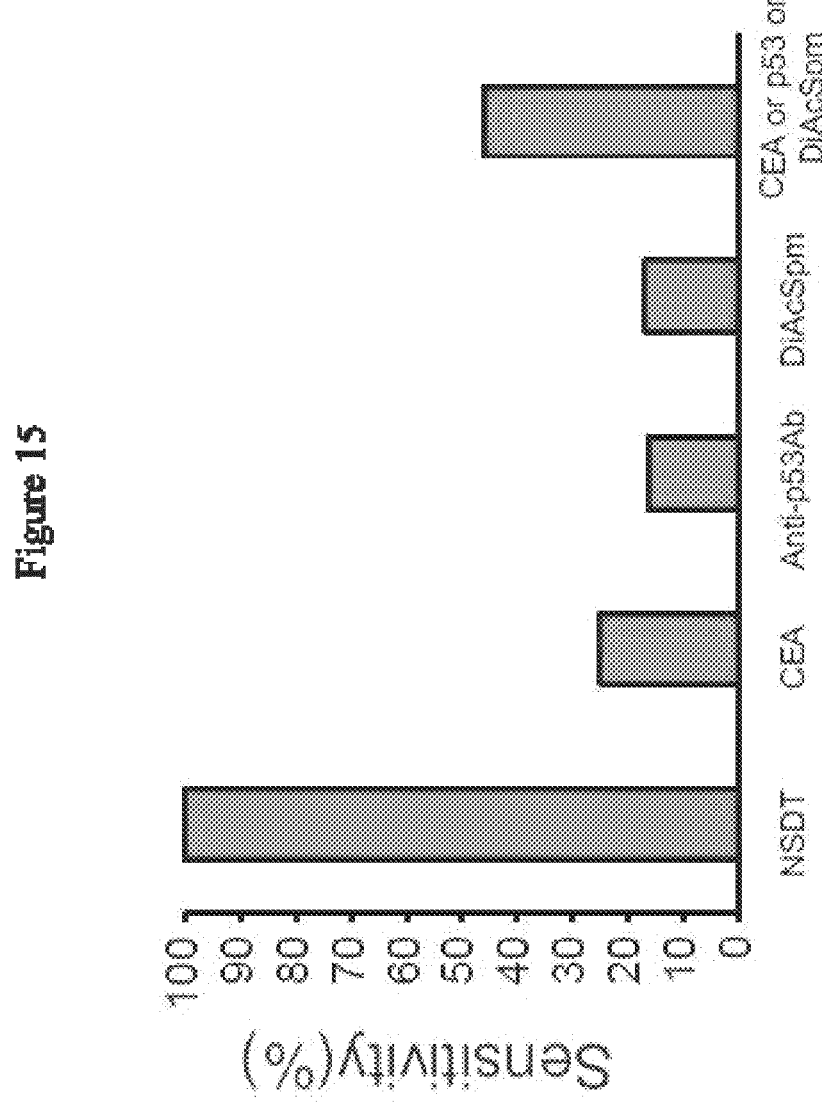
FIG. 15 is a view showing the results obtained by performing a mid-scale test using the method of the present invention and other tumor markers, and then making a comparison among them, in terms of sensitivity.

The tumor markers used as study targets were serum CEA, serum anti-p53 antibody (Anti-p53 Ab), and urine $N^1,N^{12}$-diacetylspermine (DiAcSpm). When compared with these tumor markers, the method of the present invention (NSDT) had extremely high sensitivity (FIG. 15 and Table 2). It is to be noted that sensitivity (%) indicates the ratio of positive responses to cancer patient-derived samples.

TABLE 2

| Extended Data Table 3 The Accuracy of tumor markers in final examination | | | | | | | |
|---|---|---|---|---|---|---|---|
| | Stage | n | CEA | Anti-p53 Ab | DiAcSpm | Some TMs | NSDT |
| Esophageal ca. | 0 | 1 | 0 | 0 | 0 | 0 | 1 |
| | Total | 1 | 0 | 0 | 0 | 0 | 1 |
| Gastric ca. | I | 4 | 0 | 1 | 0 | 1 | 4 |
| | IV | 1 | 1 | 0 | 0 | 1 | 1 |
| | Total | 5 | 1 | 1 | 0 | 2 | 5 |
| Colorectal ca. | 0 | 2 | 1 | 0 | 0 | 1 | 2 |
| | I | 1 | 0 | 0 | 0 | 0 | 1 |
| | II | 2 | 0 | 1 | 0 | 1 | 2 |
| | III | 4 | 1 | 0 | 1 | 2 | 4 |
| | IV | 1 | 1 | 1 | 1 | 1 | 1 |
| | Total | 10 | 3 | 2 | 2 | 5 | 10 |
| Breast ca. | I | 2 | 0 | 1 | 0 | 1 | 2 |
| | II | 3 | 1 | 0 | 0 | 1 | 3 |
| | Total | 5 | 1 | 1 | 0 | 2 | 5 |
| Pancreatic ca. | IV | 1 | 1 | 0 | 1 | 1 | 1 |
| | Total | 1 | 1 | 0 | 0 | 1 | 1 |
| Bile duct ca. | I | 1 | 0 | 0 | 1 | 1 | 1 |
| | Total | 1 | 0 | 0 | 1 | 1 | 1 |
| Prostate ca. | I | 1 | 0 | 0 | 0 | 0 | 1 |
| | Total | 1 | 0 | 0 | 0 | 0 | 1 |
| All cancers | 0 | 3 | 1 | 0 | 0 | 1 | 3 |
| | I | 9 | 0 | 2 | 1 | 3 | 9 |
| | II | 5 | 1 | 1 | 0 | 2 | 5 |
| | III | 4 | 1 | 0 | 1 | 2 | 4 |
| | IV | 3 | 3 | 1 | 2 | 3 | 3 |
| | Total | 24 | 6 | 4 | 4 | 11 | 24 |

| Sensitivity | Stage | CEA | Anti-p53 Ab | DiAcSpm | Some TMs | NSDT |
|---|---|---|---|---|---|---|
| | 0 | 33.3% | 0.0% | 0.0% | 33.3% | 100% |
| | I | 0.0% | 22.2% | 11.1% | 33.3% | 100% |
| | II | 20.0% | 20.0% | 0.0% | 40.0% | 100% |
| | III | 25.0% | 0.0% | 25.0% | 50.0% | 100% |
| | IV | 100% | 33.3% | 66.7% | 100% | 100% |
| | Total | 25.0% | 16.7% | 16.7% | 45.8% | 100% |
| Specificity | | 96.3% | 86.2% | 95.4% | 83.9% | 95.0% |
| Positive predictive value | | 42.9% | 17.4% | 28.6% | 23.9% | 68.6% |
| Efficiency | | 89.3% | 83.9% | 87.6% | 80.2% | 95.5% |

Table 2 includes cancer patients at stages 0 and 1. This means that the method of the present invention is also useful for detection of early cancer.

Example 5

Studies Regarding Optimal Concentration of Urine
Method:

Three specimens as urine samples from healthy subjects (c1, c2, and c3) and five specimens as urine samples from cancer patients (p2, p5, p8, p17, and p18) were each diluted with water to result in various types of concentrations (ranging from the stock solution thereof to $10^{-5}$), and thereafter, the chemotaxis of wild-type nematodes thereto was studied.
Results:

As shown in FIG. 21, it was demonstrated that a 10-fold dilution is preferable. In FIG. 21, in the bar graph showing each concentration, the three bars on the left side show the results obtained using urine derived from healthy subjects, and the five bars on the right side show the results obtained using urine derived from cancer patients.

Example 6

Identification of Receptor (1) Materials and Method

Culture of Nematodes and Nematode Strains

Except for the eri-1 mutant that was cultured with *Escherichia coli* (*E. coli*) OP50, the nematodes (*C. elegans*) were cultured at 20° C. under standard conditions in a nematode growth medium (NGM) plate (36) comprising *Escherichia coli* NA22 as a food source. The used wild-type nematodes were of a Bristol N2 strain. As other nematode strains, GR1373: eri-1 (mg366), VC2123: sri-14 (ok2865), CX3410: odr-10 (ky225), and MT7929: unc-13 (e51) were used.

RNA Interference and Chemotaxis Assay

The RNAi assay was carried out by performing an RNAi method involving the feeding (feeding RNAi method) of eri-1 (mg366) (19), using an Ahringer library (37).

Nine adult eri-1 mutants were placed on an NGM plate containing isopropyl β-D-1-thiogalactopyranoside (0.19 g/L), ampicillin (60 mg/L), and *Escherichia coli* (*E. coli*), and were then cultured for 4 days. Subsequently, the adult worms were used in a chemotaxis assay. The chemotaxis assay was carried out as previously reported (6, 17). In the chemotaxis assay, the present inventor has used 30 to 50 worms in each experiment in which 1 μl of $10^{-3}$- or $10^{-4}$-diluted odorant (low concentration), or 1 and 5 μl of undiluted odorants (high concentration) were used.

The results of the RNAi screening were statistically analyzed as follows.

The z score and a control value in each single test from 2SD were calculated in all days (Table 3) or every day. The z score was used as a threshold indicating a great difference (−1.96 and 1.96, P<0.05). However, it was seemed that inhibition of one receptor did not cause remarkable effects. Accordingly, the present inventor has used the z score±1 (−0.96 and 0.96, P<0.33) as a weaker threshold.

Avoidance from Osmotic Pressure

The present inventor has used 4 M NaCl for osmotic stimulus, and has assayed an osmotic pressure avoidance behavior, as previously reported (38).

Cell-Specific Knockdown of Function of sri-14

A gene to knock down the function of sri-14 in specific neurons was constructed, as previously reported (24). The target region of sri-14 (a 1.6-kb genome sequence) was amplified using the following two primers:

```
Tf:
                                  (SEQ ID NO: 1)
5'-ggcgccgatataattgctaa-3',
and Tr;
                                  (SEQ ID NO: 2)
5'-ctgctgcgtttttcgtatca-3'.
```

The gene expression of ASH was carried out using a sra-6 (20) promoter, and that of AWC was carried out using ceh-36 (39) and srd-17 promoters.

Genetic Ablation and Inhibition of Neurons

The present inventor has used mouse caspase-1 (mCasp1) for ablation of the AWA, AWB, AWC and ASH neurons. mCasp1 was each expressed by odr-10 (11), str-1 (15), ceh-36 (39), and sra-6 (20) promoters, respectively. Moreover, for inhibition of interneurons, unc-103 (go was used. The AIA-, AIB-, AIY-, or AIZ-specific expression of the unc-103 (go was carried out using a gcy-28.d (29), npr-9 (40), ttx-3 (41, 42), or lin-11 (43, 44) promoter, respectively.

Preparation and Amplification of sri-14 cDNA

Total RNA, which had been isolated using PureLink RNA Minikit (Ambion), was converted to cDNA by ReverTra Ace qPCR master mix using gDNA Remover (Toyobo) in accordance with the instructions made by the manufacturer. The sri-14 cDNA was amplified using the following two primers, was then digested with Nhe I and Kpn I, and was then inserted into a pPD-DEST vector (Invitrogen):

```
                                  (SEQ ID NO: 3)
5'-gagaGCTAGCaaaaaatgcctgcaggtccac-3',
and
```

-continued

```
                                  (SEQ ID NO: 4)
     5'-gagaGGTACCttattgaattctcggttg-3'.
```

Calcium Imaging

In order to monitor the response of the AWA, AWB, AWC and ASH neurons, the present inventor has produced strains expressing YC3.60, using odr-10, str-1, odr-3, and sra-6 promoters (11, 15, 20, and 45), respectively. As previously reported (33, 46, 47), calcium imaging was carried out using a microfluidic device. In an experiment using such a micro-fluidic device, a nematode was captured by a microchannel such that the nose of the nematode was exposed to running water containing a solution of diacetyl [$10^{-5}$-diluted (low concentration) and $10^{-3}$-diluted (high concentration)], or a solution with no smell, and thus, each nematode was immo-bilized. The room temperature was set from 20° C. to 23° C. The fluorescence image of YC3.60 was taken using Zeiss Axioplan 2 comprising 40× objective lens and a 3CCD digital camera (C7780, Hamamatsu Photonics). All images were recovered at an exposure time of 200 ms. The time stacks of AWA, AWB, AWC, and ASH cell bodies were captured, and thereafter, using AquaCosmos software (ver. 2.6, Hamamatsu Photonics), the emission ratio between a yellow fluorescent protein (YFP) and a cyan fluorescent protein (CFP) was analyzed. This ratio was calculated as YEP intensity/CFP intensity (R), and the average ratio in 10-second window (−10 to 0 seconds) was set as R0.

(2) Results

RNA Interference Screening of Smell-Receptor Pairs

In order to comprehensively identify olfactory receptors necessary for the response to specific odorants, the present inventor has carried out a systematic RNA interference (RNAi) screening. RNAi in the neurons of the nematodes (*C. elegans*) is not effective for wild-type nematodes because of the low sensitivity of the nematode (*C. elegans*) neurons to the RNAi (18). Thus, the RNAi-enhanced nema-tode strain eri-1 (mg366) (19) was used herein.

The present inventor has demonstrated that, as a result of the RNAi of the eri-1 mutant, the knockdown of odr-10 causes a specific defect in the response to a low concentra-tion ($10^{-3}$ diluted) of diacetyl, and the inventor has con-firmed that this nematode strain can be effectively used for the RNAi screening of olfactory receptor genes (FIG. 22). Genes encoding 822 putative olfactory receptors, including the SRH family, were screened (wherein all of the genes encode GPCR). The response of RNAi-treated nematodes to 11 odorants was tested. Since the nematodes (*C. elegans*) may change preference depending on the concentration of an odorant (17), the response thereof to higher concentrations of the odorants (1 μl and 5 μl of undiluted odorants) (wherein the odorants cause an attraction behavior to nematodes, when they are used at low concentrations) was further examined. The odorants included low concentrations of six attractants (6), high concentrations of three attractants that induce avoidance at high concentrations (17), and high concentrations of two repellents (6, 20) (FIG. 22).

The test was repeatedly performed on an RNAi-treated nematode strain, which had abnormality in the chemical sensation-induced motion response to an odorant (see the section "Materials and method") (Table 3). As a result of the third screening, since RNAi of genes encoding 194 putative olfactory receptors caused a weaker response to one or more odorants than a control did, the genes were considered to encode the candidate olfactory receptors (FIG. 22 and Table 4).

Since genes, which are expressed in sensory neurons, are likely to act as olfactory receptors, the expression patterns of these genes were then examined.

Using fluorescent reporters ligated to the promoters of genes encoding individual olfactory receptors, the present inventor has analyzed the expression patterns of genes encoding 16 putative olfactory receptors, knockdown of which had caused severe defects in the chemical sensation-induced motions (FIG. 22C and FIGS. 23A-L). Moreover, regarding the expression patterns of 19 olfactory receptor genes, information disclosed in WormBase (wormbase.org) was used. Among these 35 genes, 30 genes were expressed in neurons. Among the 16 genes analyzed based on reporter expression, 15 genes were expressed in sensory neurons associated with the sense of smell (Table 5).

Identification of Olfactory Receptor SRI-14 Responding to High Concentration of Diacetyl ODR-10 is a diacetyl receptor, and an odr-10 mutant has a defect in chemotaxis to a low diacetyl concentration (11). As previously reported (11), the present inventor had confirmed that the odr-10 mutant exhibits a normal chemotaxis to a high concentration of diacetyl (FIG. 24A). This suggests that other receptors are present with respect to diacetyl, and that ODR-10 may be specific to a low concentration of diacetyl (21). As a result of the RNAi screening, 5 olfactory receptor candidate genes (srh-25, srh-79, srh-216, srh-281 and sri-14) associated with a high concentration of diacetyl were obtained (Table 3 and FIG. 25). Thus, the present inventor has analyzed the expression using upstream promoters. As a result, the expression of srh-79 and srh-216 could not be detected, and the expression of srh-25 and srh-281 was observed in ADL sensory neurons, which were not associated with the avoidance behavior to a high concentration of diacetyl (Table 5). Accordingly, in order to understand how various receptors cause concentration-dependent reactions to a single odorant, the present inventor has focused on sri-14. This is because RNAi of this gene caused a significantly strong defect in the avoidance from a high concentration of diacetyl (FIG. 24B).

SRI-14 is encoded by a gene having 7 exons, and according to WormBase, ok2685 is a deletion mutant predicted to be loss-of-function (FIG. 26A). Referring to the putative amino acid sequence of SRI-14 (SEQ ID NO: 5), the protein was found to have a putative 7-transmembrane domain (FIGS. 26B and C). The behavioral analysis of a sri-14 (ok2865) mutant under high osmotic pressure conditions demonstrated that the nematodes exhibit a normal high osmotic pressure avoidance behavior. However, the sri-14 mutant exhibited a defect in the avoidance response to a high concentration of diacetyl, as in the case of sri-14 RNAi-treated nematodes (FIG. 24A). Moreover, when compared with the odr-10 mutant, the sri-14 mutant exhibited a defect in chemotaxis specific to a high concentration of diacetyl (FIG. 24A). The sri-14 mutant exhibited a normal response to other repellents and high concentrations of other attractants (FIG. 24C). This suggests that SRI-14 is associated with only detection of a high concentration of diacetyl, among the examined odorants.

As a result of the reporter expression analysis, it was found that sri-14 is expressed in the AWC and ASH chemosensory neurons (FIG. 24D). The AWC neurons are considered to be necessary for detection of a large number of attractants comprising 10-fold diluted diacetyl (22, 23), and the ASH neurons are associated with avoidance from a repellent (9) and a high concentration of isoamyl alcohol (17). In order to clarify whether SRI-14 functions in the AWC or ASH neurons in the response to a high concentration of diacetyl, the present inventor has conducted the neuron-specific knockdown of sri-14 in the AWC and ASH neurons (24). As a result, the ASH-specific knockdown of sri-14 caused a defect in the avoidance from diacetyl, but in the case of the AWC-specific knockdown, abnormality was not observed (FIG. 24E).

Furthermore, a defect in the avoidance of the sri-14 mutant from a high concentration of diacetyl was rescued by the ASH-specific expression of the sri-14 cDNA, but it was partially rescued or was not rescued by the specific expression in the AWA, AWB or AWC olfactory neurons (FIG. 24F). These results demonstrate that the function of SRI-14 in the ASH sensory neurons is necessary and sufficient for mediating the avoidance from a high concentration of diacetyl. The avoidance response to high osmotic pressure conditions is mediated by the ASH neurons (25, 26). The result that this response is normal in the case of the sri-14 mutant (FIG. 26D) indicates that the ASH neurons are normal with regard to detection of other avoidance stimulations and response thereto. In addition, a fusion protein of SRI-14 and a green fluorescent protein (GFP) was localized in the sensory cilia of the ASH neurons (FIG. 24G). This demonstrates that SRI-14 functions as a factor for olfactory signaling in the sensory cilia of ASH.

Identification of Sensory Neurons and Interneurons Associated with Preference Change Depending on Concentration of Odorant A low concentration of diacetyl ($10^{-4}$ diluted solution) is detected by the AWA neurons (6), and an intermediate concentration of diacetyl ($10^{-1}$ diluted solution) is detected by the AWC neurons (22, 23). These neurons both mediate attraction. However, what sensory neurons detect a high concentration of diacetyl (undiluted) and are associated with an avoidance response has not been known. In the previous studies, it had been demonstrated that the ASH and AWB sensory neurons detect a high concentration of isoamyl alcohol (17) and mediate avoidance. Further, the AWC and AWB neurons are associated with both attraction and avoidance (17, 27).

Hence, the present inventor has examined the involvement of the ASH, AWB and AWC sensory neurons with the avoidance response to a high concentration of diacetyl. Nematodes, from which AWB or AWC had been genetically ablated, did not exhibit a defect in the chemotaxis of responding to a high concentration of diacetyl (FIG. 27A). However, when the ASH neurons were ablated, this avoidance behavior was inhibited (FIG. 27A). These results demonstrate that the ASH neurons mainly detect a high concentration of diacetyl, and the results are consistent with the results that SRI-14 functions in the ASH neurons.

In order to examine whether or not the AWA neurons mediate avoidance from diacetyl and attraction to diacetyl, the present inventor has analyzed the behavioral response of nematodes, from which the AWA neurons had been specifically ablated. The nematodes, from which AWA had been ablated, exhibited a decrease in the avoidance from a high concentration of diacetyl (FIG. 27A), and a decrease in the attraction to a low concentration of diacetyl (FIG. 27B). This is similar to the ability of the AWC and AWB neurons, which function for both attraction and avoidance (17, 27). The double ablation of both AWA and ASH causes a more severe defect than in the case of a single ablation, and these results show that both AWA and ASH function in parallel, in the response to a high concentration of diacetyl (FIG. 27A).

In order to clarify contribution of interneurons to an odor-concentration-dependent preference change, the present inventor has examined the involvement of AIA, AIB, AIY and AIZ interneurons having a direct synaptic junction or gap junction with the AWA or ASH sensory neurons, or with both of the sensory neurons (FIG. 27C). These interneurons were individually inhibited by the neuron-specific expression of unc-103 (gf) providing hyperpolarization (28, 29). The functional inhibition of the AIA, AIY or AIZ interneurons changed the response of nematodes exposed to a high concentration of diacetyl from an avoidance response to an attraction response (FIG. 27D), and inhibition of AIB attenuated the avoidance response. These results show that these interneurons play an important role in a smell-concentration-dependent preference change, and are matched with the previous report that AIB, AIY and AIZ are important for different behavioral responses to a high concentration of and a low concentration of isoamyl alcohol (17). In contrast, attraction to a low concentration of diacetyl was not influenced by inhibition of these interneurons except for AIY (FIG. 27E). This suggests that a neural circuit for mediating attraction to a lower concentration of diacetyl is different from a neural circuit for mediating avoidance from a high concentration of diacetyl.

Proper use of Olfactory Receptors Depending on Smell Concentration

The results of the nematode behavior experiments conducted by the present inventor and the previous study results (11) suggest that a concentration-dependent preference change to diacetyl is mediated by two types of receptors, namely, ODR-10 in the AWA neurons and SRI-14 in the ASH neurons. Hence, the present inventor has monitored the response of the AWA and ASH neurons to various concentrations of diacetyl by calcium imaging, in which a genetically encoded calcium indicator Yellow Cameleon (YC) 3.60 (30) was used in wild-type nematodes, odr-10 mutants, and sri-14 mutants.

In the AWA neurons of the wild-type nematodes or the sri-14 mutants, intracellular calcium was increased after the nematodes had been exposed to a low concentration of diacetyl (29) (FIGS. 28A and B). However, the odr-10 mutants did not respond to such a low concentration of diacetyl (FIGS. 28A and B). These results are consistent with the findings that ODR-10 functions as a receptor specific to a low concentration of diacetyl in the AWA neurons (21). In contrast, the AWA neurons of the odr-10 mutants and the wild-type nematodes normally responded to a high concentration of diacetyl (FIGS. 28C and D). These results are consistent with the findings that the odr-10 mutants exhibited a normal chemotaxis to a high concentration of diacetyl (FIG. 24A). Since ablation of these neurons reduced both attraction and avoidance responses (FIGS. 27A and B), these results comprehensively suggest that receptors other than ODR-10 are present in the AWA neurons and detect a high concentration of diacetyl.

The present inventor has monitored a transient Ca2+ response in the ASH neurons. In the ASH neurons of wild-type nematodes, a Ca2+ response only to a high concentration of diacetyl was detected (FIG. 29A). In order to clarify whether or not the ASH response to a high concentration of diacetyl is influenced by other neurons, the present inventor has analyzed the Ca2+ response in the ASH of unc-13(e51) mutants having a defect in the exocytosis of synaptic vesicles (31). The calcium response of the ASH neurons of the unc-13 mutants to a high concentration of diacetyl was significantly larger than that of the ASH neurons of wild-type nematodes, and was prolonged (FIGS. 30A, B, and D). This suggests that signals from other neurons inhibit the activity of ASH in the response to diacetyl.

Since it has been observed that the response to diacetyl is changed in AWA-ablated nematodes (FIGS. 27, A and B), the present inventor has further tested the effects of AWA ablation on the calcium response of the ASH neurons to a high concentration of diacetyl. As a result, the inventor has found that ablation of the AWA neurons enhances the calcium response of the ASH neurons (FIGS. 30A, C, and D). This suggests that AWA is associated with an ASH response inhibitory circuit.

Thereafter, the present inventor has monitored the Ca2+ response of the ASH neurons of mutant nematodes to a high concentration of diacetyl. The Ca2+ response was normally induced in the ASH neurons of the odr-10 mutant, but such a response was significantly reduced in the ASH neurons of the sri-14 mutant (FIGS. 29B and C). A defect in the response of ASH of the sri-14 mutant to a high concentration of diacetyl was rescued by the ASH-specific expression of a wild-type sri-14 gene (FIGS. 29B and C). Moreover, when sri-14 was ASH-specifically knocked down in wild-type nematodes, the Ca2+ response of ASH to a high concentration of diacetyl was reduced (FIGS. 29B and C). These results demonstrate that SRI-14 functions as a main component for reception of a high concentration of diacetyl in the ASH neurons.

Since the expression of sri-14 has been observed in the AWC neurons and the ASH neurons (FIG. 24D), the present inventor has monitored the AWC response to a high concentration of diacetyl. An increase in the Ca2+ concentration in AWC was caused by the removal of the smell (32). As such, the present inventor has tested the response of the AWC neurons after the removal of a high concentration of diacetyl, and as a result, the inventor has found that a Ca2+ response occurs in the AWC neurons (FIG. 31). These results are consistent with the previous report that diacetyl is detected by AWC and AWA (22, 23). However, ablation of AWC did not influence on avoidance from a high concentration of diacetyl (FIG. 27A). This suggests that the response of the AWC neurons is not important for avoidance from diacetyl. Since the behavioral response to a high concentration of diacetyl was not influenced by the AWC-specific expression of sri-14 or the AWC-specific knockdown of sri-14 (FIGS. 24E and F), it is considered that there will be receptors other than SRI-14, which mediate the response of AWC to a high concentration of diacetyl.

In general, the AWB neurons are associated with an avoidance behavior (15). In the previous studies, it had been reported that the Ca2+ response of the AWB neurons occurs after the removal of nonanone or a high concentration of isoamyl alcohol (17, 33). Thus, the present inventor has carried out the ectopic expression of sri-14 cDNA in the AWB neurons, and has monitored the Ca2+ response to various concentrations of diacetyl.

The present inventor has observed a slight Ca2+ response after the removal of the smell in both case of a low concentration of and a high concentration of diacetyl in the wild-type AWB neurons. When compared with such a weak response in the wild-type AWB neurons, the Ca2+ response of the AWB neurons after the removal of a high concentration of diacetyl was significantly enhanced by the ectopic expression of SRI-14. However, the ectopic expression of SRI-14 did not change the response to the removal of a low concentration of diacetyl (FIGS. 32A and B). These results support our conclusion that SRI-14 contributes to detection of a high concentration of diacetyl. In addition, these findings suggest that ODR-10 in the AWA neurons and SRI-14 in the ASH neurons respond to a low concentration of and a high concentration of diacetyl, respectively, and that they function as receptors for mediating attraction and avoidance behaviors (FIG. 33).

(3) Consideration

In order to comprehensively identify olfactory receptors for specific odorants, the present inventor has used RNAi screening. Since the nematodes (*C. elegans*) have olfactory receptors and olfactory signaling, which are similar to those of mammals (23, 34), they are considered to be model organisms for olfactory analysis. Moreover, there are described all neural networks capable of following pathways in which olfactory signals are transmitted on the neural circuits (35). However, the correspondence relationship of a majority of odorants with specific receptors or receptor oligomers has not been known, and the mechanism of the interaction between odorants and olfactory receptors has not been known, either. As a consequence, how smell signals are inputted, how olfactory signals are transmitted on the neural circuits, and how a small number of ORNs in the nematodes (*C. elegans*) are able to distinguish an extremely large number of odorants, have not been understood. A further analysis of receptor candidates obtained as a result of the RNAi screening is useful for identifying olfactory receptors for specific odorants and understanding these mechanisms.

The present inventor had previously reported that different sensory neurons function depending on the concentration of a smell (17). In this study, the present inventor has found that, regarding reception of diacetyl, ODR-10 and SRI-14 respectively function as receptors specific to a low concentration of and a high concentration of diacetyl in specific ORNs (FIG. 33). It is assumed that SRI-14 is likely to have a lower affinity for diacetyl than that of ODR-10. However, these receptors do not have a homologous sequence in an odorant recognition site, and thus, the mechanism that is the base of the ability of these receptors to distinguish the same chemical substances having different concentrations has remained unknown.

In the calcium imaging experiment, it has been demonstrated that the AWA sensory neurons respond to both a low concentration of and a high concentration of diacetyl. The genetic ablation of the AWA neurons caused a defect in avoidance from a high concentration of diacetyl and in attraction to a low concentration of diacetyl. These results suggest that the AWA neurons contribute to detect diacetyl having a wide range of concentrations and to cause an opposite behavior to a different concentration. These findings, and the previously reported findings regarding the AWB neurons (16) and the AWC neurons (26), show that these ORNs of the nematodes (*C. elegans*) are able to mediate both an attraction behavior and an avoidance behavior. ODR-10 was present in the AWA neurons (11), and the odr-10 mutant exhibited a reduced attraction to a low concentration of diacetyl, but it exhibited a normal avoidance to a high concentration of diacetyl. These results suggest that the AWA neurons have a plurality of diacetyl receptors, particularly for a high concentration of diacetyl.

There are receptor candidates for a high concentration of diacetyl, other than SRI-14, which were obtained by the present inventor according to RNAi screening. The analysis of these other candidates is likely to bring on identification of other diacetyl receptors and addition of strategies by which different receptors act depending on the concentration of a smell.

TABLE 3

|  | Iaa | Bz | Bu | Pd | Pz | Tmt |
|---|---|---|---|---|---|---|
| Control | 0.59 ± 0.019 | 0.48 ± 0.019 | 0.65 ± 0.021 | 0.49 ± 0.020 | 0.49 ± 0.019 | 0.64 ± 0.015 |
| srh-4 | 0.36 | 0.20 | 0.65 | 0.53 | 0.26 | 0.80 |
| srh-7 | 0.55 | 0.92 | 0.91 | 0.84 | 0.77 | 0.76 |
| srh-8 | 0.91 | 0.67 | 0.93 | 0.66 | 0.52 | 0.59 |
| srh-10 | −0.12 | 0.12 | −0.65 | 0.68 | 0.67 | 0.88 |
| srh-11 | 0.05 | −0.11 | −0.15 | 0.75 | 0.87 | 0.85 |
| srh-15 | 0.59 | −0.13 | 0.55 | 0.44 | 0.78 | 0.91 |
| srh-16 | 0.86 | 0.83 | 0.74 | 0.95 | 0.82 | 0.49 |
| srh-18 | 0.67 | 0.05 | 0.52 | 0.96 | 0.73 | 0.91 |
| srh-19 | 0.67 | 0.64 | 0.89 | 0.64 | 0.33 | 0.88 |
| srh-22 | 0.58 | 0.28 | 0.19 | 0.42 | 0.82 | 0.75 |
| srh-23 | 0.54 | 0.54 | 0.67 | 0.48 | 0.43 | 0.78 |
| srh-24 | 0.58 | 0.69 | 0.59 | 0.59 | 0.57 | 0.92 |
| srh-25 | 0.28 | 0.36 | 0.72 | 0.95 | 0.64 | 0.95 |
| srh-27 | 0.48 | −0.16 | 0.63 | 0.27 | 0.32 | 0.71 |
| srh-28 | 0.63 | 0.68 | 0.55 | 0.22 | 0.23 | 0.92 |
| srh-36 | 0.37 | 0.42 | 0.37 | 0.26 | 0.53 | 0.51 |
| srh-37 | 0.57 | 0.65 | 0.37 | 0.60 | 0.88 | 0.87 |
| srh-39 | 0.56 | −0.08 | 0.48 | −0.24 | 0.11 | 0.45 |
| srh-40 | 0.79 | 0.50 | 0.94 | 0.47 | 0.51 | 0.73 |
| srh-41 | 0.57 | 0.49 | 0.64 | 0.57 | 0.71 | 0.85 |
| srh-44 | 0.71 | 0.51 | 0.82 | 0.52 | 0.44 | 0.90 |
| srh-45 | 0.55 | 0.40 | 0.73 | 0.26 | 0.74 | 0.73 |
| srh-46 | 0.58 | 0.17 | 0.82 | 0.03 | −0.04 | 0.83 |
| srh-48 | 0.77 | 0.29 | 0.55 | 0.38 | 0.15 | 0.65 |
| srh-49 | 0.58 | 0.42 | 0.80 | 0.60 | 0.52 | 0.59 |
| srh-50 | 0.60 | 0.40 | 0.87 | 0.53 | 0.83 | 0.84 |
| srh-51 | 0.41 | 0.44 | 0.70 | 0.63 | 0.31 | 0.64 |
| srh-52 | 0.50 | 0.26 | 0.69 | 0.51 | 0.55 | 0.55 |
| srh-55 | 0.49 | 0.68 | 0.43 | 0.49 | 0.56 | 0.56 |
| srh-59 | 0.31 | −0.35 | 0.51 | −0.14 | 0.04 | 0.37 |
| srh-60 | 0.66 | 0.32 | 0.79 | 0.22 | 0.52 | 0.79 |
| srh-61 | 0.52 | 0.62 | 0.74 | 0.40 | 0.27 | 0.70 |
| srh-67 | 0.55 | 0.29 | 0.85 | 0.41 | 0.39 | 0.63 |
| srh-68 | 0.75 | 0.49 | 0.67 | 0.21 | 0.36 | 0.57 |
| srh-69 | 0.63 | 0.33 | 0.66 | 0.13 | 0.35 | 0.75 |
| srh-70 | 0.42 | 0.28 | 0.43 | 0.25 | 0.41 | 0.78 |

TABLE 3-continued

| | | | | | | |
|---|---|---|---|---|---|---|
| srh-71 | 0.19 | 0.00 | 0.76 | 0.14 | 0.56 | 0.85 |
| srh-72 | 0.52 | 0.74 | 0.58 | 0.29 | 0.50 | 0.58 |
| srh-74 | 0.50 | 0.55 | 0.76 | 0.42 | 0.26 | 0.44 |
| srh-75 | 0.69 | 0.32 | 0.76 | 0.53 | 0.71 | 0.54 |
| srh-77 | 0.16 | 0.17 | 0.70 | 0.32 | 0.44 | 0.52 |
| srh-79 | 0.39 | 0.23 | 0.58 | 0.53 | 0.12 | 0.42 |
| srh-80 | 0.45 | 0.20 | 0.64 | 0.41 | 0.40 | 0.39 |
| srh-82 | 0.77 | 0.25 | 0.79 | 0.49 | 0.31 | 0.71 |
| srh-83 | 0.51 | 0.38 | 0.71 | 0.72 | 0.38 | 0.86 |
| srh-97 | 0.49 | 0.20 | 0.80 | 0.74 | 0.66 | 0.77 |
| srh-99 | 0.48 | 0.23 | 0.75 | 0.54 | 0.29 | 0.65 |
| srh-100 | 0.76 | 0.73 | 0.80 | 0.35 | 0.30 | 0.62 |
| srh-104 | 0.48 | 0.19 | 0.48 | −0.30 | −0.18 | 0.65 |
| srh-105 | 0.58 | 0.33 | 0.76 | 0.27 | 0.32 | 0.66 |
| srh-109 | 0.59 | 0.22 | 0.89 | 0.65 | 0.32 | 0.76 |
| srh-111 | 0.44 | 0.10 | 0.59 | 0.39 | −0.23 | 0.37 |
| srh-113 | 0.39 | −0.32 | 0.30 | 0.14 | 0.35 | 0.83 |
| srh-115 | 0.40 | 0.41 | 0.70 | 0.39 | 0.19 | 0.47 |
| srh-116 | 0.76 | 0.11 | 0.56 | 0.22 | 0.35 | 0.56 |
| srh-118 | 0.59 | 0.79 | 0.60 | 0.44 | 0.36 | 0.73 |
| srh-119 | 0.39 | −0.22 | 0.50 | 0.18 | 0.37 | 0.71 |
| srh-120 | 0.34 | 0.52 | 0.78 | 0.80 | 0.54 | 0.72 |
| srh-122 | 0.25 | 0.21 | 0.58 | 0.24 | 0.47 | 0.44 |
| srh-123 | 0.46 | 0.40 | 0.84 | 0.30 | 0.63 | 0.56 |
| srh-125 | 0.35 | 0.52 | 0.76 | 0.08 | 0.39 | 0.70 |
| srh-128 | 0.25 | 0.36 | 0.69 | 0.49 | 0.54 | 0.62 |
| srh-129 | 0.69 | 0.36 | 0.63 | 0.15 | 0.71 | 0.69 |
| srh-130 | 0.60 | 0.20 | 0.82 | 0.36 | 0.22 | 0.70 |
| srh-131 | 0.59 | 0.33 | 0.80 | 0.26 | 0.63 | 0.77 |
| srh-132 | 0.43 | 0.23 | 0.26 | 0.10 | 0.22 | 0.57 |
| srh-139 | 0.73 | 0.41 | 0.44 | 0.06 | 0.29 | 0.75 |
| srh-140 | 0.46 | 0.07 | 0.70 | −0.08 | −0.06 | 0.50 |
| srh-141 | 0.70 | 0.23 | 0.56 | 0.47 | 0.33 | 0.81 |
| srh-142 | −0.14 | 0.17 | 0.68 | 0.36 | 0.61 | 0.47 |
| srh-145 | 0.78 | 0.61 | 0.93 | 0.39 | 0.46 | 0.79 |
| srh-148 | 0.49 | 0.21 | 0.78 | 0.39 | 0.36 | 0.54 |
| srh-154 | 0.79 | 0.42 | 0.82 | 0.58 | 0.61 | 0.61 |
| srh-159 | 0.54 | 0.27 | 0.78 | 0.38 | 0.22 | 0.57 |
| srh-165 | 0.27 | 0.17 | 0.75 | 0.44 | 0.57 | 0.58 |
| srh-166 | 0.44 | 0.19 | 0.54 | 0.08 | 0.23 | 0.74 |
| srh-167 | 0.02 | −0.31 | 0.25 | −0.16 | 0.33 | 0.43 |
| srh-169 | 0.65 | 0.34 | 0.04 | 0.20 | 0.11 | 0.63 |
| srh-174 | 0.76 | 0.23 | 0.70 | 0.51 | 0.76 | 0.73 |
| srh-179 | 0.53 | 0.61 | 0.77 | 0.44 | 0.40 | 0.75 |
| srh-182 | 0.71 | 0.57 | 0.61 | 0.52 | 0.26 | 0.59 |
| srh-186 | 0.51 | 0.58 | 0.65 | 0.72 | 0.73 | 0.80 |
| srh-190 | 0.57 | 0.28 | 0.53 | 0.11 | 0.17 | 0.63 |
| srh-193 | 0.64 | 0.53 | 0.85 | 0.60 | 0.55 | 0.62 |
| srh-195 | 0.61 | 0.67 | 0.31 | 0.36 | 0.70 | 0.93 |
| srh-201 | 0.81 | 0.67 | 0.82 | 0.79 | 0.46 | 0.83 |
| srh-203 | 0.67 | 0.42 | 0.63 | 0.36 | 0.50 | 0.68 |
| srh-204 | 0.72 | 0.39 | 0.13 | 0.21 | 0.33 | 0.75 |
| srh-206 | 0.53 | 0.43 | 0.59 | 0.24 | 0.27 | 0.61 |
| srh-207 | 0.75 | 0.68 | 0.44 | 0.78 | 0.71 | 0.72 |
| srh-208 | 0.82 | 0.83 | 0.78 | 0.68 | 0.67 | 0.82 |
| srh-209 | 0.29 | −0.20 | 0.48 | 0.18 | 0.18 | 0.62 |
| srh-210 | 0.92 | 0.66 | 0.67 | 0.38 | 0.47 | 0.45 |
| srh-214 | 0.63 | 0.57 | 0.85 | 0.88 | 0.72 | 0.78 |
| srh-216 | 0.76 | 0.47 | 0.86 | 0.65 | 0.60 | 0.73 |
| srh-217 | −0.12 | 0.76 | 0.69 | 0.92 | 0.94 | 0.60 |
| srh-220 | 0.81 | 0.61 | 0.81 | 0.67 | 0.40 | 0.52 |
| srh-222 | 0.80 | 0.76 | 0.62 | 0.46 | 0.65 | 0.58 |
| srh-223 | 0.51 | 0.49 | 0.88 | 0.23 | 0.43 | 0.76 |
| srh-227 | 0.43 | 0.56 | 0.37 | 0.60 | 0.35 | 0.76 |
| srh-229 | −0.20 | −0.21 | 0.60 | 0.12 | 0.09 | 0.69 |
| srh-233 | 0.36 | −0.11 | 0.50 | 0.33 | 0.49 | 0.38 |
| srh-235 | 0.64 | 0.32 | 0.76 | 0.51 | 0.73 | 0.58 |
| srh-236 | 0.41 | 0.31 | 0.71 | 0.37 | 0.44 | 0.64 |
| srh-239 | 0.57 | 0.34 | 0.59 | 0.49 | 0.54 | 0.84 |
| srh-241 | 0.63 | 0.66 | 0.63 | 0.63 | 0.78 | 0.85 |
| srh-243 | 0.46 | 0.30 | 0.72 | 0.00 | 0.48 | 0.63 |
| srh-244 | 0.74 | 0.43 | 0.73 | 0.19 | 0.34 | 0.76 |
| srh-247 | 0.60 | 0.40 | 0.85 | 0.38 | 0.49 | 0.54 |
| srh-250 | 0.47 | 0.40 | 0.79 | 0.58 | 0.55 | 0.58 |
| srh-251 | 0.75 | 0.70 | 0.92 | 0.32 | 0.32 | 0.64 |
| srh-252 | 0.59 | 0.71 | 0.86 | 0.65 | 0.87 | 0.64 |
| srh-258 | 0.78 | 0.40 | 0.56 | 0.35 | 0.44 | 0.75 |
| srh-261 | 0.51 | 0.45 | 0.60 | 0.27 | 0.57 | 0.72 |
| srh-264 | 0.61 | 0.38 | 0.56 | 0.46 | 0.85 | 0.74 |
| srh-266 | 0.25 | 0.32 | −0.31 | 0.00 | −0.14 | 0.25 |

TABLE 3-continued

| | | | | | | |
|---|---|---|---|---|---|---|
| srh-274 | 0.44 | 0.45 | −0.59 | 0.82 | 0.12 | 0.60 |
| srh-275 | 0.39 | 0.16 | −0.29 | 0.57 | 0.42 | 0.53 |
| srh-276 | 0.58 | 0.56 | 0.30 | 0.45 | 0.44 | 0.59 |
| srh-277 | 0.54 | 0.49 | −0.09 | 0.83 | 0.81 | 0.65 |
| srh-279 | 0.53 | 0.34 | 0.89 | 0.55 | 0.37 | 0.61 |
| srh-281 | 0.51 | 0.33 | 0.49 | 0.64 | 0.01 | 0.55 |
| srh-282 | 0.52 | 0.24 | 0.80 | 0.73 | 0.55 | 0.79 |
| srh-283 | 0.34 | 0.21 | 0.65 | 0.15 | 0.26 | 0.56 |
| srh-284 | 0.73 | 0.29 | 0.73 | 0.36 | 0.49 | 0.59 |
| srh-291 | 0.80 | 0.58 | 0.86 | 0.48 | 0.82 | 0.91 |
| srh-292 | 0.43 | 0.48 | 0.80 | 0.52 | 0.43 | 0.78 |
| srh-293 | 0.71 | 0.31 | 0.75 | 0.00 | 0.59 | 0.82 |
| srh-297 | 0.42 | 0.63 | 0.84 | 0.32 | 0.29 | 0.56 |
| srh-298 | 0.68 | 0.66 | 0.65 | 0.68 | 0.33 | 0.82 |
| srh-308 | 0.56 | 0.14 | 0.04 | 0.39 | 0.15 | 0.30 |

| | Nona | Oct | High Iaa | High Bz | High Da |
|---|---|---|---|---|---|
| Control | −0.91 ± 0.009 | −0.68 ± 0.013 | −0.84 ± 0.011 | −0.91 ± 0.007 | −0.62 ± 0.012 |
| srh-4 | −0.87 | −0.17 | −0.73 | −0.75 | −0.81 |
| srh-7 | −0.78 | −0.65 | −0.86 | −1.00 | −0.83 |
| srh-8 | −0.86 | −0.80 | −0.94 | −0.93 | −0.63 |
| srh-10 | −0.88 | −0.45 | −0.96 | −0.95 | 0.20 |
| srh-11 | −0.65 | −0.19 | −0.79 | −0.78 | −0.65 |
| srh-15 | −0.25 | −0.85 | −0.60 | −0.41 | −0.54 |
| srh-16 | −0.63 | −0.89 | −0.74 | −0.88 | −0.65 |
| srh-18 | −0.26 | −0.65 | −0.78 | −0.88 | −0.74 |
| srh-19 | −0.80 | −0.33 | −0.89 | −1.00 | −0.43 |
| srh-22 | −0.89 | −0.48 | −0.81 | −0.80 | −0.74 |
| srh-23 | −0.77 | −0.90 | −0.88 | −0.88 | −0.87 |
| srh-24 | −0.79 | −0.56 | −1.00 | −1.00 | −0.67 |
| srh-25 | −0.06 | −0.90 | 0.13 | −0.73 | −0.22 |
| srh-27 | −0.79 | −0.68 | −0.92 | 0.96 | −0.80 |
| srh-28 | −0.71 | −0.73 | −0.64 | −0.75 | −0.58 |
| srh-36 | −0.57 | −0.72 | −0.59 | −0.95 | −0.46 |
| srh-37 | −0.89 | −0.88 | −0.69 | −1.00 | −0.34 |
| srh-39 | −0.90 | −0.50 | −0.79 | −0.84 | −0.51 |
| srh-40 | −0.83 | −0.92 | −0.88 | −0.87 | −0.46 |
| srh-41 | −0.62 | −0.80 | −0.56 | −0.89 | −0.21 |
| srh-44 | −0.58 | −0.52 | 0.00 | −0.48 | −0.25 |
| srh-45 | −0.91 | −0.87 | −0.97 | −0.96 | −0.47 |
| srh-46 | −0.87 | −0.87 | −0.91 | −0.82 | −0.82 |
| srh-48 | −0.79 | −0.83 | −0.67 | −0.80 | −0.49 |
| srh-49 | −0.91 | −0.57 | −0.59 | −0.76 | −0.62 |
| srh-50 | −0.96 | −0.89 | −0.93 | −1.00 | −0.52 |
| srh-51 | −0.90 | −0.89 | −0.85 | −0.96 | −0.73 |
| srh-52 | −0.85 | −0.79 | −0.96 | −1.00 | −0.78 |
| srh-55 | −0.96 | −0.95 | −0.95 | −0.98 | −0.78 |
| srh-59 | −0.79 | −0.55 | −0.87 | −0.91 | −0.24 |
| srh-60 | −0.83 | −0.52 | −0.77 | −0.98 | −0.64 |
| srh-61 | −0.68 | −0.77 | −0.82 | −0.92 | −0.57 |
| srh-67 | −0.61 | −0.66 | −0.96 | −0.97 | −0.58 |
| srh-68 | −0.65 | −0.79 | −0.67 | −0.87 | −0.49 |
| srh-69 | −0.84 | −0.61 | −0.94 | −0.87 | −0.76 |
| srh-70 | −0.81 | −0.80 | −0.40 | −0.94 | −0.87 |
| srh-71 | −0.80 | −0.60 | −0.76 | −0.91 | −0.38 |
| srh-72 | −0.87 | −0.62 | −0.55 | −0.98 | −0.73 |
| srh-74 | −0.96 | −0.89 | −0.51 | −0.95 | −0.54 |
| srh-75 | −0.86 | −0.59 | −0.50 | −0.94 | −0.42 |
| srh-77 | −0.74 | −0.31 | −0.68 | −0.89 | −0.34 |
| srh-79 | −0.61 | −0.17 | −0.22 | −0.80 | 0.35 |
| srh-80 | −0.81 | −0.39 | −0.31 | −0.87 | −0.48 |
| srh-82 | −0.96 | −0.65 | −0.53 | −0.88 | −0.36 |
| srh-83 | −0.70 | −0.33 | 0.34 | −0.45 | −0.23 |
| srh-97 | −0.66 | −0.64 | −0.51 | −0.86 | −0.42 |
| srh-99 | −0.82 | −0.61 | −0.33 | −0.74 | −0.24 |
| srh-100 | −0.48 | −0.46 | −0.64 | −0.94 | −0.75 |
| srh-104 | −0.71 | −0.36 | −0.48 | −0.91 | −0.39 |
| srh-105 | −0.80 | −0.61 | −0.76 | −0.96 | −0.58 |
| srh-109 | −0.84 | −0.91 | −0.68 | −0.87 | −0.59 |
| srh-111 | −0.71 | −0.44 | −0.08 | −0.79 | −0.35 |
| srh-113 | −0.91 | −0.43 | −0.36 | −0.95 | −0.62 |
| srh-115 | −0.75 | −0.82 | −0.38 | −0.89 | −0.57 |
| srh-116 | −0.69 | −0.82 | −0.45 | −0.91 | −0.36 |
| srh-118 | −0.89 | −0.37 | −0.54 | −0.82 | −0.64 |
| srh-119 | −0.84 | −0.35 | −0.83 | −0.93 | −0.78 |
| srh-120 | −0.68 | −0.37 | −0.80 | −0.89 | −0.66 |
| srh-122 | −0.84 | −0.61 | −0.84 | −0.74 | −0.53 |
| srh-123 | −0.90 | −0.32 | −0.49 | −0.93 | −0.55 |
| srh-125 | −0.77 | −0.56 | −0.69 | −0.96 | −0.59 |

TABLE 3-continued

| srh-128 | −0.89 | −0.47 | −0.53 | −0.95 | −0.48 |
|---|---|---|---|---|---|
| srh-129 | −0.90 | −0.56 | −0.72 | −0.91 | −0.69 |
| srh-130 | −0.94 | −0.68 | −0.76 | −0.73 | −0.37 |
| srh-131 | −0.45 | −0.49 | −0.57 | −0.63 | −0.34 |
| srh-132 | −0.84 | −0.19 | −0.89 | −1.00 | −0.83 |
| srh-139 | −0.91 | −0.73 | −0.39 | −0.94 | −0.42 |
| srh-140 | −0.80 | −0.78 | −0.67 | −0.87 | −0.46 |
| srh-141 | −0.94 | −0.49 | −0.87 | −0.98 | −0.77 |
| srh-142 | −0.94 | −0.59 | −0.90 | −0.89 | −0.49 |
| srh-145 | −0.44 | −0.64 | −0.87 | −0.90 | −0.85 |
| srh-148 | −0.78 | −0.67 | −0.71 | −0.89 | −0.69 |
| srh-154 | −0.58 | −0.65 | −0.75 | −0.82 | −0.65 |
| srh-159 | −0.48 | −0.79 | −0.94 | −0.74 | −0.45 |
| srh-165 | −0.40 | −0.49 | −0.58 | −0.87 | −0.79 |
| srh-166 | −1.00 | −0.74 | −0.76 | −0.83 | −0.83 |
| srh-167 | −1.00 | −0.28 | −0.44 | −0.83 | −0.89 |
| srh-169 | −0.92 | −0.62 | −0.90 | −1.00 | −0.92 |
| srh-174 | −0.92 | −0.45 | −0.92 | −0.89 | −0.69 |
| srh-179 | −0.97 | −0.60 | −0.83 | −0.95 | −0.87 |
| srh-182 | −0.98 | −0.86 | −0.46 | −0.94 | −0.86 |
| srh-186 | −0.93 | −0.64 | −0.92 | −0.94 | −0.80 |
| srh-190 | −1.00 | −0.64 | −0.82 | −0.97 | −0.91 |
| srh-193 | −0.84 | −0.92 | −0.88 | −0.90 | −0.53 |
| srh-195 | −0.98 | −0.47 | −0.90 | −0.89 | −0.80 |
| srh-201 | −0.97 | −0.93 | −0.93 | −1.00 | −0.95 |
| srh-203 | −1.00 | −0.95 | −0.79 | −0.98 | −0.94 |
| srh-204 | −1.00 | −0.90 | −0.89 | −1.00 | −0.89 |
| srh-206 | −1.00 | −0.94 | −0.82 | −0.97 | −0.79 |
| srh-207 | −1.00 | −0.81 | −0.88 | −1.00 | −0.87 |
| srh-208 | −0.82 | −0.60 | −0.96 | −0.93 | −0.76 |
| srh-209 | −0.84 | −0.85 | −0.85 | −0.85 | −0.70 |
| srh-210 | −0.66 | −0.77 | −0.82 | −0.96 | −0.56 |
| srh-214 | −0.96 | −0.98 | −0.93 | −0.66 | −0.60 |
| srh-216 | −0.83 | −0.68 | −0.95 | −0.95 | −0.61 |
| srh-217 | −0.44 | −0.82 | −0.93 | −0.92 | −0.50 |
| srh-220 | −0.28 | −0.47 | −0.53 | −0.84 | −0.42 |
| srh-222 | −0.82 | −0.77 | −0.91 | −0.85 | −0.66 |
| srh-223 | −0.74 | −0.75 | −0.78 | −0.73 | −0.50 |
| srh-227 | −0.59 | −0.43 | −0.37 | −0.75 | −0.41 |
| srh-229 | −0.27 | −0.70 | −0.89 | −1.00 | −0.66 |
| srh-233 | −0.21 | −0.17 | −0.74 | −0.92 | −0.70 |
| srh-235 | −0.24 | −0.23 | −0.81 | −0.94 | −0.29 |
| srh-236 | −0.25 | −0.44 | −0.55 | −0.80 | −0.41 |
| srh-239 | −0.61 | −0.58 | −0.68 | −0.98 | −0.45 |
| srh-241 | −0.76 | −0.64 | −0.85 | −0.82 | −0.70 |
| srh-243 | −0.98 | −0.89 | −0.89 | −0.88 | −0.70 |
| srh-244 | −0.79 | −0.74 | −0.86 | −0.91 | −0.59 |
| srh-247 | −0.81 | −0.55 | −0.93 | −0.45 | −0.70 |
| srh-250 | −0.90 | −0.58 | −0.93 | −0.94 | −0.75 |
| srh-251 | −0.80 | −0.76 | −0.84 | −0.92 | −0.68 |
| srh-252 | −0.67 | −0.74 | −0.96 | −0.96 | −0.47 |
| srh-258 | −0.92 | −0.57 | −0.96 | −0.94 | −0.83 |
| srh-261 | −0.86 | −0.70 | −0.81 | −0.92 | −0.65 |
| srh-264 | −0.88 | −0.50 | −0.91 | −0.79 | −0.52 |
| srh-266 | −0.97 | −0.52 | −0.92 | −0.95 | −0.74 |
| srh-274 | −0.93 | −0.83 | −0.93 | −0.97 | −0.65 |
| srh-275 | −0.97 | −0.84 | −0.79 | −0.90 | −0.59 |
| srh-276 | −1.00 | −0.81 | −0.87 | −1.00 | −0.24 |
| srh-277 | −1.00 | −0.77 | −0.79 | −0.94 | −0.92 |
| srh-279 | −0.91 | −0.57 | −0.92 | −0.96 | −0.76 |
| srh-281 | −0.88 | 0.03 | −0.62 | −0.79 | −0.52 |
| srh-282 | −0.83 | −0.70 | −0.89 | −1.00 | −0.65 |
| srh-283 | −0.89 | −0.29 | −0.73 | −0.88 | −0.86 |
| srh-284 | −0.89 | −0.41 | −0.79 | −0.84 | −0.48 |
| srh-291 | −0.81 | −0.12 | −0.47 | −0.80 | −0.59 |
| srh-292 | −0.86 | −0.62 | −0.59 | −0.93 | −0.55 |
| srh-293 | −0.81 | −0.50 | −0.70 | −0.96 | −0.70 |
| srh-297 | −0.94 | −0.80 | 0.17 | −0.90 | −0.42 |
| srh-298 | −0.37 | −0.50 | −0.83 | −0.94 | −0.68 |
| srh-308 | −0.87 | −0.63 | −0.86 | −0.86 | −0.62 |

Table 3. Raw data regarding RNAi screening of srh olfactory receptor family genes The chemotaxis indices of nematodes, the srh family genes of which were RNAi-treated in the first (A), second (B), and third (C) screenings, to 11 odorants. The 11 odorants include: low concentrations of six attractants [isoamyl alcohol (Iaa), benzaldehyde (Bz), butanone (Bu), pentanedione (Pd), pyrazine (Pz) and trimethylthiazole (Tmt)]; two repellents [nonanone (Nona) and octanol (Oct)]; and high concentrations of three attractants [isoamyl alcohol (high Iaa), benzaldehyde (high Bz), and diacetyl (high Da)]. The blue, orange and green shades indicate statistical differences, respectively, compared with the control value on the same date, compared with the average of control values on all days, and compared with both of these values (see the section "Materials and method").

TABLE 4

| Gene | Odorant | 1st | 2nd | 3rd |
|---|---|---|---|---|
| sra-1 | high Da | −0.22 | −0.09 | −0.71 |
| sra-2 | high Da | −0.56 | −0.31 | −0.63 |
| sra-6 | Bu | −0.73 | −0.15 | 0.44 |
| sra-7 | high Da | 0.46 | −0.47 | −0.29 |
| sra-8 | high Da | −0.12 | −0.32 | −0.62 |
| sra-9 | high Da | −0.43 | −0.59 | −0.67 |
| sra-12 | Pz | 0.45 | −0.37 | 0.52 |
| sra-17 | Iaa | 0.33 | −0.26 | 0.08 |
| sra-18 | Bz | 0.24 | −0.14 | 0.29 |
|  | Tmt | 0.19 | 0.18 | 0.44 |
| sra-20 | Bz | 0.28 | −0.19 | 0.12 |
|  | Pz | −0.16 | 0.10 | 0.36 |
|  | Nona | −0.52 | −0.90 | −0.84 |
| sra-24 | Iaa | 0.34 | 0.29 | 0.38 |
|  | Pz | −0.02 | 0.14 | 0.76 |
|  | Tmt | −0.27 | 0.35 | 0.64 |
| sra-26 | Pz | 0.21 | 0.47 | 0.72 |
| sra-27 | Pz | 0.26 | 0.32 | 0.57 |
| sra-38 | high Bz | −0.87 | −0.65 | −0.19 |
| srd-5 | Bu | −0.36 | −0.45 | 0.29 |
| srd-15 | Tmt | 0.60 | 0.14 | 0.63 |
| srd-17 | Iaa | 0.71 | 0.43 | 0.48 |
|  | Pz | 0.53 | 0.19 | 0.13 |
|  | Tmt | 0.59 | −0.27 | 0.49 |
| srd-18 | Bz | 0.30 | 0.02 | −0.17 |
| srd-19 | Pz | 0.39 | 0.09 | 0.23 |
| srd-21 | high Da | −0.49 | −0.45 | −0.71 |
| srd-23 | Pz | 0.31 | 0.22 | 0.50 |
|  | Oct | 0.03 | −0.51 | −0.36 |
| srb-1 | Pd | 0.55 | 0.12 | 0.22 |
| srb-2 | Pz | 0.49 | 0.15 | 0.45 |
| srv-11 | Pd | 0.38 | 0.14 | 0.21 |
| srv-12 | high Bz | −0.91 | −0.56 | 0.53 |
| srxa-3 | Pz | 0.54 | 0.47 | 0.45 |
| srxa-9 | Pd | 0.24 | 0.46 | 0.14 |
| srxa-14 | Pd | 0.70 | 0.37 | 0.37 |
| srz-1 | Pz | 0.51 | 0.36 | 0.39 |
| srz-2 | Pz | 0.63 | −0.09 | 0.40 |
|  | Tmt | 0.66 | −0.40 | 0.51 |
| srz-6 | Pd | 0.30 | 0.57 | −0.30 |
| srz-10 | Bz | 0.61 | −0.06 | 0.16 |
| srz-47 | high Da | −0.44 | −0.57 | −0.71 |
| srz-48 | Bz | 0.42 | 0.02 | −0.07 |
|  | Pd | 0.68 | 0.21 | 0.08 |
|  | high Bz | −0.87 | −0.41 | −0.90 |
| srz-66 | high Da | −0.14 | −0.58 | −0.76 |
| srz-94 | Pz | 0.49 | 0.38 | 0.25 |
| srz-95 | Pz | 0.34 | 0.17 | 0.37 |
|  | Tmt | 0.52 | −0.11 | 0.47 |
| srbc-3 | Pd | 0.10 | 0.24 | −0.04 |
| srbc-11 | Pd | 0.17 | 0.17 | 0.04 |
| srbc-29 | Oct | −0.29 | −0.29 | −0.48 |
| srbc-61 | Bz | 0.30 | 0.21 | 0.11 |
| srbc-66 | Bz | 0.47 | 0.29 | 0.04 |
| srbc-75 | Pd | 0.58 | 0.13 | 0.36 |
| srbc-82 | Bz | 0.29 | 0.13 | 0.45 |
| srsx-11 | Pd | 0.76 | −0.55 | −0.83 |
| srsx-26 | Bu | −0.44 | −0.54 | −0.32 |
| srsx-32 | Pz | 0.30 | 0.09 | 0.46 |
| srsx-33 | Pd | 0.57 | 0.06 | 0.28 |
|  | Pz | 0.52 | 0.30 | 0.42 |
| srsx-34 | Bz | 0.04 | 0.07 | 0.43 |
| srsx-37 | Pd | 0.52 | 0.49 | 0.27 |
| srr-1 | Pz | 0.39 | 0.56 | 0.39 |
| srr-8 | Pd | 0.28 | 0.49 | 0.19 |
| srr-9 | Pz | 0.26 | 0.54 | −0.01 |
| srw-22 | Bu | −0.32 | −0.42 | −0.32 |
| srw-24 | Pd | 0.28 | 0.56 | 0.45 |
|  | Oct | −0.51 | −0.30 | −0.28 |
| srw-26 | Pd | 0.25 | −0.31 | 0.36 |
| srw-29 | Bz | 0.33 | −0.41 | 0.50 |
|  | Bu | −0.24 | −0.46 | −0.31 |
| srw-31 | Bu | −0.15 | −0.61 | −0.48 |
| srw-33 | Pz | −0.51 | 0.49 | 0.37 |

46

TABLE 4-continued

| Gene | Odorant | 1st | 2nd | 3rd |
|---|---|---|---|---|
| srw-58 | Oct | −0.39 | −0.33 | −0.43 |
| srw-117 | Bz | 0.26 | −0.25 | 0.26 |
| srw-121 | Bu | −0.26 | −0.54 | −0.38 |
| srw-132 | Bu | −0.23 | −0.64 | −0.36 |
| srw-142 | Pz | 0.27 | 0.38 | 0.31 |
| sru-4 | Iaa | 0.13 | 0.23 | 0.74 |
| sru-12 | Iaa | 0.42 | 0.06 | 0.64 |
| sru-31 | Pd | 0.17 | −0.05 | 0.23 |
| sru-37 | Bu | −0.51 | −0.23 | −0.53 |
| sru-38 | Bu | −0.57 | −0.12 | −0.33 |
| srh-7 | Bz | 0.92 | 0.33 | 0.33 |
| srh-10 | Iaa | −0.12 | 0.44 | 0.19 |
|  | Bz | 0.12 | 0.26 | 0.13 |
|  | Pd | 0.68 | 0.06 | −0.07 |
|  | Pz | 0.67 | 0.50 | 0.25 |
| srh-18 | Tmt | 0.91 | 0.52 | −0.07 |
| srh-25 | high Da | −0.22 | −0.49 | 0.32 |
| srh-27 | Bz | −0.16 | −0.08 | 0.20 |
|  | Pz | 0.32 | −0.07 | 0.21 |
| srh-28 | Iaa | 0.63 | −0.10 | 0.41 |
|  | Pd | 0.22 | −0.31 | 0.14 |
|  | Tmt | 0.92 | 0.26 | 0.49 |
| srh-39 | Bz | −0.08 | −0.33 | −0.09 |
| srh-40 | Iaa | 0.79 | 0.07 | 0.51 |
|  | Bz | 0.50 | −0.28 | −0.02 |
| srh-59 | Tmt | 0.37 | 0.69 | 0.69 |
| srh-68 | Pd | 0.21 | 0.39 | 0.08 |
| srh-79 | high Da | 0.35 | −0.63 | −0.68 |
| srh-111 | Bz | 0.10 | 0.13 | 0.20 |
| srh-119 | Bz | −0.22 | −0.63 | 0.18 |
|  | Oct | −0.35 | −0.60 | −0.39 |
| srh-139 | Pd | 0.06 | 0.41 | 0.09 |
| srh-140 | Bz | 0.07 | −0.25 | 0.45 |
| srh-214 | high Da | −0.60 | −0.63 | −0.63 |
| srh-216 | high Da | −0.61 | −0.78 | −0.77 |
| srh-236 | high Da | −0.41 | −0.67 | −0.67 |
| srh-276 | Pz | 0.44 | −0.24 | 0.44 |
| srh-281 | Pz | 0.01 | 0.42 | 0.74 |
|  | high Da | −0.52 | −0.42 | −0.60 |
| srh-283 | Oct | −0.29 | −0.78 | −0.54 |
| srh-292 | Pz | 0.43 | 0.12 | 0.68 |
| srh-293 | Pd | 0.00 | 0.21 | −0.21 |
| srh-297 | Pz | 0.29 | −0.12 | 0.46 |
| srh-298 | Oct | −0.50 | −0.81 | 0.81 |
| srh-308 | Pz | 0.15 | 0.29 | 0.36 |
| sri-6 | Pd | 0.42 | −0.20 | 0.13 |
|  | Pz | 0.33 | 0.07 | 0.56 |
| sri-13 | Bz | 0.23 | 0.28 | 0.26 |
| sri-14 | high Da | −0.36 | −0.46 | −0.62 |
| sri-17 | Pz | 0.36 | 0.30 | 0.30 |
| sri-21 | high Da | −0.76 | −0.59 | −0.68 |
| sri-36 | Pz | −0.05 | 0.18 | 0.50 |
| sri-38 | Bz | 0.19 | −0.33 | 0.15 |
| sri-43 | Pd | 0.27 | −0.20 | 0.23 |
| sri-47 | Pz | 0.50 | −0.54 | 0.47 |
|  | Tmt | 0.96 | 0.13 | 0.45 |
| sri-51 | Bz | 0.21 | 0.05 | −0.01 |
|  | Pz | 0.14 | −0.39 | 0.43 |
| sri-69 | Tmt | 0.32 | 0.20 | 0.74 |
| srj-14 | Bz | 0.06 | −0.17 | 0.12 |
|  | Bu | 0.54 | 0.57 | 0.06 |
| srj-22 | Bz | −0.21 | 0.25 | 0.27 |
|  | Bu | 0.31 | 0.47 | −0.06 |
|  | Pd | 0.11 | 0.17 | 0.46 |
| srj-23 | Tmt | 0.30 | 0.24 | 0.25 |
| srj-26 | Tmt | 0.18 | 0.54 | 0.65 |
| srj-27 | Bu | 0.58 | 0.60 | −0.42 |
|  | Pd | 0.29 | 0.17 | 0.37 |
| srj-39 | Oct | −0.38 | −0.43 | −0.42 |
| srj-57 | Bu | 0.15 | 0.46 | −0.39 |
| sre-13 | high Da | −0.32 | −0.56 | −0.65 |
| sre-23 | Pz | 0.38 | −0.05 | 0.09 |
| sre-26 | Tmt | 0.42 | 0.50 | 0.58 |
| sre-37 | Bz | 0.00 | 0.15 | 0.26 |
| sre-38 | Bz | 0.12 | 0.19 | 0.27 |
| sre-54 | high Da | −0.36 | −0.35 | −0.72 |
| sre-56 | Pd | −0.18 | −0.58 | 0.28 |
|  | high Da | −0.38 | −0.29 | −0.77 |

TABLE 4-continued

| Gene | Odorant | 1st | 2nd | 3rd |
|---|---|---|---|---|
| srab-4 | Pd | 0.00 | -0.56 | 0.12 |
| srab-7 | Bz | 0.16 | -0.18 | -0.48 |
|  | Pd | 0.00 | 0.13 | -0.43 |
|  | Pz | 0.11 | 0.17 | -0.15 |
| srab-13 | Bz | 0.16 | -0.21 | -0.30 |
| srab-18 | Pd | 0.17 | 0.00 | 0.15 |
| srab-20 | Pd | -0.01 | 0.07 | 0.22 |
| srx-2 | Pd | -0.29 | -0.14 | -0.39 |
| srx-13 | laa | 0.10 | -0.31 | 0.43 |
|  | Pz | -0.15 | 0.18 | 0.43 |
| srx-46 | Pz | 0.08 | 0.21 | 0.48 |
| srx-47 | high Da | -0.60 | -0.19 | -0.69 |
| srx-118 | high Da | -0.62 | -0.29 | -0.53 |
| srt-18 | high Da | -0.38 | -0.09 | -0.57 |
| srt-25 | high Da | -0.42 | -0.36 | -0.37 |
| srt-35 | Pz | 0.07 | 0.22 | 0.46 |
| srg-10 | Pz | 0.13 | 0.46 | 0.25 |
| srg-13 | Pz | 0.22 | 0.06 | 0.44 |
| srg-20 | Pz | 0.31 | 0.44 | -0.05 |
| srg-37 | Pz | 0.43 | -0.10 | 0.40 |
| srg-46 | Pz | 0.03 | 0.25 | 0.45 |
| srg-51 | Pz | -0.07 | 0.37 | 0.46 |
| srg-56 | Bu | 0.52 | 0.40 | -0.31 |
| srg-64 | laa | 0.22 | -0.09 | 0.30 |
|  | Bz | -0.14 | -0.03 | 0.41 |
| str-1 | Pz | -0.32 | 0.28 | 0.46 |
| str-2 | laa | 0.84 | 0.46 | 0.63 |
|  | Bz | 0.68 | 0.23 | 0.19 |
|  | high Da | -0.63 | -0.62 | -0.63 |
| str-5 | Bz | 0.55 | 0.12 | 0.48 |
| str-10 | Oct | 0.35 | -0.61 | -0.48 |
| str-18 | Bz | 0.14 | 0.20 | 0.13 |
| str-19 | Bz | -0.11 | -0.25 | 0.01 |
| str-20 | Pz | 0.35 | 0.14 | 0.47 |
| str-23 | Pd | 0.36 | 0.35 | -0.07 |
| str-30 | Bz | -0.10 | -0.03 | 0.22 |
|  | Pz | 0.43 | -0.03 | 0.49 |
| str-31 | Bz | -0.19 | 0.13 | -0.17 |
|  | Pd | 0.37 | 0.29 | 0.13 |
|  | Pz | 0.22 | 0.21 | 0.44 |
| str-32 | laa | 0.68 | 0.10 | 0.20 |
|  | Bz | -0.49 | 0.39 | 0.18 |
|  | Pz | -0.19 | 0.32 | 0.31 |
| str-37 | Bz | 0.41 | 0.38 | -0.39 |
| str-38 | Bz | -0.54 | 0.44 | -0.63 |
| str-40 | laa | 0.73 | 0.16 | -0.08 |
|  | Pz | 0.40 | -0.06 | 0.36 |
| str-55 | high Da | -0.30 | -0.20 | -0.70 |
| str-63 | Pz | 0.56 | 0.15 | 0.57 |
| str-71 | high Bz | 0.22 | -0.87 | -0.76 |
| str-74 | Pz | 0.40 | 0.04 | 0.21 |
| str-78 | high Bz | -0.89 | -0.87 | -0.74 |
| str-82 | Pz | 0.48 | 0.43 | 0.30 |
| str-92 | Nona | -0.82 | -0.88 | -0.77 |
| str-94 | Pd | 0.46 | 0.30 | 0.09 |
| str-96 | high Da | -0.55 | -0.43 | -0.76 |
| str-106 | Bz | 0.09 | 0.00 | 0.02 |
|  | Pd | 0.15 | -0.40 | -0.35 |
|  | Tmt | -0.20 | 0.38 | 0.18 |
| str-112 | Pd | 0.44 | 0.25 | -0.13 |
| str-113 | laa | 0.58 | 0.43 | -0.67 |
| str-115 | Pz | 0.09 | 0.56 | 0.41 |
|  | Tmt | 0.04 | 0.49 | 0.47 |
| str-116 | laa | 0.19 | 0.27 | 0.30 |
|  | Tmt | 0.15 | 0.54 | 0.58 |
| str-118 | laa | 0.00 | 0.41 | 0.41 |
| str-122 | Tmt | 0.25 | 0.66 | 0.53 |
| str-123 | Bz | 0.10 | 0.02 | 0.24 |
|  | Pd | 0.18 | 0.22 | 0.12 |
|  | Tmt | 0.22 | 0.30 | 0.52 |
| str-129 | Bz | 0.33 | 0.07 | -0.21 |
|  | Pd | 0.02 | 0.21 | -0.15 |
|  | Tmt | 0.21 | 0.32 | 0.51 |
| str-130 | laa | 0.83 | 0.30 | 0.35 |
| str-136 | Pd | 0.11 | 0.37 | 0.09 |
| str-139 | Pd | -0.27 | 0.21 | 0.29 |
| str-144 | laa | 0.47 | 0.30 | 0.41 |
| str-146 | laa | 0.48 | 0.67 | 0.45 |

TABLE 4-continued

| Gene | Odorant | 1st | 2nd | 3rd |
|---|---|---|---|---|
| str-148 | Bz | 0.30 | -0.17 | 0.26 |
| str-149 | Bz | 0.27 | 0.23 | 0.11 |
|  | Bu | -0.93 | -0.10 | -0.56 |
| str-150 | Bu | -0.50 | -0.23 | -0.93 |
| str-151 | Oct | -0.14 | -0.33 | -0.03 |
| str-165 | Bz | 0.45 | 0.14 | 0.24 |
| str-196 | high Da | -0.29 | -0.12 | -0.72 |
| str-199 | high Da | -0.74 | -0.20 | -0.88 |
| str-209 | Bz | 0.00 | 0.37 | -0.09 |
|  | high Da | -0.42 | -0.32 | -0.79 |
| str-211 | Nona | -1.00 | -0.81 | -0.59 |
|  | high laa | -0.87 | -0.80 | -0.82 |
| str-217 | Bz | -0.14 | 0.25 | 0.41 |
|  | Pz | 0.53 | 0.29 | 0.37 |
|  | Tmt | 0.76 | -0.24 | 0.21 |
| str-220 | laa | 0.52 | 0.02 | -0.22 |
|  | Bz | 0.75 | -0.35 | 0.12 |
|  | Pz | 0.56 | -0.53 | -0.08 |
|  | Tmt | 0.33 | -0.33 | 0.39 |
| str-223 | Bz | 0.10 | 0.22 | -0.61 |
| str-225 | Bz | 0.34 | -0.38 | 0.43 |
| str-231 | Oct | -0.80 | -0.69 | 0.03 |
| str-256 | Pz | 0.30 | 0.38 | 0.61 |
| str-264 | Bz | 0.46 | 0.13 | 0.50 |

Table 4. Raw data regarding RNAi screening of 194 candidate olfactory receptor genes After the third screening, a total of 194 olfactory receptor candidate genes were obtained. This table shows the chemotaxis indices of nematodes, in which these genes were RNAi-treated in the first, second, and third screenings. It was shown that some genes are associated with detection of a plurality of odorants.

TABLE 5

| Genes | Odorants | Cells |
|---|---|---|
|  |  | Reporter gene analysis-this study |
| sra-17 | laa | AWA, several neurons |
| sru-4 | laa | ADL |
| srd-17 | laa, Tmt | AWC |
| srh-10 | laa, Bz, Pd, Pz | ASH, ASJ |
| srh-68 | Pd | ADL, several neurons |
| srh-139 | Pd | ADL, several neurons |
| srsx-37 | Pd | ADL |
| srv-11 | Pd | ASH |
| srz-6 | Pd | ADL |
| srz-1 | Pz | ASH, ADL |
| srh-18 | Tmt | ASH, PHA, PHB |
| srx-47 | High Da | ASH, AWA |
| sri-14 | High Da | ASH, AWC |
| srh-25 | High Da | ADL |
| srh-281 | High Da | ADL |
| srw-29 | Bu | Sheath cell |
|  |  | Expression from WormBase |
| srh-28 | laa, Pd, Pz, Tmt, Oct, Da | Head neurons |
| srab-13 | Bz | Head neurons, developing vulva, hypodermis |
| sra-38 | Bz | Head neurons, pharynx, unidentified head cells |
| srab-7 | Bz, Pd, Pz, | Amphids, head neurons, intestinal, depressor muscle, vulva muscle |
| sra-20 | Bz, Pz, Nona | Head neurons |
| sra-6 | Bu | Head neurons, mechanosensory neurons, unidentified head cells, unidentified tail cells |
| sru-38 | Bu | Amphids, phasmids, head neurons, tail neurons, intestinal cells |
| srxa-14 | Pd | Head neurons, pharynx, intestinal, rectal gland cells, hypodermis |

TABLE 5-continued

| Genes | Odorants | Cells |
|---|---|---|
| srxa-3 | Pz | Head neurons, tail neurons, intestinal cells |
| srg-13 | Pz | Body neurons, tail neurons |
| srh-281 | Pz, Da | Head neurons |
| srd-15 | Tmt | Phasmids, head neurons, tail neurons, pharynx, intestinal, spermatheca-uterine valve |
| srh-79 | Da | Amphids, phasmids, head neurons, tail neurons |
| sra-7 | Da | Head neurons, unidentified head cells, unidentified tail cells |
| srx-47 | Da | Amphids, head neurons, intestinal, unidentified tail cells |
| srj-57 | Bu | Intestinal cells |
| srz-94 | Pz | Intestinal cells, hypodermis, seam cells |
| str-115 | Pz, Tmt | Intestinal cells |
| sra-2 | Da | Intestinal muscle, anal depressor muscle, hypodermis, unidentified head cells |

Table 5. Expression patterns of 35 receptor candidate genes and relevant odorants Only the sensory neurons are listed with their names. Other neurons are listed as several neurons belonging to a single group. For photographs showing the expression of the analyzed genes, see FIG. 23. The genes written with bold-face letters indicate genes, which were expressed (based on the expression of a reporter gene) in neurons exhibiting a chemosensory response to diacetyl when were ablated. Bu, butanone; Bz, benzaldehyde; Da, diacetyl; Iaa, isoamyl alcohol; Nona, nonanone; Oct, octanol; Pd, pentanedione; Pz, pyrazine; Tmt, trimethylthiazole.

Example 7

The present inventor has conducted the above-describe examples on *C. elegans* strains which had been collected in various locations. As a result, a strain, which did not exhibit an attraction behavior to urine derived from various types of cancer patients, was found. The genome sequence of this strain was examined. As a result, it was revealed that there are many single nucleotide substitutions on the genome.

Thus, in the present example, the accuracy of cancer detection has been studied using the aforementioned genetic mutant strain, as well as a wild-type strain.

Method:

The chemotaxes of a wild-type strain and a genetic mutant strain to the urine samples of cancer patients having breast cancer, esophageal cancer, bile duct cancer, rectal cancer, cecal cancer, prostate cancer, pancreatic cancer, lung cancer, and gastrointestinal stromal tumor, the urine sample of a healthy subject, and the urine sample of a healthy subject showing false positive in a mid-scale experiment were examined.

Results:

The genetic mutant strain did not exhibit an attraction behavior to the urine of almost all cancer types (FIG. 34).

Since the genetic mutant strain exhibits a normal chemotaxis to other smells, it can be said that the basic olfactory sense thereof functions. Accordingly, it is predicted that the genetic mutant strain will have a defect in a receptor for receiving the smell of cancer types (FIG. 35).

Moreover, the genetic mutant strain exhibits a normal attraction behavior to the false positive samples. Thus, a sample, which had been tested positive by the wild-type strain (N2 strain), was analyzed using a genetic mutant strain, and when the sample was tested negative by the genetic mutant strain, the sample was diagnosed to be cancer, and when the sample was tested positive by the genetic mutant strain, it was diagnosed to be false positive. Accordingly, by using genetic mutant strains, the accuracy of cancer detection can be enhanced (FIG. 35).

Example 8

Identification of Receptor Candidates Associated with Reception of Smells of Individual Cancer Species Using the Next-Generation Sequencer (Illumina), the whole genome sequence of the genetic mutant strain obtained in Example 7 was decoded. Thereafter, the decoded sequence was compared with the genome sequence of N2, and receptor genes having a mutation were searched.

As a result, strong mutations were comprised in receptor genes (Table 6).

TABLE 6

| Olfactory receptor gene | Gastric cancer | Colon cancer | Breast cancer | Pancreatic cancer | Rectal cancer | Lung cancer | Prostate cancer | GIST | Bile duct cancer | Cecal cancer |
|---|---|---|---|---|---|---|---|---|---|---|
| srh family gene | o | o | | | o | o | o | o | o | o |
| srz family gene | | | | o | | o | o | o | o | |
| srg family gene | | o | o | o | | | | | | |

These genes were knocked down by AWC olfactory neuron-specific RNAi (Esposito et al, Efficient and cell specific knock-down of gene function in targeted *C. elegans* neurons. Gene 395, 170-176, 2007), and the chemotaxis to the urine from individual cancer types was then measured.

As a result, it was found that reactive receptors are different depending on cancer species.

Thereby, it becomes possible to specify cancer types according to a nematode chemotaxis test.

The results obtained by examining the chemotaxis of a receptor knockdown strain to the urine of breast cancer patients are shown in FIG. 36.

From studies regarding cancer detection dogs, it has been predicted that individual cancer types have different smells. Thus, the olfactory receptors of nematodes to the smells of individual cancer types are identified, and mutants, which have deletion of the receptor(s), are then produced. An example of the method of producing such a mutant includes a CRISPR/Cas9 method (Friedland et al, Heritable genome editing in *C. elegans* via a CRISPR-Cas9 system, Nature Methods, 2013).

First, as STEP 1, the presence or absence of cancer is tested using an N2 strain.

Next, as STEP 2, a cancer type is specified using a mutant of the receptor of each cancer type. For example, when a receptor mutant for the smell of large bowel cancer does not exhibit an attraction behavior, it can be diagnosed to be large bowel cancer (FIG. 37).

REFERENCES

1. A. Menini, Ed., *The Neurobiology of Olfaction* (CRC Press, Boca Raton, FL, 2010).
2. L. Buck, R. AxelA novel multigene family may encode odorant receptors: a molecular basis for odor recognition. *Cell* 65, 175-187 (1991).
3. S. Serizawa, K. Miyamichi, H. Sakano, One neuron-one receptor rule in the mouse olfactory system. *Trends Genet.* 20, 648-653 (2004).
4. P. Mombaerts, Genes and ligands for odorant, vomeronasal and taste receptors. *Nat. Rev. Neurosci.* 5, 263-278 (2004).
5. H. Saito, Q. Chi, H. Zhuang, H. Matsunami, J. D. Mainland, Odor coding by a Mammalian receptor repertoire. *Sci. Signal.* 2, ra9 (2009).
6. C. I. Bargmann, E. Hartwieg, H. R. Horvitz, Odorant-selective genes and neurons mediate olfaction in *C. elegans*. *Cell* 74, 515-527 (1993).
7. B. M. de, A. V. Maricq, Neuronal substrates of complex behaviors in *C. elegans*. *Annu. Rev. Neurosci.* 28, 451-501 (2005).
8. H. M. Robertson, J. H. Thomas, The putative chemoreceptor families of *C. elegans*. *WormBook,* 1-12 (2006).
9. C. I. Bargmann, Chemosensation in *C. elegans*. *WormBook,* 1-29 (2006).
10. E. R. Liman, Y. V. Zhang, C. Montell, Peripheral Coding of Taste. *Neuron* 81, 984-1000 (2014).
11. P. Sengupta, J. H. Chou, C. I. Bargmann, odr-10 encodes a seven transmembrane domain olfactory receptor required for responses to the odorant diacetyl. *Cell* 84, 899-909 (1996).
12. K. Kim, K. Sato, M. Shibuya, D. M. Zeiger, R. A. Butcher, J. R. Ragains, J. Clardy, K. Touhara, P. Sengupta, Two chemoreceptors mediate developmental effects of dauer pheromone in *C. elegans*. *Science* 326, 994-998 (2009).
13. P. T. McGrath, Y. Xu, M. Ailion, J. L. Garrison, R. A. Butcher, C. I. Bargmann, Parallel evolution of domesticated *Caenorhabditis* species targets pheromone receptor genes. *Nature* 477, 321-325 (2011).
14. D. Park, I. O'Doherty, R. K. Somvanshi, A. Bethke, F. C. Schroeder, U. Kumar, D. L. Riddle, Interaction of structure-specific and promiscuous G-protein-coupled receptors mediates small-molecule signaling in *Caenorhabditis elegans*. *Proc Natl Acad Sci USA* 109, 9917-9922 (2012).
15. E. R. Troemel, B. E. Kimmel, C. I. Bargmann, Reprogramming chemotaxis responses: sensory neurons define olfactory preferences in *C. elegans*. *Cell* 91, 161-169 (1997).
16. M. Y. Chao, H. Komatsu, H. S. Fukuto, H. M. Dionne, A. C. Hart, Feeding status and serotonin rapidly and reversibly modulate a *Caenorhabditis elegans* chemosensory circuit. *Proc. Natl. Acad. Sci. U.S.A.* 101, 15512-15517 (2004).
17. K. Yoshida, T. Hirotsu, T. Tagawa, S. Oda, T. Wakabayashi, Y. lino, T. Ishihara, Odour concentration-dependent olfactory preference change in *C. elegans*. *Nat. Commun.* 3, 739 (2012).
18. R. S. Kamath, A. G. Fraser, Y. Dong, G. Poulin, R. Durbin, M. Gotta, A. Kanapin, B. N. Le, S. Moreno, M. Sohrmann, D. P. Welchman, P. Zipperlen, J. Ahringer, Systematic functional analysis of the *Caenorhabditis elegans* genome using RNAi. *Nature* 421, 231-237 (2003).
19. S. Kennedy, D. Wang, G. Ruvkun, A conserved siRNA-degrading RNase negatively regulates RNA interference in *C. elegans*. *Nature* 427, 645-649 (2004).
20. E. R. Troemel, J. H. Chou, N. D. Dwyer, H. A. Colbert, C. I. Bargmann, Divergent seven transmembrane receptors are candidate chemosensory receptors in *C. elegans*. *Cell* 83, 207-218 (1995).
21. J. Larsch, D. Ventimiglia, C. I. Bargmann, D. R. Albrecht, High-throughput imaging of neuronal activity in *Caenorhabditis elegans*. *Proc. Natl. Acad. Sci. U.S.A.* 110, E4266-4273 (2013).
22. J. H. Chou, C. I. Bargmann, P. Sengupta, The *Caenorhabditis elegans* odr-2 gene encodes a novel Ly-6-related protein required for olfaction. *Genetics* 157, 211-224 (2001).
23. P. Sengupta, Generation and modulation of chemosensory behaviors in *C. elegans*. *Pflugers Arch.* 454, 721-734 (2007).
24. G. Esposito, S. E. Di, C. Bergamasco, P. Bazzicalupo, Efficient and cell specific knock-down of gene function in targeted *C. elegans* neurons. *Gene* 395, 170-176 (2007).
25. J. G. Culotti, R. L. Russell, Osmotic avoidance defective mutants of the nematode *Caenorhabditis elegans*. *Genetics* 90, 243-256 (1978).
26. C. I. Bargmann, J. H. Thomas, H. R. Horvitz, Chemosensory cell function in the behavior and development of *Caenorhabditis elegans*. *Cold Spring Harb. Symp. Quant. Biol.* 55, 529-538 (1990).
27. M. Tsunozaki, S. H. Chalasani, C. I. Bargmann, A behavioral switch: cGMP and PKC signaling in olfactory neurons reverses odor preference in *C. elegans*. *Neuron* 59, 959-971 (2008).
28. D. J. Reiner, D. Weinshenker, H. Tian, J. H. Thomas, K. Nishiwaki, J. Miwa, T. Gruninger, B. Leboeuf, L. R. Garcia, Behavioral genetics of *Caenorhabditis elegans* unc-103-encoded erg-like K(+) channel. *J Neurogenet.* 20, 41-66 (2006).
29. Y. Shinkai, Y. Yamamoto, M. Fujiwara, T. Tabata, T. Murayama, T. Hirotsu, D. D. Ikeda, M. Tsunozaki, Y. lino, C. I. Bargmann, I. Katsura, T. Ishihara, Behavioral choice between conflicting alternatives is regulated by a receptor guanylyl cyclase, GCY-28, and a receptor tyrosine kinase, SCD-2, in AIA interneurons of *Caenorhabditis elegans*. *J Neurosci.* 31, 3007-3015 (2011).
30. T. Nagai, S. Yamada, T. Tominaga, M. Ichikawa, A. Miyawaki, Expanded dynamic range of fluorescent indicators for Ca(2+) by circularly permuted yellow fluorescent proteins. *Proc. Natl. Acad. Sci. U.S.A.* 101, 10554-10559 (2004).
31. J. E. Richmond, W. S. Davis, E. M. Jorgensen, UNC-13 is required for synaptic vesicle fusion in *C. elegans*. *Nat. Neurosci.* 2, 959-964 (1999).

32. S. H. Chalasani, N. Chronis, M. Tsunozaki, J. M. Gray, D. Ramot, M. B. Goodman, C. I. Bargmann, Dissecting a circuit for olfactory behaviour in *Caenorhabditis elegans*. *Nature* 450, 63-70 (2007).
33. H. I. Ha, M. Hendricks, Y. Shen, C. V. Gabel, C. Fang-Yen, Y. Qin, D. Colon-Ramos, K. Shen, A. D. Samuel, Y. Zhang, Functional organization of a neural network for aversive olfactory learning in *Caenorhabditis elegans*. *Neuron* 68, 1173-1186 (2010).
34. C. I. Bargmann, Comparative chemosensation from receptors to ecology. *Nature* 444, 295-301 (2006).
35. J. G. White, E. Southgate, J. N. Thomson, S. Brenner, The structure of the nervous system of the nematode *Caenorhabditis elegans*. *Philos. Trans. R. Soc. Lond. B Biol. Sci.* 314, 1-340 (1986).
36. S. Brenner, The genetics of *Caenorhabditis elegans*. *Genetics* 77, 71-94 (1974).
37. A. G. Fraser, R. S. Kamath, P. Zipperlen, M. Martinez-Campos, M. Sohrmann, J. Ahringer, Functional genomic analysis of *C. elegans* chromosome I by systematic RNA interference. *Nature* 408, 325-330 (2000).
38. A. Solomon, S. Bandhakavi, S. Jabbar, R. Shah, G. J. Beitel, R. I. Morimoto, *Caenorhabditis elegans* OSR-1 regulates behavioral and physiological responses to hyperosmotic environments. *Genetics* 167, 161-170 (2004).
39. A. Lanjuin, M. K. VanHoven, C. I. Bargmann, J. K. Thompson, P. Sengupta, Otx/otd homeobox genes specify distinct sensory neuron identities in *C. elegans*. *Dev. Cell* 5, 621-633 (2003).
40. W. G. Bendena, J. R. Boudreau, T. Papanicolaou, M. Maltby, S. S. Tobe, I. D. Chin-Sang, A *Caenorhabditis elegans* allatostatin/galanin-like receptor NPR-9 inhibits local search behavior in response to feeding cues. *Proc. Natl. Acad. Sci. U.S.A.* 105, 1339-1342 (2008).
41. O. Hobert, I. Mori, Y. Yamashita, H. Honda, Y. Ohshima, Y. Liu, G. Ruvkun, Regulation of interneuron function in the *C. elegans* thermoregulatory pathway by the ttx-3 LIM homeobox gene. *Neuron* 19, 345-357 (1997).
42. E. L. Tsalik, T. Niacaris, A. S. Wenick, K. Pau, L. Avery, O. Hobert, LIM homeobox gene-dependent expression of biogenic amine receptors in restricted regions of the *C. elegans* nervous system. *Dev. Biol.* 263, 81-102 (2003).

43. O. Hobert, T. D'Alberti, Y. Liu, G. Ruvkun, Control of neural development and function in a thermoregulatory network by the LIM homeobox gene lin-11. *J. Neurosci.* 18, 2084-2096 (1998).
44. Z. Altun-Gultekin, Y. Andachi, E. L. Tsalik, D. Pilgrim, Y. Kohara, O. Hobert, A regulatory cascade of three homeobox genes, ceh-10, ttx-3 and ceh-23, controls cell fate specification of a defined interneuron class in *C. elegans*. *Development* 128, 1951-1969 (2001).
45. K. Roayaie, J. G. Crump, A. Sagasti, C. I. Bargmann, The G alpha protein ODR-3 mediates olfactory and nociceptive function and controls cilium morphogenesis in *C. elegans* olfactory neurons. *Neuron* 20, 55-67 (1998).
46. N. Chronis, M. Zimmer, C. I. Bargmann, Microfluidics for in vivo imaging of neuronal and behavioral activity in *Caenorhabditis elegans*. *Nat. Methods* 4, 727-731 (2007).
47. T. Uozumi, T. Hirotsu, K. Yoshida, R. Yamada A. Suzuki, G. Taniguchi, Y. Iino, T. Ishihara, Temporally-regulated quick activation and inactivation of Ras is important for olfactory behaviour. *Sci. Rep.* 2, 500 (2012).

DESCRIPTION OF SIGNS

10: Detection part, 20: Processing part, 30: Storage part, 40: Preservation part
110: Calculation means, 120: Database

SEQUENCE LISTING FREE TEXT

SEQ ID NO: 1: Synthetic DNA
SEQ ID NO: 2: Synthetic DNA
SEQ ID NO: 3: Synthetic DNA
SEQ ID NO: 4: Synthetic DNA All publications and patent literatures such as laid-open publications, patent publications and other patent documents, which are cited in the present description, are incorporated herein by reference. In addition, the present specification includes the contents of the specifications of Japanese Patent Application No. 2013-255145 (filed on Dec. 10, 2013) and U.S. Patent No. 61/982,341 (filed on Apr. 22, 2014), based on which the present application claims priorities.

The invention claimed is:

1. A method for detecting cancer in a subject, comprising the steps of:

(a) exposing a transgenic nematode whose genome comprises a Ca indicator gene operably linked to a promoter expressed in an AWC neuron to a sample from the subject, and (b) testing a calcium response of the AWC neurons of the transgenic nematode to the diluted sample, wherein a change in the calcium response indicates that the subject is determined to have cancer, or to have cancer risk, when the change in the calcium response is increased in comparison to a control as a healthy subject, wherein the Ca indicator gene is selected from the group consisting of YC and GCaMP, wherein the sample is a body fluid, cells, tissues, a culture of the cells or tissues, or a preservative solution of the cells or tissues; and wherein when sample is urine it is diluted to 1.5 to 1000 times or when the sample is a cell culture medium it is diluted to $10^6$ to $10^7$ times, or when the sample is a preservative solution of the cells or a preservative solution of tissues it is diluted to $10^2$ to $10^4$ times.

2. The method according to claim 1, wherein the sample is a urine sample from said subject.

3. The method according to claim 1, wherein said transgenic nematode is of the genus *Caenorhabditis*.

4. The method according to claim 1, wherein the transgenic nematode is *Caenorhabditis elegans*.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
ggcgccgata taattgctaa                                          20

<210> SEQ ID NO 2
<211> LENGTH: 20
<212> TYPE: DNA
<213> ORGANISM: Artificial
<220> FEATURE:
<223> OTHER INFORMATION: Synthetic DNA

<400> SEQUENCE: 2
```
ctgctgcgtt tttcgtatca                                                    20

<210> SEQ ID NO 3
<211> LENGTH: 31
<212> TYPE: DNA
<213> ORGANISM: Artificial
<220> FEATURE:
<223> OTHER INFORMATION: Synthetic DNA

<400> SEQUENCE: 3
gagagctagc aaaaaatgcc tgcaggtcca c                                        31

<210> SEQ ID NO 4
<211> LENGTH: 28
<212> TYPE: DNA
<213> ORGANISM: Artificial
<220> FEATURE:
<223> OTHER INFORMATION: Synthetic DNA

<400> SEQUENCE: 4
gagaggtacc ttattgaatt ctcggttg                                           28

<210> SEQ ID NO 5
<211> LENGTH: 341
<212> TYPE: PRT
<213> ORGANISM: Caenorhabditis elegans

<400> SEQUENCE: 5

Met Pro Ala Gly Pro Pro Cys Pro Ser Ser Ile Pro Thr Tyr Tyr Leu
1               5                   10                  15

Leu Thr Leu His Ile Ile Gly Gly Ile Ser Ile Pro Ile Asn Leu Ile
            20                  25                  30

Gly Phe Tyr Leu Val Trp Phe Gln Ser Pro Lys Met Gln Gly Tyr Lys
        35                  40                  45

Tyr Cys Leu Cys Tyr Leu Gln Leu Val Ser Phe Ile Ala Glu Ile Glu
    50                  55                  60

Met Ile Phe Ile Cys Pro Ala Phe Tyr Phe Phe Pro Leu Ile Gly Gly
65                  70                  75                  80

Phe Asn Val Gly Ala Asp Ile Ile Ala Asn Asn Ile Ser Ser His His
                85                  90                  95

Thr Met Thr Leu Tyr Val Phe Val Phe Thr Phe Glu Leu Pro Ser Thr
            100                 105                 110

Leu Leu Cys Phe Ile Phe Arg His Asn Ala Ala Gly Lys Val Asp Gln
        115                 120                 125

Lys Cys Phe Ser Ser Lys Tyr Leu Lys Lys Phe Ser Leu Val Leu Ala
    130                 135                 140

His Phe Leu Pro Phe Val Thr Ala Phe Cys Phe Trp Asn Ser Arg Leu
145                 150                 155                 160

Thr Ala Lys Glu Arg Met Asp Leu Val Met Asn Asn Trp Pro Gln Cys
                165                 170                 175

Ala His Trp Leu Lys Phe Pro Ala Phe Glu Val Tyr Asp Tyr His Leu
            180                 185                 190

Asn Pro Trp Leu Ala Val Val Gly Ile Gly Ala Phe Phe Val Leu Phe
        195                 200                 205

Met Val Phe Ser Tyr Cys Ile Phe Leu Gly Val Gln Thr Leu Leu Ile
    210                 215                 220

Leu Gln Gln His Arg Lys Ser Met Ser Arg Gln Thr Tyr Gln Ala His
225                 230                 235                 240

-continued

```
Lys Asn Ala Leu Phe Arg Leu Val Met Gln Ile Val Leu Pro Gly Val
                245             250             255

Phe Ile Val Val Pro Leu Cys Ile Cys Met Phe Val Val Val Gln Gly
            260             265             270

Asp Val His Leu Gln Glu Phe Ala Thr Asp Thr Met Phe Phe Val Ser
        275             280             285

Ser His Ser Met Cys Ser Cys Ile Ile Met Ile Ile Ser Asn Pro Lys
        290             295             300

Tyr Arg Ser Val Leu Arg Lys Lys Ile Leu Arg Ile Leu Gly Ile Ser
305             310             315             320

Ala Lys Ser Lys Ser Asn Arg Arg Arg Gly Asn Thr Val Leu Pro Ser
            325             330             335

Gln Pro Arg Ile Gln
            340
```